(12) United States Patent
Waller et al.

(10) Patent No.: US 10,413,450 B2
(45) Date of Patent: *Sep. 17, 2019

(54) BARRIER SYSTEM TO REDUCE THE RATES OF INFECTIONS

(71) Applicant: University of Kansas, Lawrence, KS (US)

(72) Inventors: Stephen Clifford Waller, Overland Park, KS (US); Dhaval Bhavsar, Prairie Village, KS (US)

(73) Assignee: University of Kansas, Lawrence, KS (US)

( * ) Notice: Subject to any disclaimer, the term of this patent is extended or adjusted under 35 U.S.C. 154(b) by 679 days.

This patent is subject to a terminal disclaimer.

(21) Appl. No.: 15/204,624

(22) Filed: Jul. 7, 2016

(65) Prior Publication Data

US 2016/0317359 A1    Nov. 3, 2016

Related U.S. Application Data

(63) Continuation-in-part of application No. 14/610,925, filed on Jan. 30, 2015, now Pat. No. 9,757,539, which
(Continued)

(51) Int. Cl.
*A61F 13/02* (2006.01)
*A61F 15/00* (2006.01)
(Continued)

(52) U.S. Cl.
CPC ...... *A61F 13/0243* (2013.01); *A61F 13/0246* (2013.01); *A61F 15/008* (2013.01);
(Continued)

(58) Field of Classification Search
CPC .......... A61M 25/02; A61M 2025/0246; A61M 2025/0253; A61M 2025/0266;
(Continued)

(56) References Cited

U.S. PATENT DOCUMENTS

| 4,096,853 A * | 6/1978 | Weigand | A61M 25/02 |
| | | | 600/431 |
| 8,945,062 B2 * | 2/2015 | Waller | A61M 5/1418 |
| | | | 604/174 |

(Continued)

*Primary Examiner* — Matthew F Desanto
(74) *Attorney, Agent, or Firm* — Ray Quinney & Nebeker P.C.; Paul N. Taylor

(57) ABSTRACT

A barrier system is provided for use in reducing infections associated with post-operative surgical incision and/or a percutaneous medical device, such as a catheter, that is disposed within the surgical incision. Such a barrier system may include: a barrier device having a skin-contacting surface and a catheter-receiving surface; and an adhesive composition configured for adhering to skin, the barrier device, and/or the catheter so as to form a barrier at or adjacent to an incision in the skin where the catheter is percutaneously inserted through the skin. A tensioning anchor and associated system of two or more tensioning anchors is provided for post-operative wound closure. A method for applying and removing the barrier device and tensioning anchors is also provided.

19 Claims, 27 Drawing Sheets

Related U.S. Application Data is a continuation of application No. 12/334,056, filed on Dec. 12, 2008, now Pat. No. 8,945,062.

(60) Provisional application No. 61/012,990, filed on Dec. 12, 2007, provisional application No. 62/189,615, filed on Jul. 7, 2015, provisional application No. 62/189,616, filed on Jul. 7, 2015.

(51) Int. Cl.
| | | |
|---|---|---|
| *A61M 39/24* | (2006.01) | |
| *A61M 25/02* | (2006.01) | |
| *A61M 39/02* | (2006.01) | |
| *A61M 5/14* | (2006.01) | |
| *A61F 13/00* | (2006.01) | |
| *A61M 5/158* | (2006.01) | |

(52) U.S. Cl.
CPC .......... *A61M 5/1418* (2013.01); *A61M 25/02* (2013.01); *A61M 39/0247* (2013.01); *A61M 39/24* (2013.01); *A61F 2013/00272* (2013.01); *A61M 5/158* (2013.01); *A61M 2025/024* (2013.01); *A61M 2025/0253* (2013.01); *A61M 2039/0261* (2013.01); *A61M 2039/0273* (2013.01); *A61M 2039/0285* (2013.01); *A61M 2039/0294* (2013.01); *A61M 2039/0297* (2013.01)

(58) Field of Classification Search
CPC ... A61M 2039/0297; A61M 2025/0273; A61F 13/0243; A61F 13/0246; A61F 15/008
USPC ................................................ 606/213, 214
See application file for complete search history.

(56) References Cited

U.S. PATENT DOCUMENTS

| | | | | |
|---|---|---|---|---|
| 9,757,539 | B2 * | 9/2017 | Waller | ................ A61M 5/1418 |
| 9,981,075 | B2 * | 5/2018 | Locke | ................ A61M 1/0031 |

\* cited by examiner

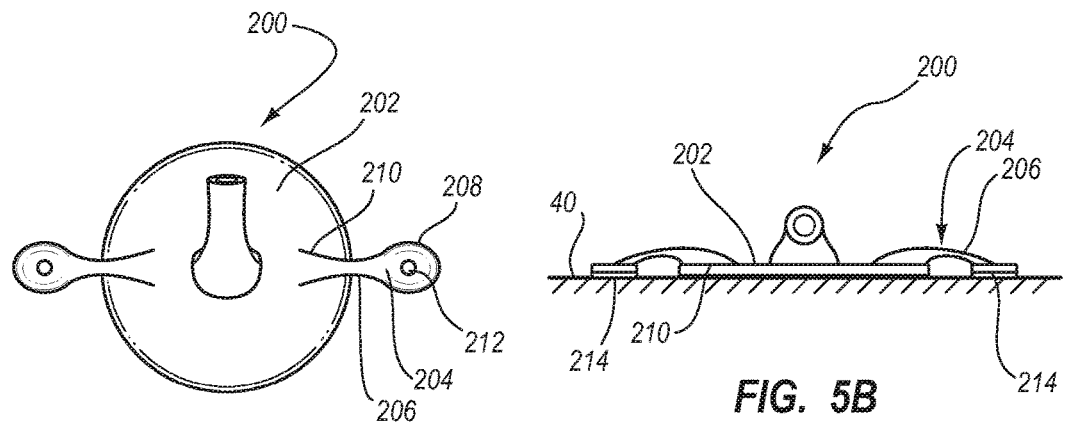
FIG. 5A
FIG. 5B
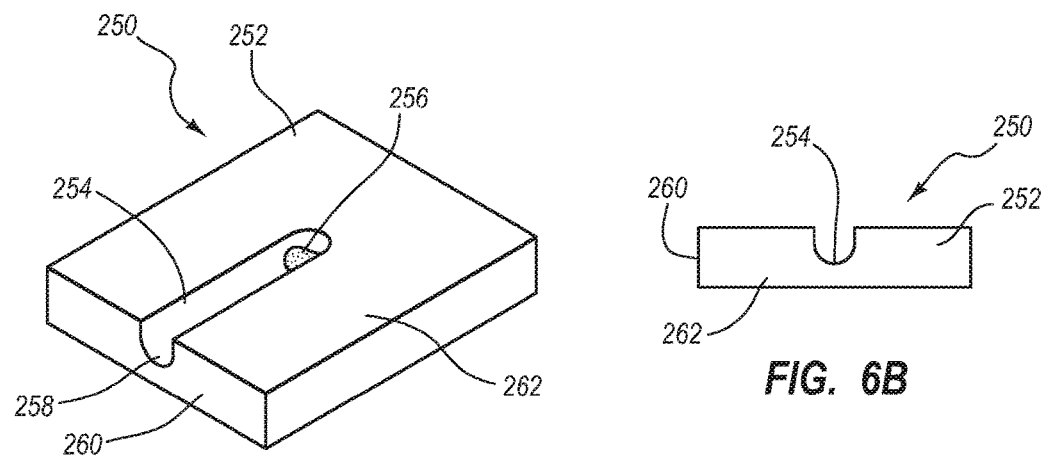
FIG. 6A
FIG. 6B
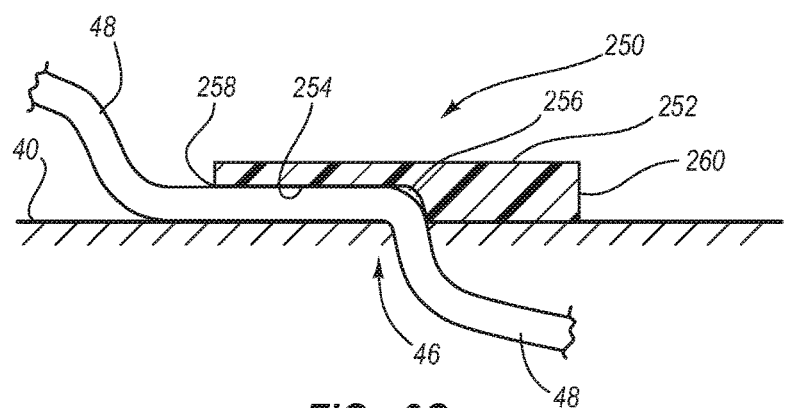
FIG. 6C

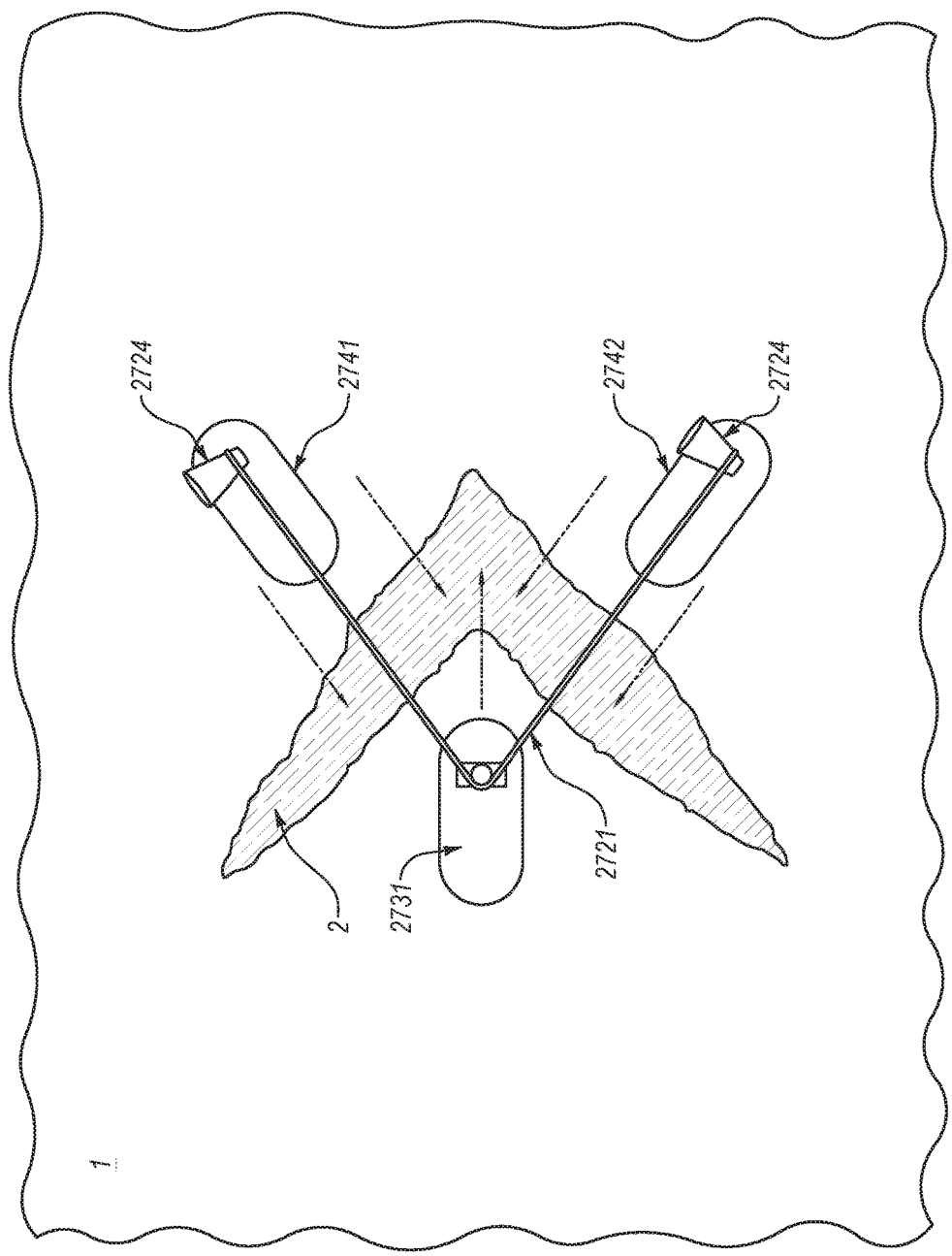

BARRIER SYSTEM TO REDUCE THE RATES OF INFECTIONS

CROSS-REFERENCE TO RELATED APPLICATIONS

This application is a continuation-in-part of U.S. patent application Ser. No. 14/610,925, filed Jan. 30, 2015, which is a continuation of U.S. patent application Ser. No. 12/334,056, filed Dec. 12, 2008, now U.S. Pat. No. 8,945,062, which claims benefit of U.S. Patent Application Ser. No. 61/012,990, filed Dec. 12, 2007, the entireties of which are incorporated herein by reference. This application also claims priority to and the benefit of U.S. Patent Application Ser. No. 62/189,615, filed Jul. 7, 2015 and 62/189,616, filed Jul. 7, 2015, the entireties of which are incorporated herein by reference.

BACKGROUND

Bacterial wound infections following surgical procedures are a very serious problem that have long plagued the medical community. These infections commonly result in prolonged hospital stays and increased costs. Many of these infections occur during the postoperative period, after the patient leaves the operating room, but before a deep surgical wound has had time to heal. Adequate closure and prevention of contamination of the wound during the first several days post-procedure is key.

Typical surgical wound dressings adhere to the skin with a pressure sensitive adhesive (PSA). Though convenient for bandage removal, these PSA's do not significantly impede migration of bacteria along the skin surface. This leaves fresh post-operative wounds particularly vulnerable to gross contamination. In addition, because of their ease of removal, wound dressings adherent to the skin with PSA's are more prone to being dislodged or "rolled-up" at the edges, leaving a wound exposed.

Securing a wound dressing to the skin with a cyanoacrylate adhesive immediately following surgery would provide a superior bacterial barrier compared to standard dressings. Use of cyanoacrylates (or other adhesives with similar barrier properties) would greatly decrease the ability of skin-surface bacteria, in contact with the dressing edges, from migrating freely underneath the dressing. These cyanoacrylate adhesives make accidental dislodgment or "rolling-up" of the dressing, which commonly results from movement in the hospital bed or other activities-of-daily living, much less likely, resulting in better wound protection. Compared to standard PSA's, cured cyanoacrylate polymers themselves are a far superior microbial barrier, inhibiting migration of bacteria through the adhesive itself.

Forced removal of any bandage or other device adhered to the skin via a cyanoacrylate, or similar polymer, could result in skin injury. Given the tremendous bond these adhesives create with skin, these cyanoacrylates are typically allowed to slough off over time. This passive removal method would likely not be acceptable for use in securing a bandage or other medical device to the skin.

The subject matter claimed herein is not limited to embodiments that solve any disadvantages or that operate only in environments such as those described above. Rather, this background is only provided to illustrate one exemplary technology area where some embodiments described herein may be practiced.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one embodiment, the disclosure includes a barrier device that has a top and bottom surface, a compliant portion, an enclosed inner chamber, an adhesive composition, and a port. The compliant portion may be a bladder disposed on the bottom surface of the device. The bladder may also be disposed around the perimeter edges of the barrier device and the inner chamber may reside inside the bladder. The adhesive composition may be a cyanoacrylate and the port may be a Luer lock connection. A pressure sensitive adhesive composition may be disposed on the bottom surface of the barrier device.

In one embodiment, a barrier device includes an inner chamber enclosed by top and bottom layers of the barrier device. The bottom layer may have compliant portions and may have areas of reduced thickness.

In one embodiment, the adhesive composition is encapsulated in a plurality of capsules and disposed on the bottom surface of the barrier device. The encapsulated adhesive composition is configured such that applying pressure to the capsules causes them to become leaky or to break, thus releasing the adhesive composition. In another embodiment of the barrier device, the adhesive composition resides in a groove on the bottom surface of the barrier device. A groove seal covers the adhesive composition within the groove. The adhesive composition, groove, and groove seal are configured such that removing the groove seal exposes the adhesive composition to the air and allows the adhesive composition to polymerize.

In one embodiment, a barrier device includes an absorbent material disposed on the bottom surface of the device and located generally medial to the adhesive composition. The absorbent material is configured to absorb excess fluids on the surface.

In one embodiment, the present disclosure includes a method for removing a barrier device that includes injecting a fluid (e.g., liquid or gas) into the inner chamber and expanding the compliant portion of the barrier device, the expansion weakening the bond between the adhesive composition and the barrier device. The barrier device may then be pulled off of the patient without damaging the skin, while portions of the adhesive composition may remain on the skin.

In one embodiment, the present disclosure includes a method for applying a surface barrier device that includes applying the adhesive composition to the compliant portion of the barrier device and placing the barrier device on the skin of a patient. The placement of the barrier device is such that the adhesive composition residing on the bottom of the barrier device creates a sealed barrier around a surgical incision or wound in the skin. This barrier is situated such that bacteria cannot penetrate the barrier device or make contact with the wound, either by migrating across the surface of the skin or otherwise finding access to the wound.

In one embodiment of the present disclosure, a wound occlusion kit includes a barrier device, an adhesive composition, and a syringe or other injector for injecting a fluid. In one embodiment of the present disclosure, a wound occlusion kit also includes a surface disinfecting fluid and/or tool.

In one embodiment, the present disclosure includes a wound closure tensioning anchor. The tensioning anchor includes a base member, a connecting member, a receiving member, an expandable membrane, and a port. In one embodiment, a tensioning anchor may include an adjustment mechanism that draws the connecting member in towards the anchor or releases it out away from the anchor. In another embodiment, an adjustment mechanism includes a torque limiting slip clutch. In yet another embodiment, the tensioning anchor includes a locking mechanism to lock the connecting member and adjustment mechanism in place. In yet another embodiment, the tensioning anchor may include a force gage to inform a user of the force applied to the skin of a patient by the anchor. In yet another embodiment of a tensioning anchor, the adhesive composition may be a cyanoacrylate and the port may be a Luer lock connection.

In one embodiment of the tensioning anchor, ventilation features are provided to allow air to flow to the skin where the anchor has been adhered. In one embodiment, the expandable membrane is disposed on the bottom surface of the base member. In one embodiment, the expandable membrane is disposed around the perimeter edge of the base member. In one embodiment, a tensioning anchor includes a pulley mechanism that may be coupled to the receiving member.

In one embodiment, the present disclosure includes a method for decreasing the size of an aperture on a patient's skin that includes adhering a first and second anchor to the skin of a patient on opposing sides of the aperture, inserting a connecting member into the receiving members of the anchors, adjusting a distance between the anchors, and locking the connecting member in place. In one embodiment, a method is provided wherein an adjustment mechanism may be activated to draw in or release out the connecting member from one or more of the anchors.

In one embodiment, the present disclosure includes a wound closure kit comprising a connecting member, an adhesive composition, a syringe and/or other injector for injecting a fluid, and at least three closure anchors. In another embodiment, a wound closure kit includes a surface disinfecting fluid and/or tool.

In one embodiment of the present disclosure, a wound closure system includes a first and second tensioning anchor, each tensioning anchor connected to at least one other tensioning anchor via a connecting member. Each of the anchors of the system comprise a base member, a receiving member, an expandable membrane, and a port. Another embodiment of a wound closure system includes a third anchor that is connected to at least one of a first and second anchor via a connecting member.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which:

FIGS. 5A-5B include various views of an embodiment of a barrier device that includes securement straps.

FIGS. 6A-6C include various views of an embodiment of a barrier device that has a medical device-receiving groove in a base surface.

FIG. 27 illustrates a top view of an embodiment of a wound closure system.

DETAILED DESCRIPTION

Figure 1A:
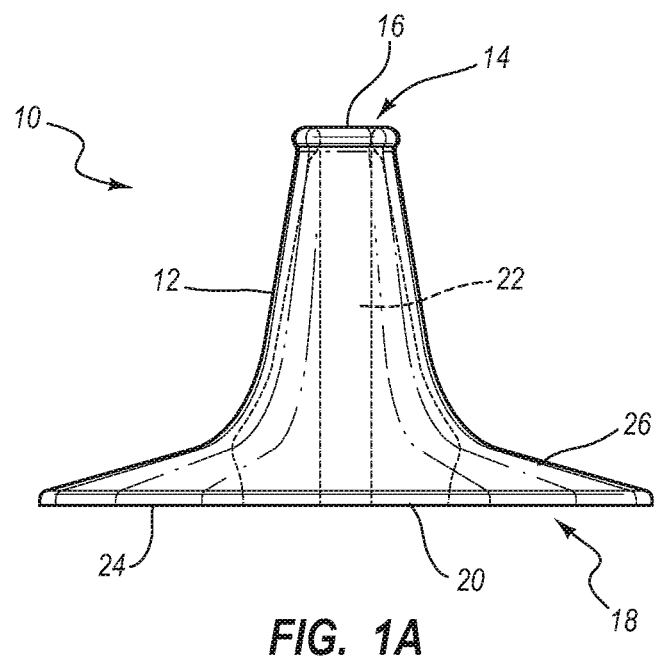
FIGS. 1A-1C include various views of an embodiment of a barrier device in accordance with the present invention.

The present disclosure includes a barrier device, adhesive composition, system having the device and adhesive, and methods of using the device and adhesive that inhibit and/or prevent infections from occurring at or in an insertion site where a medical device (e.g., catheter) penetrates the skin. In one embodiment of the disclosure, a barrier device that has been secured to the skin with a cyanoacrylate or similar adhesive may be removed while reducing the occurrence of tissue damage. The present disclosure also includes a barrier device, adhesive composition, system having the device and adhesive, and methods of using the device and adhesive that inhibit and/or prevent infections from occurring at an aperture (e.g. surgical incision, wound, or other apertures) on a surface such as the skin of a patient.

For example, the insertion site at an aperture may be from a catheter, needle, or other medical device that is inserted through the skin. An aperture may be a wound or surgical incision. Also, the barrier device and adhesive may be used to affix the medical device at a desired position with respect to the insertion site so that the medical device does not move during a medical procedure or during normal patient movement. Affixing the medical device at or around the insertion site to a barrier device can inhibit microbes from migrating into the insertion site by inhibiting the inward and outward slippage of the medical device (e.g., a catheter) with respect to the incision (e.g., pistoning). Thus, in at least one embodiment, the barrier device can be applied to skin at or proximal to an insertion site in the skin with the adhesive in order to inhibit and/or prevent infections from occurring and/or propagating at the insertion site while also inhibiting microbes from migrating into the insertion site by inward and outward slippage of the medical device.

The device and adhesive can cooperate so as to provide a mechanical barrier on the skin at the insertion site as well as adjacent to the aperture. The design of the device and use of the adhesive can allow for the formation of one or more barrier points that can inhibit and/or prevent microbes from entering into the aperture and insertion site. Also, the device and adhesive combination can provide one or more antimicrobial barriers that can inhibit propagation of the microbes that come into contact with the medical device, skin, or the like. A barrier point is formed by adhering the barrier device to skin and optionally adhering the barrier device to the medical device so as to occlude the aperture and/or insertion site. This inhibits microbes from entering into and infecting the aperture and/or insertion site.

The use of a device and adhesive can provide an impermeable barrier against the bacteria that tend to infect catheters by contaminating the catheter at the site of skin entry and subsequently traveling down the external surface of the catheter and into the bloodstream. Importantly, the device and adhesive can be used without the need for many of the antimicrobials and antiseptics that are commonly employed. Such a barrier can eliminate issues of organism resistance that are commonly associated with the currently available antimicrobials and antiseptics. Thus, the device and adhesive can be advantageous in limiting the use of antimicrobials and antiseptics, and thereby reduce the onset or occurrence of drug resistant microbes.

Current practices try to decrease the incidence of catheter-related infections (CRI) by decreasing the bacterial load through antiseptics or antibiotics. However, CRI can now be inhibited or ameliorated by a method of using a composition and/or medical device as a barrier at a site where a medical device is inserted into skin. As such, the inventive composition and/or medical device can block access of the colonizing bacteria to the extraluminal surface of the catheter at the skin-catheter interface. Also, such a method of using the inventive composition and/or medical device can be used in addition to current infection-reducing interventions.

While the barrier device can be used in a manner that does not require the use of an antimicrobial composition, such antimicrobial compositions can be applied at various locations with respect to the barrier device and placement on the skin. For example, the antimicrobial composition, such as a traditional antibiotic or antiseptic (e.g., chlorhexidine, alcohols, quaternary ammonium compounds, boric acid, chlorhexidine gluconate, iodine, etc.) can be manually placed on the skin or aperture prior to placement of the barrier device. Such antimicrobial compositions may also be maintained within a reservoir within the barrier device. This can include the antimicrobial composition being deposited on a skin-contacting surface, medical device-contacting surface, or the like.

Primary closure of complex, often large soft tissue defects following surgical procedures is a common challenge for surgeons. Primary closure of a post-operative wound refers to the closing of a wound directly after the injury occurs. In contrast to wound closure by secondary intention, primary closure simplifies wound care, allowing the wound to heal more quickly and resulting in a better cosmetic outcome. Inability to complete primary closure of a wound results in more wound discomfort, prolonged healing and a larger surgical scar. However, primary closure of wounds under high tension increases the risk for wound dehiscence (i.e. separation of the layers of a surgical wound), a serious surgical complication associated with considerable morbidity and mortality.

Current methods of primary closure of post-operative wounds include the use of sutures and staples, which can leave unsightly scars and are limited in the amount of force they can apply to the skin. Therefore, it may be desirable to have an improved wound closure device and/or method for reducing incidences of post-operative wound dehiscence and minimizing scarring. The present disclosure includes a tensioning anchor device, adhesive composition, system having the anchor device and adhesive, and methods of using the device and adhesive that close an aperture and/or relieves a tension or stress in an aperture on a surface such as the skin of a patient.

I. Barrier Device for Use with Catheters

The barrier device is configured to receive a percutaneous medical device and retain the medical device in a substantially fixed position with respect to the percutaneous incision. The barrier device is also configured to receive an adhesive so as to secure the barrier device to the skin proximal and/or around the incision, where the barrier device can receive the adhesive in one or more locations. The barrier device can have various configurations in order to achieve the functionalities described herein, which can include providing a barrier against contaminants and microbes as well as holding and retaining the medical device in a substantially fixed position such that the medical device does not move into and/or out of the incision during a medical procedure. This can prevent the slight wiggles or repositioning of the medical device that may lead to bacteria entering into the incision.

Additionally, the barrier device can be used to prevent movement of the medical device with respect to the incision during typical patient movement. In many instances, a medical device, such as a pin or rod used for bone alignment, can percutaneously extend through the skin for an extended duration of healing. During this time, the patient is likely to be ambulatory, which in itself can cause the medical device to shift or move into and/or out from the incision. The barrier device of the present disclosure can be utilized for such extended treatments to inhibit or prevent the medical device from moving in or out of the incision.

The barrier device can include a conduit or groove for receiving the medical device. In the instance of a conduit, the medical device can be slid through the conduit or groove before, during, or after insertion through the incision. In the instance of a groove, the barrier device can be applied or snapped onto the medical device after insertion through the incision; however, the barrier device can also be applied or snapped onto the medical device before or during placement into the incision. In another aspect, the barrier device can have an open (e.g., open clam) and closed position (e.g., closed clam), where the opened position allows for the medical device to be passed into an opened conduit before, during, or after insertion into the incision, and the barrier device can then be closed and sealed to provide a closed conduit. After the medical device and barrier device are properly placed as desired or needed, the adhesive can be applied to selected positions of the barrier device so as to adhere the barrier device to the skin and/or medical device. Optionally, the adhesive can be applied to the skin at or around the incision before placement of the barrier device, or applied to the barrier device base before being placed on the skin.

The combination of the barrier device and adhesive can be configured so as to assist in maintaining the medical device (e.g., catheter) in a stable position with respect to the skin and incision, as well as providing a barrier to microbes to inhibit and/or prevent infections related to the percutaneous medical device. Besides catheters, the medical device can be any needle, external fixator pins (used to stabilize fractures of extremities that stick into bone and come out through the skin to an external stabilizing device) "K-wires" (small wires they typically run through finger joints to prevent severe skin contractures, after a burn, from permanently decreasing the range of motion of the fingers; these wires go through bone then exit the skin), and any other percutaneous medical device.

FIGS. 1A-1D provide an illustration of an embodiment of a barrier device 10. FIG. 1A shows that the barrier device 10 is formed from a body 12 that has a first end 14 with a first opening 16 that is opposite from a second end 18 with a second opening 20. The first opening 16 is in fluid communication with the second opening 20 via a substantially straight conduit 22. The body 12 is illustrated to have a tapered cross-sectional profile 28 from the first end 14 to the second end 18. However, the body 12 can have any shape that can provide the barrier/retention properties as described herein. As shown, the first end 14 has a smaller cross-sectional profile 28 compared to the second end 18. Accordingly, the second end 18 can include a base 24 that is configured for placement onto skin 40 such that the conduit 22 is aligned with a percutaneous incision 46. Also, the second end 18 is shown to have a flared portion 26 that provides stability to the device 10 during use. The tapered cross-sectional profile 28 can be tapered at a constant rate, or flared as illustrated.

Figure 1B:
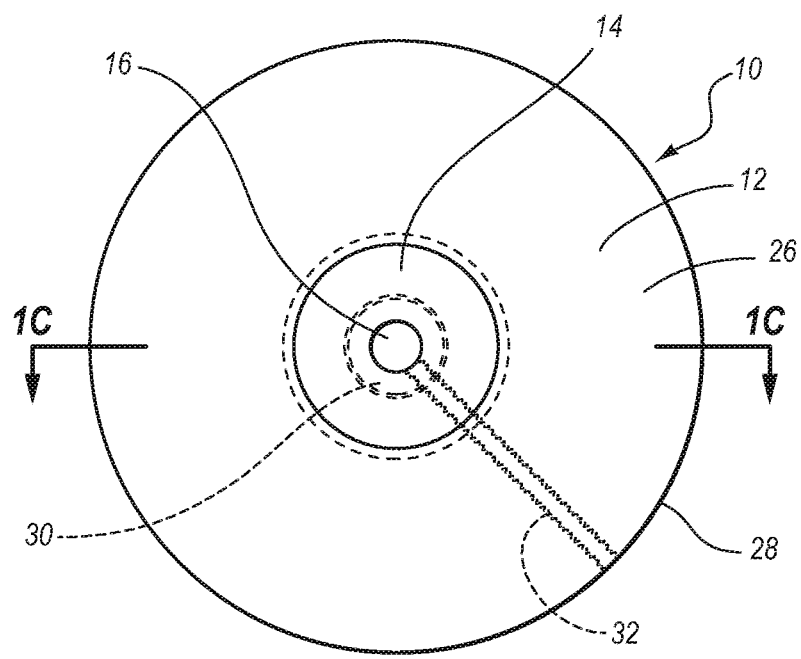

FIG. 1B shows a top view of the barrier device 10, which shows the cross-sectional profile 28 of the body 12 is substantially circular. However, the cross-sectional profile 28 can be any other possible shape, such as triangle, square, rectangle, pentagon, polygon, combinations thereof, and the like. Also, the cross-sectional profile 28 can change shapes from one portion to another portion of the device 10. The first opening 16 can include a taper 30 that narrows into the conduit 22 so that a medical device 48 is easily received therein.

While the body 12 can have a solid circular cross-sectional profile 28 and a closed conduit 22, the body 12 can optionally include a separating slit 32 extending from the first opening 16 to the second opening 20 so that the device 10 can open like a clam. By including a separating slit 32, the device 10 can be applied to a medical device 48 that is already inserted through a percutaneous incision. The configuration of the slit 32 can vary. For example, the slit 32 can include a cooperating junction, blunt end junction, matting junction, or the like. The adhesive that forms the barrier or other adhesive can be used to couple or integrate the sides of the slit 32 together.

Figure 1C:
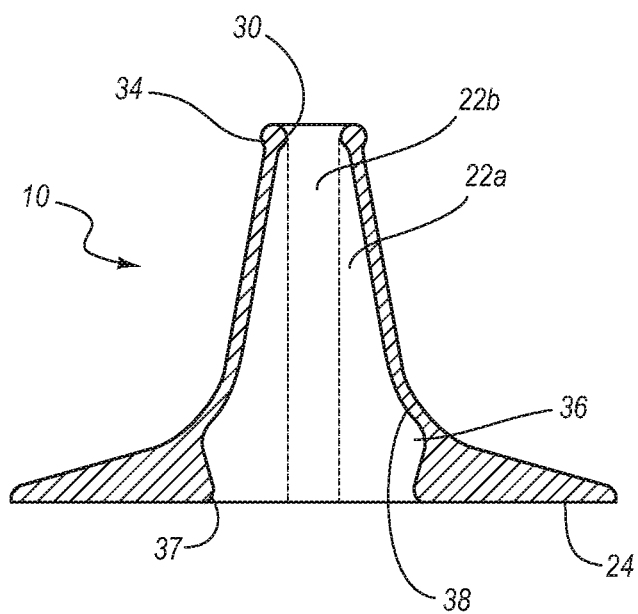

FIG. 1C shows a cutaway side view of the barrier device 10. This view shows the thickness of the body 12 with respect to the cross-sectional profile 28 at various locations along the device 10 or conduit. The first end 14 is shown to have first opening 16 that communicates with the conduit 22. The first opening 16 can include a taper 30 that narrows into the conduit 22 so that a medical device 48 can be passed therethrough and into the conduit 22 with ease. The conduit 22 can have a substantially uniform cross-sectional profile as shown by 22b, or the conduit 22 can have a tapered conduit as shown by 22a. While not shown, the conduit 22 can also have a widening conduit that is wider at the first opening 16 compared to the second opening 20. The thickness of the body 12 is dependent on the overall shape of the body 12 as well as the shape of the conduit 22.

The first end 14 is shown to have a thicker body portion at the lip 34 of the first opening 16. The lip 34 can provide increased structural integrity so that the barrier device 10 does not crack, split, or otherwise break during use or when the medical device 48 traverses through the conduit 22.

At the second end 18, the base 24 is shown to have a substantial surface area for contacting with the skin 40. This can provide the base 24 with substantial stability in contacting the skin and being retained in place, as desired or needed.

The conduit 22, while being uniform (22b) or tapered (22a) can also include recesses 36 or the like that can be used as reservoirs for the adhesive and/or an antimicrobial composition. The adhesive can be applied to the recess 36 so that the medical device can be adhered to a conduit surface 38. Also, the second opening 20 can include an expanded area, which can be formed from a tapered surface when entering the conduit 22 from the second opening 20. The expanded area can be configured for receiving adhesive in a location adjacent to the skin 40 so as to adhere the skin 40 to the medical device 48 and barrier 10 at locations around or adjacent to the incision 46.

Figure 1D:
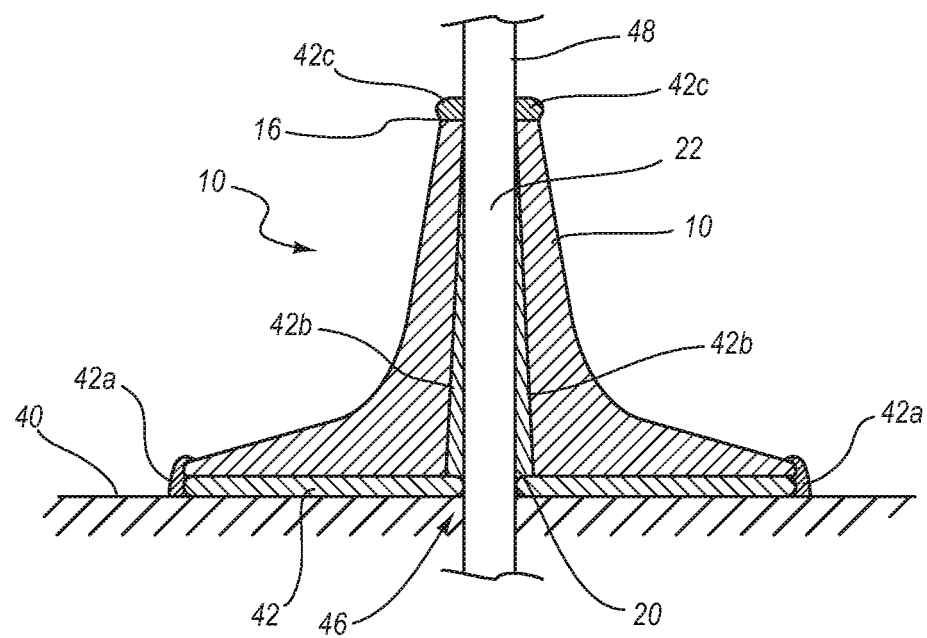
FIG. 1D includes an illustration of the barrier device of FIGS. 1A-1C during use.

FIG. 1D shows a cutaway side view of the device 10 illustrated in FIGS. 1A-1C during use. The device 10 is applied to the skin 40 and adhered thereto by having adhesive 42 applied to a portion, annular area, or entire base 24 of the device 10. Also, the adhesive 42a can be applied to the perimeter 44 of the base 24 to form an outer seal (42a). The device 10 is adhered to the skin 40 such that the conduit 22 is aligned with a percutaneous incision 46 that extends into tissue under the skin 40. This allows a medical device 48 (e.g., catheter) to be placed in the conduit 22 and into the incision 46.

Optionally, adhesive 42 can be placed in the conduit 22 to form a conduit seal 42b, on the first opening 16 to form a first opening seal 42c, on the second opening 20 to form a second opening seal 42d, or the like. The adhesive 42 can be applied to any location on the device 10 that is in contact with skin 40 and/or the medical device 48.

FIGS. 2A-2D illustrate another embodiment of a barrier device 50 that has many features in common with the barrier device 10 of FIGS. 1A-1D. The barrier device 50 is formed from a body 52 that has a base member 54 with a base opening 56 that is coupled to an elongate, bent tube 58 with a tube opening 60. The base opening 56 is in fluid communication with the tube opening 60 via a bent conduit 62. As shown, the base member 54 has a substantially constant cross-sectional profile 68, and is coupled to the tube 58, which has a varying cross-sectional profile 68. The base member 54 and the tube 58 can be a uniform member or two separate members that are coupled together. The base member 54 can include a base surface 64 that is configured for placement onto skin such that the conduit 62 is aligned with a percutaneous incision 46.

Figure 2A:
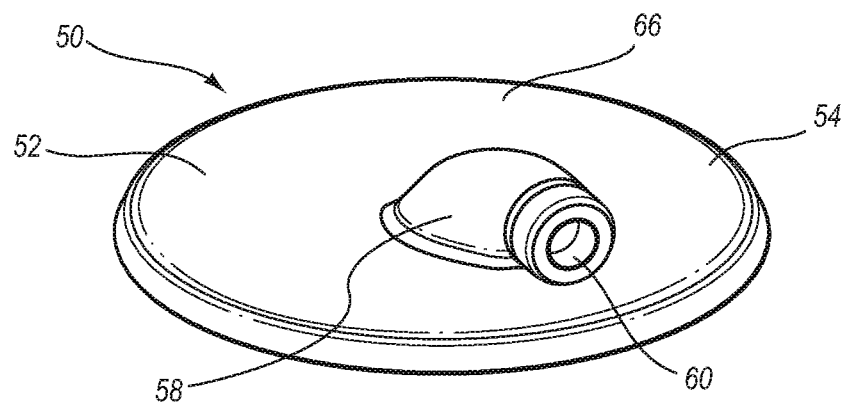
FIGS. 2A-2C include various views of an embodiment of a barrier device in accordance with the present disclosure.
Figure 2B:
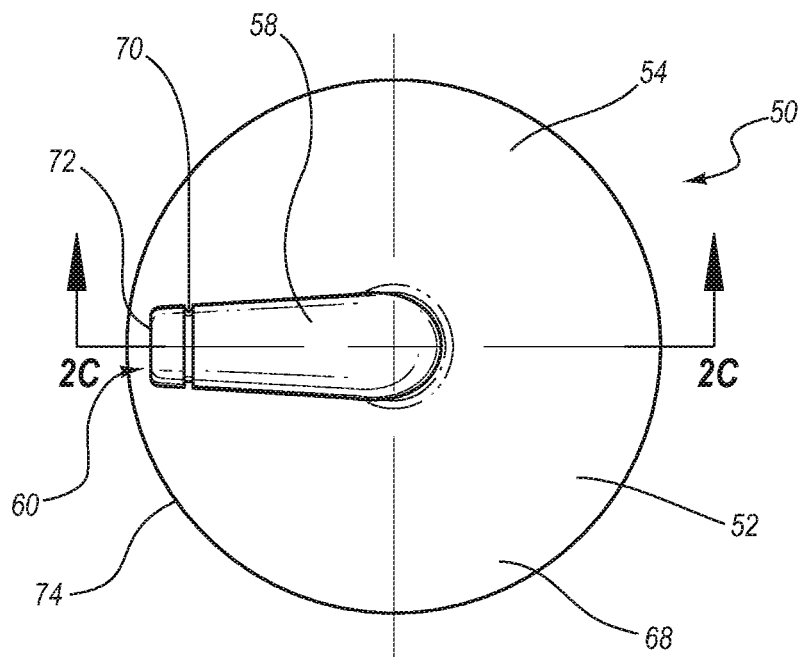

FIG. 2B shows a top view of the barrier device 50, which shows the cross-sectional profile 68 of the body 52 is substantially circular. However, the cross-sectional profile 68 can be any other possible shape, such as triangle, square, rectangle, pentagon, polygon, combinations thereof, and the like. The tube 58 is shown to be positioned such that the tube opening 60 is directed laterally from the base member 54. Also, the tube 58 is shown to include a circumferential groove 70 that is configured to receive a fastener member (not shown) of a medical device. For example, the medical device can include an annular protrusion that aligns with the groove 70 so at to mate and fasten the device 50 with the medical device. Alternative, the groove 70 can receive a restricting member (not shown) such as an o-ring, suture, or the like that can contract and constrict the tube 58 so that the conduit 62 grabs the medical device so inhibit movement therebetween. In another alternative, the groove 70 can be used to receive adhesive so as to form a seal at the tube opening 60 with the medical device 48. Also, the groove 70 can be used to receive a suture to increase security of the medical device with respect to the barrier device 50.

While the tube end 72 is shown to terminate before reaching the outer perimeter 74 of the base member 54, the tube end 72 can extend past or be the terminate at the outer perimeter 74 of the base member 54. The base member 54 and tube 58 can include a openable slit (not shown) such that the device 50 can open up like a clam in order to receive the medical device into the conduit 62.

Figure 2C:
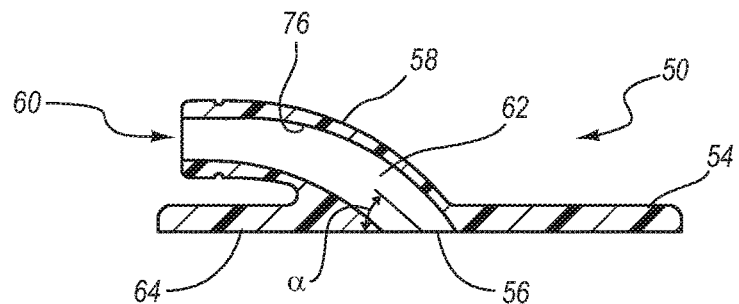

FIG. 2C shows a cutaway side view of the barrier device 50. This view shows the thickness of the body 52 with respect to the cross-sectional profile 68 at various locations along the device 50 or conduit 62. The base member 54 is shown to have base opening 56 that communicates with the conduit 62. The base opening 56 is shown to have an offset opening that is at an angle alpha with respect to the base surface 64, which would also be at an angle with respect to the skin 40 and tube 58. The conduit 62 can have a substantially uniform cross-sectional profile 68, or the conduit 62 can have a tapered conduit, or a shape that conforms with the external surface 66 of the device 10. The thickness of the body 52 is dependent on the overall shape of the body 52 as well as the shape of the conduit 62.

The base surface 64 is shown to have a substantial surface area for contacting with the skin 40. This can provide the base member 54 with substantial stability in contacting the skin 40 and being retained in place, as desired or needed.

While not shown, the conduit 62 can include recesses, expanded openings, or the like that can be used as reservoirs for the adhesive. The adhesive can be applied to the recess so that the medical device can be adhered to a conduit surface 76. The base member 54 and/or body 52 can also include recesses to be used as reservoirs for receiving the adhesive and affixation to the skin.

Figure 2D:
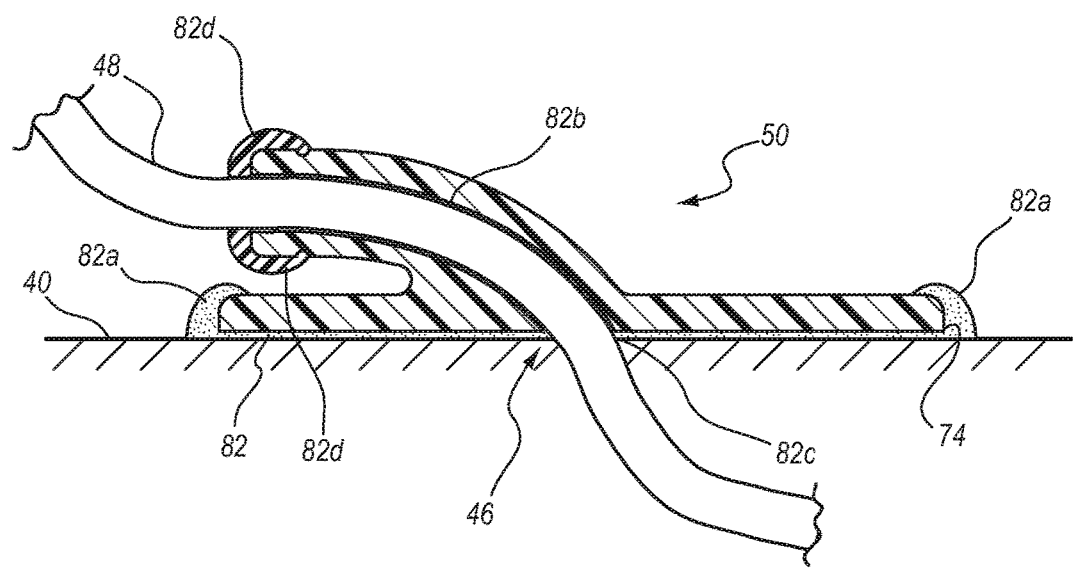
FIG. 2D includes an illustration of the barrier device of FIGS. 2A-2C during use.

FIG. 2D shows a cutaway side view of the device 50 illustrated in FIGS. 2A-2C during use. The device 50 is applied to the skin 40 and adhered thereto by having adhesive 82 applied to a portion, annular area, or entire base 64 of the device 50. Also, the adhesive 82a can be applied to the perimeter 74 of the base 54 to form an outer seal (82a). The device 50 is adhered to the skin 40 such that the conduit 62 is aligned with a percutaneous incision 46 that extends into tissue under the skin 40. This allows a medical device 48 (e.g., catheter) to be placed in the conduit 62 and into the incision 46.

Optionally, adhesive 82 can be placed in the conduit 62 to form a conduit seal 82b, on the base opening 56 to form a base opening seal 82c, on the tube opening 60 to form a tube opening seal 82d, or the like. The adhesive 42 can be applied to any location on the device 50 that is in contact with skin 40 and/or the medical device 48.

Figure 3A:
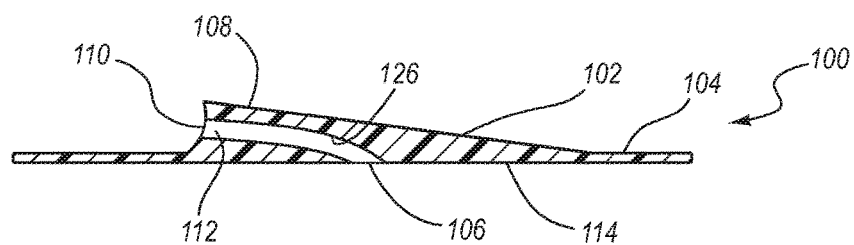
FIGS. 3A-3C include various views of an embodiment of a barrier device in accordance with the present disclosure.
Figure 3B:
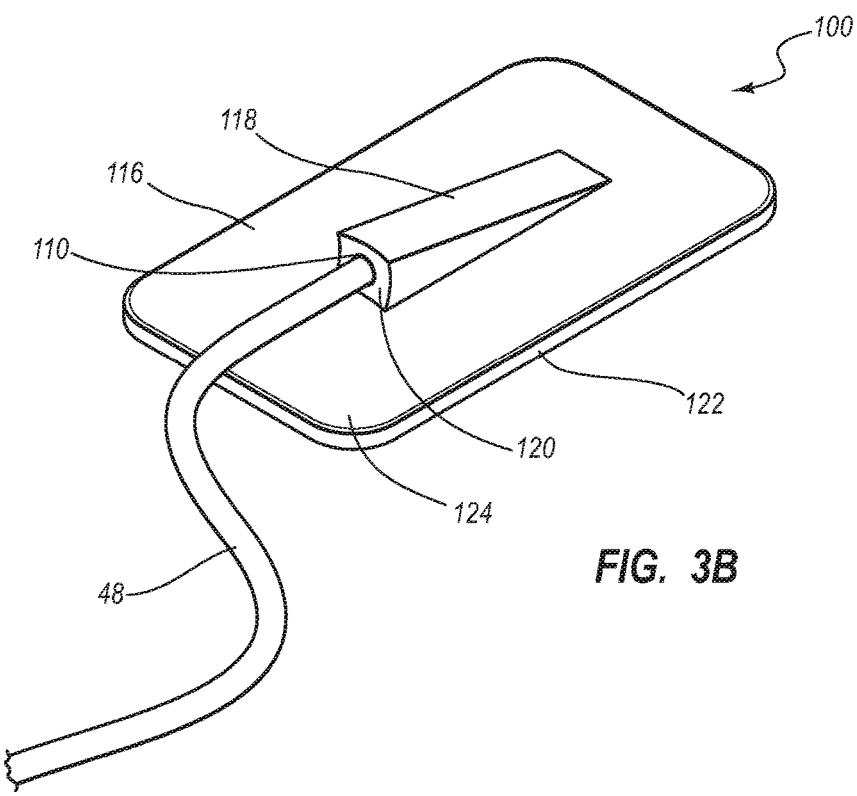
Figure 3C:
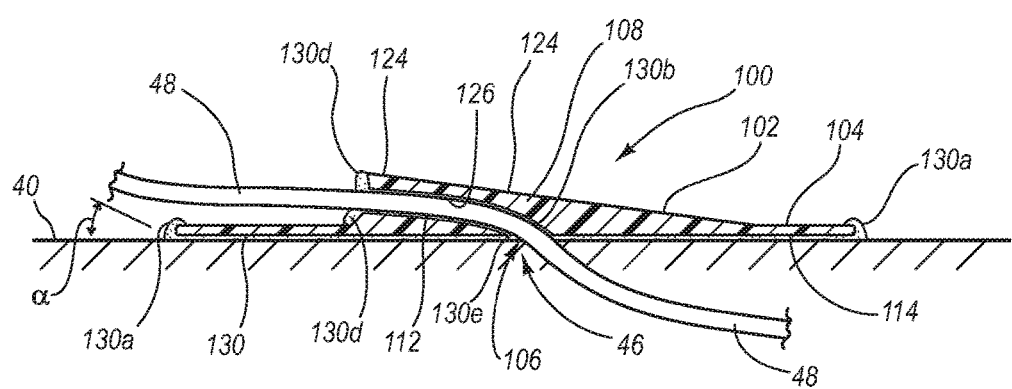

FIGS. 3A-3C illustrate another embodiment of a barrier device 100 that has many features in common with the barrier device 10 of FIGS. 1A-1D or device 50 of FIGS. 2A-2D. The barrier device 100 is formed from a body 102 that has a base member 104 with a base opening 106 that is coupled to a top member 108 with a top opening 110. The base opening 106 is in fluid communication with the top opening 110 via a conduit 112. As shown, the base member 104 has a substantially constant cross-sectional profile 116, and is coupled to the top member 108, which can have any cross-sectional profile 118. The base member 104 and the top member 108 can be a uniform member or two separate members that are coupled together. The base member 104 can include a base surface 114 that is configured for placement onto skin 40 such that the conduit 112 is aligned with a percutaneous incision 46.

FIG. 3B shows a top view of the barrier device 100, which shows the cross-sectional profile 116 of the base member 104 is substantially rectangular. However, the cross-sectional profile can be any other possible shape, such as triangle, square, circle, pentagon, polygon, combinations thereof, and the like. Similarly, the cross-sectional profile 118 of the top member 108 can be any shape, such as those described. The top member 108 is shown to be positioned such that the top opening 110 is directed laterally from the base member 104. Also, the top member 108 is shown to include a concave face 120, however, the face 120 can be blunt, convex or the like. The concave face 120 can aid in inserting the medical device into the conduit 112.

While the face 120 of the top member 108 is shown to terminate before reaching the outer perimeter 122 of the base member 104, the face 120 can extend past or be the terminate at the outer perimeter 122 of the base member 104. The base member 104 and top member 108 can include a openable slit (not shown) such that the device 100 can open and close like a clam in order to receive the medical device into the conduit 112.

FIG. 3C shows a cutaway side view of the barrier device 100 in use. This view shows the thickness of the body 102 with respect to the cross-sectional profile 116, 118 at various locations along the device 100 or conduit 112. The base member 104 is shown to have base opening 106 that communicates with the conduit 112. The base opening 106 is shown to have an offset opening that is at an angle alpha with respect to the base surface 114, which would also be at an angle with respect to the skin 40 and top member 108. The conduit 112 can have a substantially uniform cross-sectional profile, or the conduit 112 can have a tapered profile, or a shape that conforms with the external surface 124 of the device 10. The thickness of the body 102 is dependent on the overall shape of the body 102 as well as the shape of the conduit 112.

The base surface 114 is shown to have a substantial surface area for contacting with the skin 40. This can provide the base member 104 with substantial stability in contacting the skin 40 and being retained in place, as desired or needed. However, a base surface 114 having a minimal surface area could also be used to provide a barrier.

While not shown, the conduit 112 can include recesses, expanded openings, or the like that can be used as reservoirs for the adhesive. The adhesive can be applied to the recess so that the medical device can be adhered to a conduit surface 126.

The device 100 is applied to the skin 40 and adhered thereto by having adhesive 130 applied to a portion, annular area, or entire base surface 114 of the device 100. Also, the adhesive 130a can be applied to the perimeter 122 of the base 104 to form an outer seal (130a). The device 100 is adhered to the skin 40 such that the conduit 112 is aligned with a percutaneous incision 46 that extends into tissue under the skin 40. This allows a medical device 48 (e.g., catheter) to be placed in the conduit 112 and into the incision 46.

Optionally, adhesive 130 can be placed in the conduit 112 to form a conduit seal 130b, on the base opening 106 to form a base opening seal 130c, on the top opening 110 to form a top opening seal 130d, or the like. The adhesive 130 can be applied to any location on the device 100 that is in contact with skin 40 and/or the medical device 48.

Figure 4A:
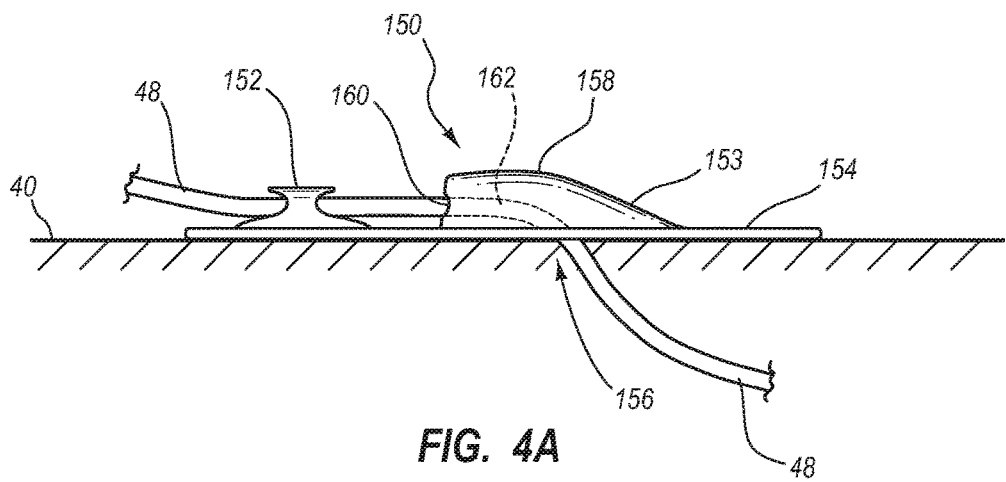
FIGS. 4A-4E include various views of an embodiment of a barrier device that includes a fastener, and also show different embodiments of fasteners for fastening a medical device to the barrier device.
Figure 4B:
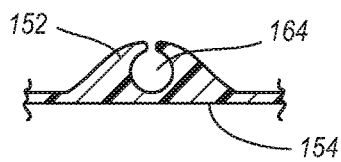

FIGS. 4A-4B illustrate another embodiment of a barrier device 150 that has many features in common with the barrier device 10 of FIGS. 1A-1D, device 50 of FIGS. 2A-2D, and device 100 of FIGS. 3A-3C. As illustrated, the barrier device 150 is configured substantially the same as the device of FIGS. 3A-3C; however, the features of FIGS. 4A-4B can also be applied to any barrier device described herein, and vice versa. The barrier device 150 is shown to include a fastener 152 that fastens the medical device 48 to the barrier device 150. The fastener 152 is advantageous in retaining the tube of the medical device 48 against the barrier device 150, which can aid in the retention and barrier properties of the device 150. Briefly, the barrier device 150 is formed from a body 153 that has a base member 154 with a base opening 156 that is coupled to a top member 158 with a top opening 160. The base opening 156 is in fluid communication with the top opening 160 via a conduit 162.

The fastener 152 is disposed on the base member 154 in a position that allows for receiving the medical device 48. The fastener 152 is configured similarly to a "C" clamp that can be manually opened by hand to receive the medical device 48. For example, the medical device 48 can be snapped into the fastener 152 so as to be received into the fastener receiver 164. The medical device 48 can then be removed from the fastener 152 by snapping the medical device 48 from the receiver 164, which can be done by hand.

Figure 4C:
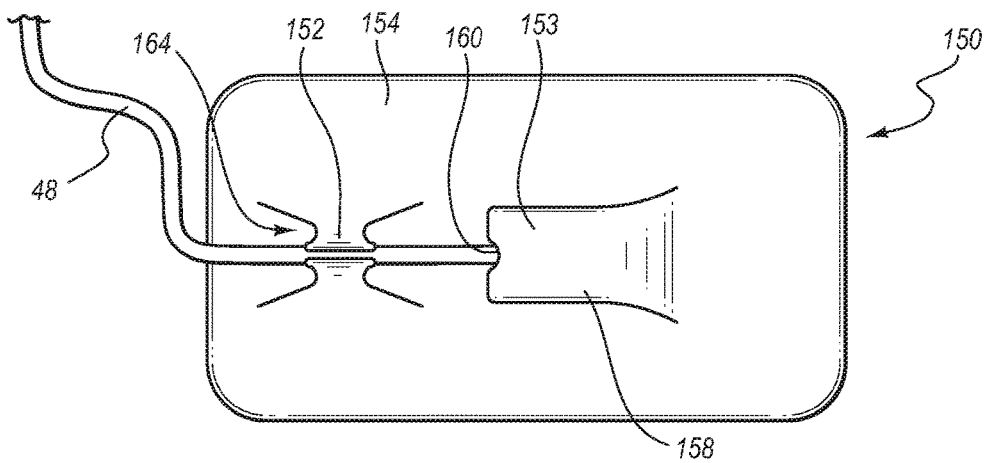
Figure 4D:
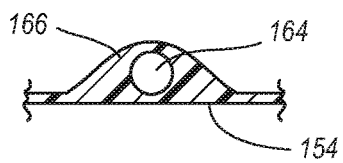
Figure 4E:
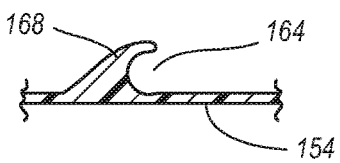

While the fastener 152 is shown to be in a "C" clamp configuration in FIG. 4A-4C, other types of fasteners can be employed, which can include a conduit fastener 166 (FIG. 4D), half fastener 168 (FIG. 4E), or the like. In fact, any suitable type of fastening system, such as those that are removable, releasable, flexible, elastic, and the like can be used with the barrier device.

FIGS. 5A-5B illustrate another embodiment of a barrier device 200 that has many features in common with the device 50 of FIGS. 2A-2D. However, the features of FIGS. 5A-5B can also be applied to any barrier device described herein, and vice versa. As shown, the barrier device includes a base 202 configured as described herein. The base 202 includes one or more fastener straps 204 that extend from the base 202 so as to be disposed over the skin 40 when applied to a subject. The device 200 is shown to have two fastener straps 204; however, more or less straps 204 can be used. Each strap 204 can include a body 206 that has a terminal head 208 that can be disposed on the skin 40. the body 206 can be connected to the base 202 at a connection point 210, which can be rigid, flexible, stretchable, or the like. The strap 204 can be prepared from a uniform material with the base 202, or can be two separate members that are coupled together. The head 208 can be solid or have a hole 212. The head 208 can be configured for being affixed to the skin 40 in a fixed or removable manner. For example, the head 208 can be glued to the skin 40 with adhesive 214 (as shown) or sutured to the skin 40 with sutures (not shown). Other means of affixation can also be used. The straps 204 can improve the retention of the barrier device 200 to the skin 40. While the straps 204 are shown to have a defined shape, other shapes and configurations can be used so at to increase the retention of the barrier device 200 on the skin 40 so that it does not move during the medical procedure.

The barrier device can be prepared from any medically acceptable material. That is, any material that is used for a medical device, ranging from catheters to bandages, can be used in preparing a boot as described and shown herein. For example, the boot, which can be in various shapes and sizes, can be prepared from rubbers, elastomers, bandage-like materials, cloth, fibrous materials, paper, porous materials, plastics, hard plastics, maleable plastics, polyethylenes, polystyrenes, foams, memory foams, polyurethanes, latexes, and the like.

In one embodiment, the barrier device does not have an aperture or closed conduit, but can be configured to lay over a percutaneous medical device. The barrier device can have a receiving surface or recess that can receive the medical device. For example, the recess can be a semi-circular conduit that lays over the medical device and on the skin. As such, the barrier device can have a medical device receiving surface, groove, recess, or the like that can be flat, flexible, bendable, malleable, grooved so as to receive a catheter, and the like.

FIGS. 6A-6B show an embodiment of a barrier device 250 that includes a body 252 having a recess 254 configured for receiving a medical device 48. The recess 254 can have a closed end 256 that is located within the body 252. The closed end 256 can be configured for receiving the portion of the medical device 48 that protrudes from the percutaneous incision 46 in the skin 40. At the other end of the recess 254 is an open end 256 that opens from the device 250 so that the medical device can extend past the perimeter 260 of the device 250. The adhesive (not shown) can be applied to any portion of the device as described herein, including at any point on the recess 254 or perimeter 260 or base 262 of the body 252.

Figure 7A:
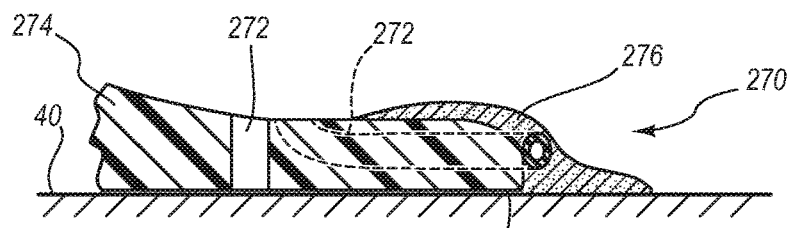
FIGS. 7A-7B include various views of an embodiment of a barrier device that includes chilling conduits.
Figure 7B:
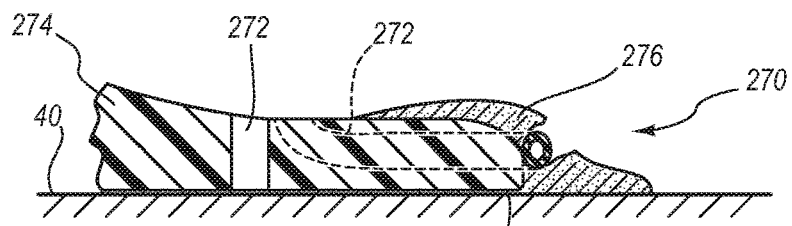

As shown in FIGS. 7A-7B, an embodiment of a barrier device 270 can include one or more chilling conduits 272 formed in the portion of the body 274 that contacts the skin. The chilling conduits 272 can be the same or different from the conduits described herein for receiving the medical device. The chilling conduits 272 are configured for receiving a chilled fluid that can be applied through the conduits 272 so as to provide the chilled fluid to the adhesive 276. Chilling can cause the adhesive 276 to become brittle and easily broken and/or separated from the skin. Suitable chilling fluids can include dimethyl ether, propane, liquid nitrogen, tetrafluoroethane, and the like. The use of chilling fluids can aid in removal of the device 270 when it is time to remove the medical device from the incision.

While chilling conduits are illustrated, such chilling conduits can be present in various sizes and configurations. The chilling conduit can be at any of the following: at a perimeter edge of the barrier device; around the perimeter of the barrier device; at the base of the barrier device; around the medical device conduit; around the top opening from which the medical device protrudes; in fluid communication with the medical device conduit; a conduit in communication with one or more of the foregoing conduits; combinations thereof; and the like. Additionally, components for introducing a chilling fluid into the chilling conduits can be included in the present disclosure, such as reservoirs of chilling fluids, tubing, tube fittings, syringes, and the like.

In one embodiment, the conduits, such as chilling conduit or medical device conduit, can include linings. As such, another material such as a polymer, metal, alloy, ceramic, fiberglass, or the like can be coated along the surface of the conduit to provide various properties. Such linings can be advantageous in providing structural integrity or for increasing the heat (cold) transfer characteristics for more rapid temperature changes.

In one embodiment, the chilling conduit can be filled within another material to change the properties of the barrier device. For example, the conduits can be filled with other polymers, metals, alloys, fiberglass, fiber optics, or the like. A metal-filled conduit can be used to provide cooler temperatures to the adhesives located on the other end of the conduit to increase the cooling of the adhesive. Metal conduits can also be used to propagate electricity across the adhesive to degrade adhesives that are subject to degradation when exposed to electrical currents. Also, a fiber optic-filled conduit, or other wave-guide or wave carrier, can be useful when the adhesive is subject to degradation upon receiving laser light or other energetic waves that can weaken the adhesive.

Figure 8A:
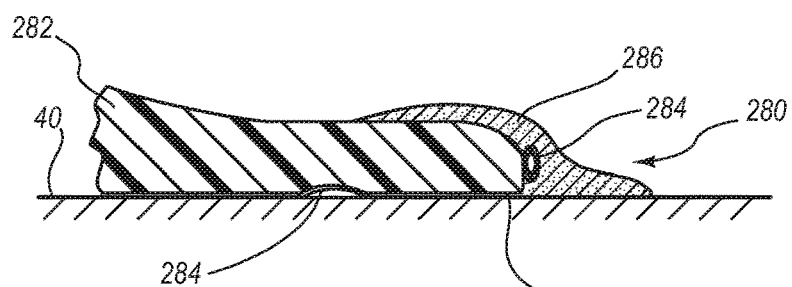
FIGS. 8A-8B include various views of an embodiment of a barrier device that includes an expandable bladder.
Figure 8B:
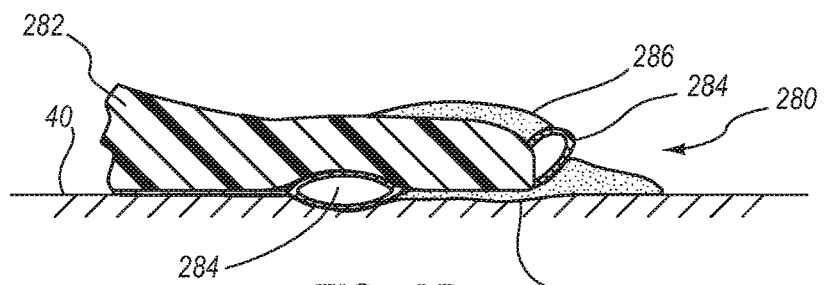

As shown in FIGS. 8A-8B, an embodiment of a barrier device 280 can include one or more expandable bladders 284 at locations on the body 282 of the barrier device 280 that contact the skin. During use, the bladders 284 can be in unexpanded states, and when the it is time for the medical device to be withdrawn, the bladders 284 can be expanded. Such an expansion can break the seal of the adhesive 286 so that the barrier device 280 can be easily removed from the skin. For example, the bladder 284 can be disposed on the base surface 288 of the body 282. While not shown, the body can also include conduits for passing gasses to the bladder 284 to enable inflation. Also, hypodermic needles or the like can be used to supply gasses to the bladder 284 to effect expansion.

Figure 9:
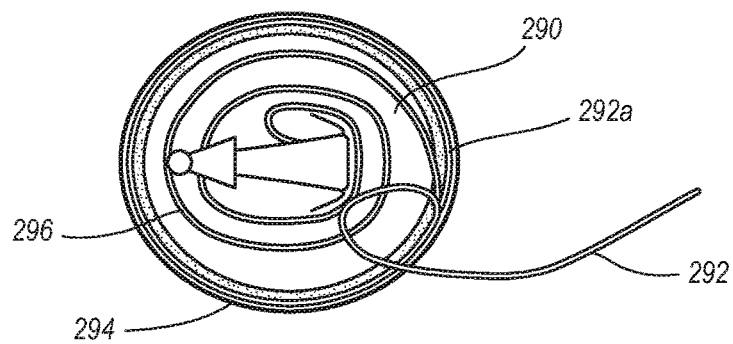
FIG. 9 includes an embodiment of a barrier device that includes a release cord.

FIG. 9 illustrates an embodiment of a barrier device 290 that can include a release cord 292. While shown to be located at the outer perimeter 294 of the device 290, the release cord 292 can be disposed anywhere on the device 290 that contacts the skin. For example, the release cord 292 can be in a coil formation 296 that coils along the base surface of the device. When it is time to remove the medical device from the incision, the release cord 292 can be pulled so as to break the seal and barrier between the barrier device 290 and the skin.

Figure 10A:
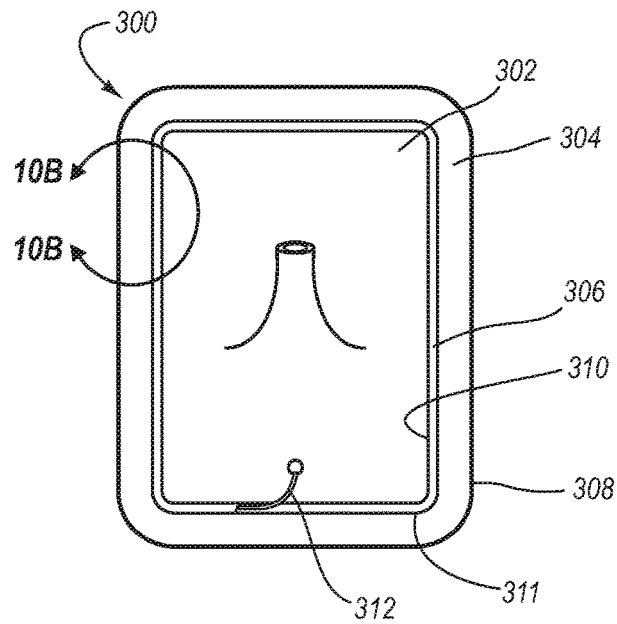
FIGS. 10A-10C include various views of an embodiment of a modular barrier device that includes decouplable members that can be separated by pulling a release wire.
Figure 10B:
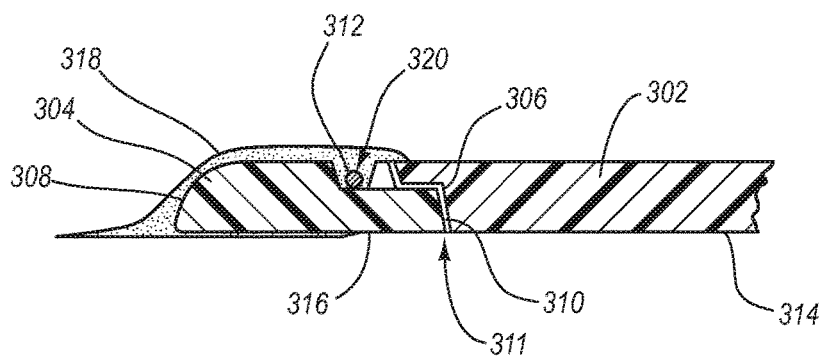
Figure 10C:
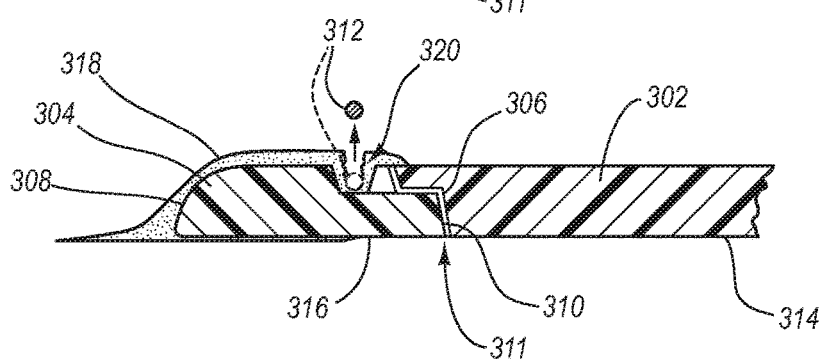

FIGS. 10A-10C illustrate an embodiment of a modular barrier device 300. The modular barrier device 300 can include a main barrier 302 and a perimeter barrier 304. The main barrier 302 can be configured as any barrier device as described herein. The perimeter barrier 304 is sized so as to be coupled/couplable to the perimeter surface 306 of the main barrier 302. For example, the perimeter barrier 304 can include an outer perimeter surface 308 and an inner perimeter surface 310 that is shaped and sized to conform with the perimeter surface 306 of the main barrier 302. When the main barrier 302 and perimeter barrier 304 are placed together so as to form the modular barrier device 300, the perimeter surface 306 forms a gap 311 with the inner perimeter surface 310 of the perimeter barrier 304. A wire 312 can be imbedded on, within, at, or adjacent to the gap 311, such that pulling the wire 312 allows for the main barrier 302 to be decoupled from the perimeter barrier 304. As shown, the wire 312 is disposed within a wire recess 320 that extends around inner perimeter surface 310 of the perimeter barrier 304; however, the wire 312 and wire recess 320 can be in or at the gap 311 as well as within the main barrier 302 proximal or adjacent to the perimeter surface 306 of the main barrier 302.

FIG. 10B illustrates the modular barrier device 300 as applied to skin (not shown) with adhesive 318. The main barrier 302 includes a main base surface 314 that is shown to be disposed on the skin without adhesive; however, adhesive can be applied to the main base surface 314. The perimeter device 304 includes a perimeter base surface 316 which is shown to be affixed to the skin with adhesive 318. The adhesive 318 is shown to be on the perimeter base surface 316, outer perimeter surface 308 and over the gap 311.

FIG. 10C illustrates the modular barrier device 300 being removed from the skin. As shown, the wire 312 is pulled from the wire recess 320 so as to cut, disrupt, separate, or otherwise remove the adhesive 318 from the device 300. This includes cutting the adhesive 318 adjacent to the wire recess 320 and/or gap 311 so that main barrier 302 can be separated from the perimeter barrier 304 and pulled from the skin.

Figure 11A:
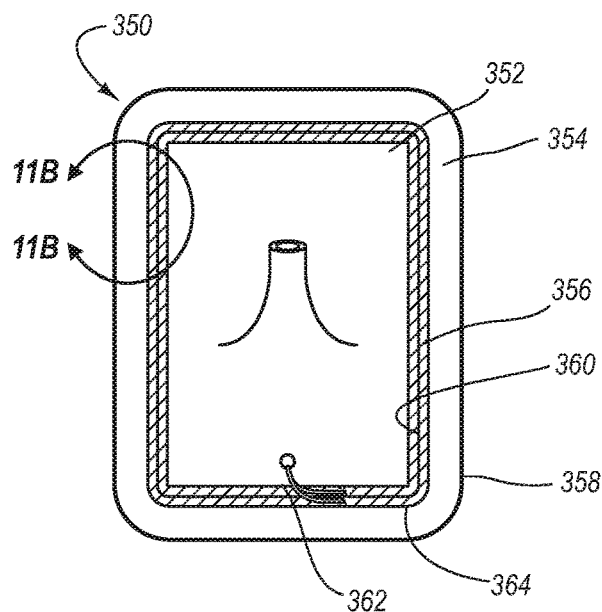
FIGS. 11A-11C include various views of an embodiment of a modular barrier device that includes decouplable members that can be separated from each other.
Figure 11B:
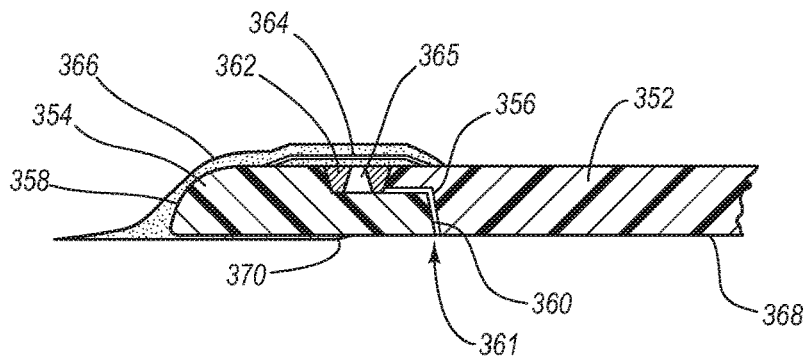
Figure 11C:
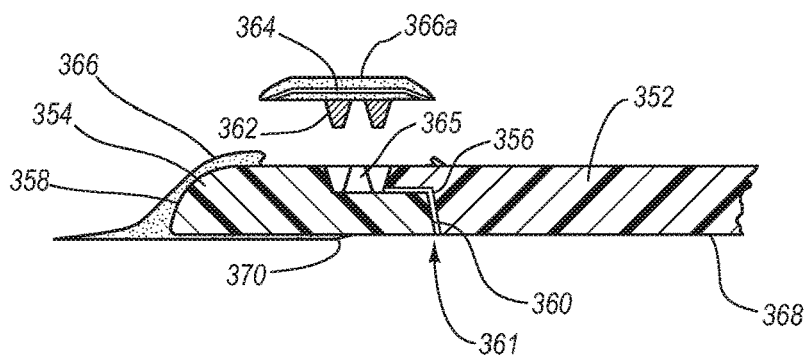

FIGS. 11A-11C illustrate another embodiment of a modular barrier device 350. The modular barrier device 350 can include a main barrier 352 and a perimeter barrier 354. The main barrier 352 can be configured as any barrier device as described herein. The perimeter barrier 354 is sized so as to be coupled/couplable to the perimeter surface 356 of the main barrier 352. For example, the perimeter barrier 354 can include an outer perimeter surface 358 and an inner perimeter surface 360 that is shaped and sized to conform with the perimeter surface 356 of the main barrier 352. When the main barrier 352 and perimeter barrier 354 are placed together so as to form the modular barrier device 350, the perimeter surface 356 forms a gap 361 with the inner perimeter surface 360 of the perimeter barrier 354. A release member 362, such as a wire, membrane, zip-lock members, or the like, can be imbedded on, within, at, or adjacent to the gap 361, such that pulling the release member 362 allows for the main barrier 352 to be decoupled from the perimeter barrier 354. As shown, the release member 362 is disposed within a junction 365 that extends around inner perimeter surface 360 of the perimeter barrier 354; however, the release member 362 and junction 365 can be in or at the gap 361 as well as within the main barrier 352 proximal or adjacent to the perimeter surface 356 of the main barrier 352. A cover member 364 can be disposed over or integrated with the release member 362 and junction 365 so as to keep the release member 360 disposed at the junction 365. The cover member 364 can be a material that is slit, cut, removed, lifted, or otherwise compromised such that pulling the release member 362 removes the cover member 364 and exposes junction 365 and gap 361. As shown, the cover member 364 is disposed over the perimeter surface 356 of the main barrier and inner perimeter surface 360 of the perimeter barrier 354.

FIG. 11B illustrates the modular barrier device 350 as applied to skin (not shown) with adhesive 366. The main barrier 352 includes a main base surface 368 that is shown to be disposed on the skin without adhesive; however, adhesive can be applied to the main base surface 368. The perimeter device 354 includes a perimeter base surface 370 which is shown to be affixed to the skin with adhesive 366. The adhesive 366 is shown to be on the perimeter base surface 370, outer perimeter surface 358 and over the gap 361.

FIG. 11C illustrates the modular barrier device 350 being removed from the skin. As shown, the release member 362 is pulled from the junction 365 so as to lift/detach the cover member 364 from the main barrier 352 and perimeter barrier 354 so as to cut, disrupt, separate, or otherwise remove the adhesive 366 from the device 350. This can expose the junction 365 and/or gap 311 so that main barrier 302 can be separated from the perimeter barrier 304 and pulled from the skin. For example, the release member can be configured similar to a zip lock, or releaseable cellophane membrane.

Figure 12A:
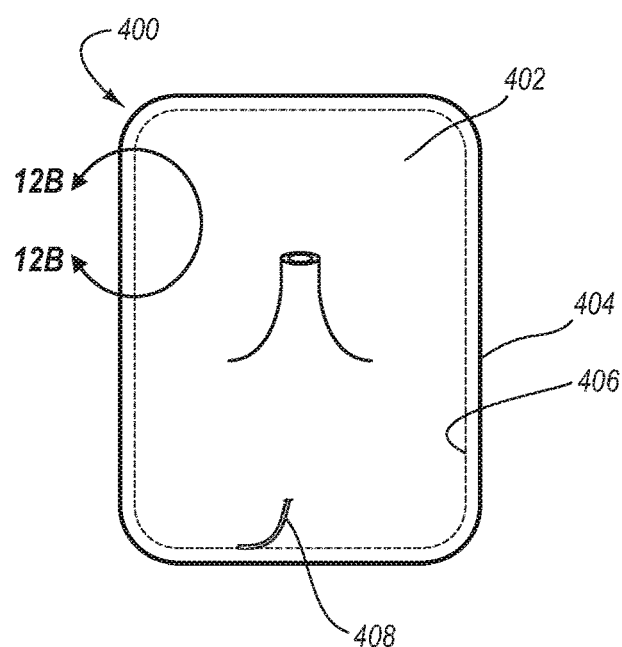
FIGS. 12A-12C include various views of an embodiment of a modular barrier device that includes decouplable members that can be separated by separation of a perforation.
Figure 12B:
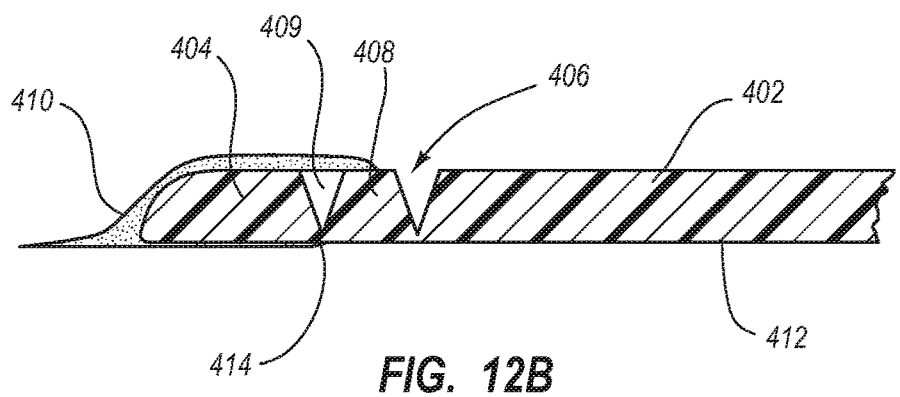
Figure 12C:
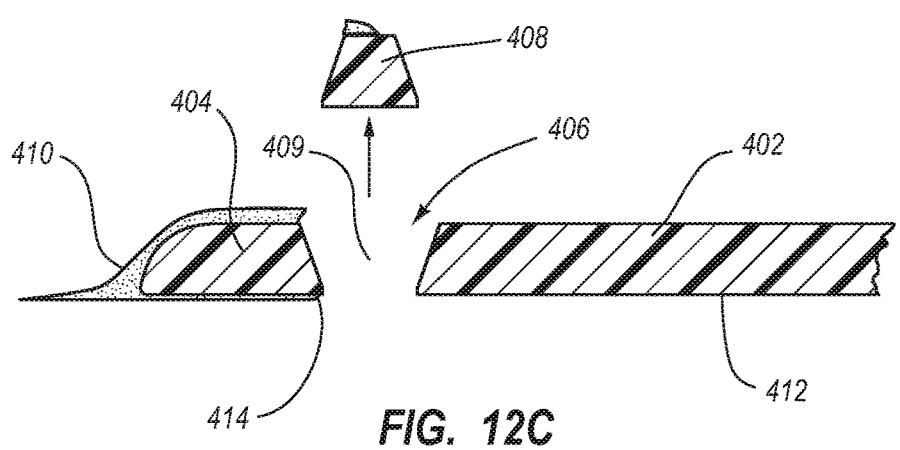

FIGS. 12A-12C illustrate an embodiment of a perforated barrier device 400. The perforated barrier device 400 has a perforation 406 that can be used to separate the main barrier 402 from a perimeter portion 404. The perforated barrier device 400 optionally may includes a rip member 408 that can be pulled to separate the main barrier 402 from the perimeter portion 404. The rip member 408 can be member that is pulled to split the perforation 406 or it can be an integrated member that separates at the perforation 406 when it is pulled from the device 400. Rip members 408 and perforation 406 are often found in food storage bags where the member can be ripped to open the bag.

FIG. 12B illustrates the perforated barrier device 400 as applied to skin (not shown) with adhesive 410. The main barrier 402 includes a main base surface 412 that is shown to be disposed on the skin without adhesive; however, adhesive can be applied to the main base surface 412. The perimeter portion 404 includes a perimeter base surface 414 which is shown to be affixed to the skin with adhesive 410. The perforation 406 is shown to include a rip member 408 that is coupled to the main barrier 402 and perimeter portion 404 such that removal or ripping of the rip member 408 opens the perforation 406. The perforation 406 also includes a plurality of perforation recesses 409 that allow for the rip member 408 to be easily removed. The perforation recesses 409 can be holes or any other perforation configuration.

In one embodiment, the barrier devices as described herein can be prepared as a series of nested barrier devices. This can include more than one barrier device being used in a series. Also, when configured as nested barrier devices, an antimicrobial composition can be disposed between the nested barrier devices or on any surface of the nested barrier devices.

The barrier devices as shown and described herein can include various features or configurations of any of the other barrier devices. As such, a feature or configuration of one depicted barrier device can be included on another embodiment of a barrier device that is shown in a different figure. Thus, the features of the barrier devices are interchangeable and can be used together as desired.

II. Aperture Barrier Device

It will be understood that one or more components or features of the embodiments of barrier devices disclosed herein may be combined with one or more other embodiments of barrier devices disclosed herein.

Figure 13A:
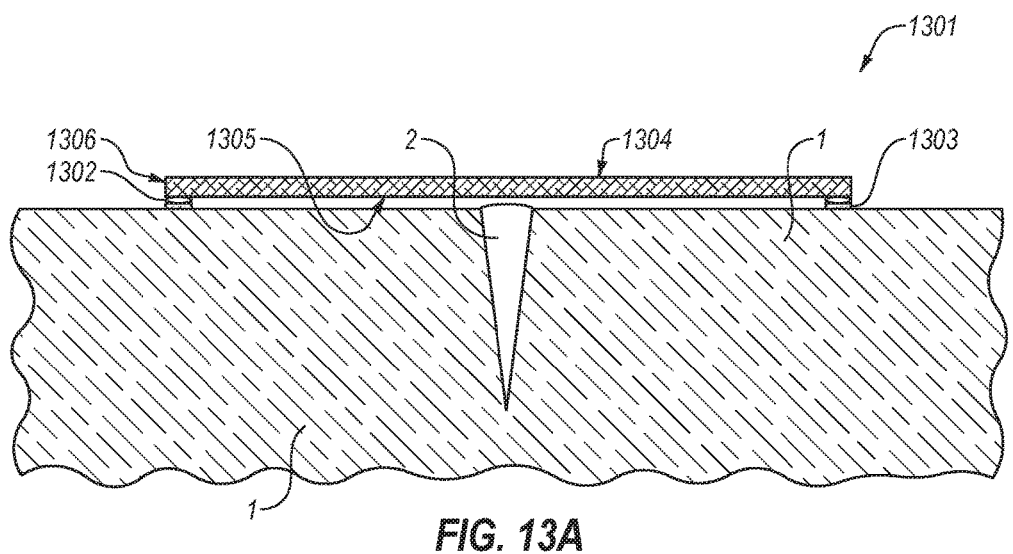
FIGS. 13A-13B illustrate cross-sectional views of an embodiment of a barrier device including an inflatable bladder disposed on a bottom surface of the device.
Figure 13B:
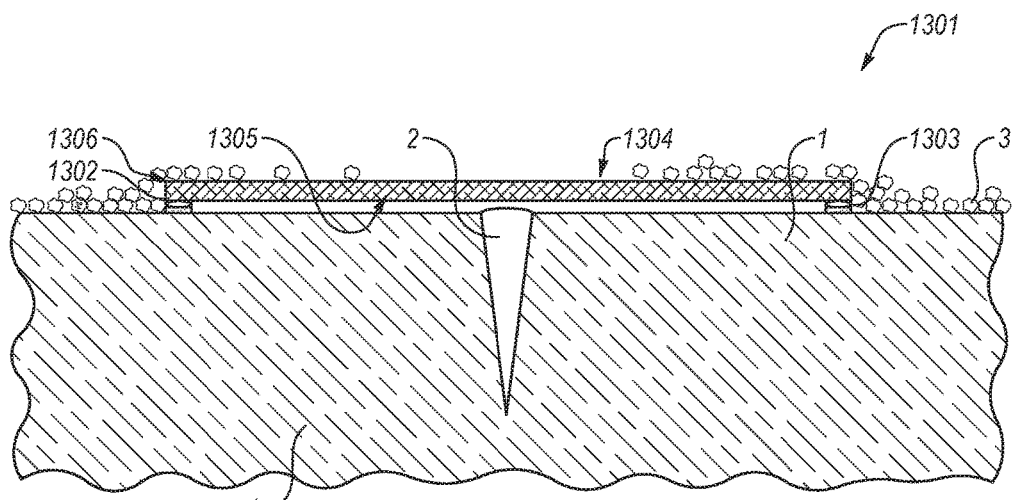
Figure 13C:
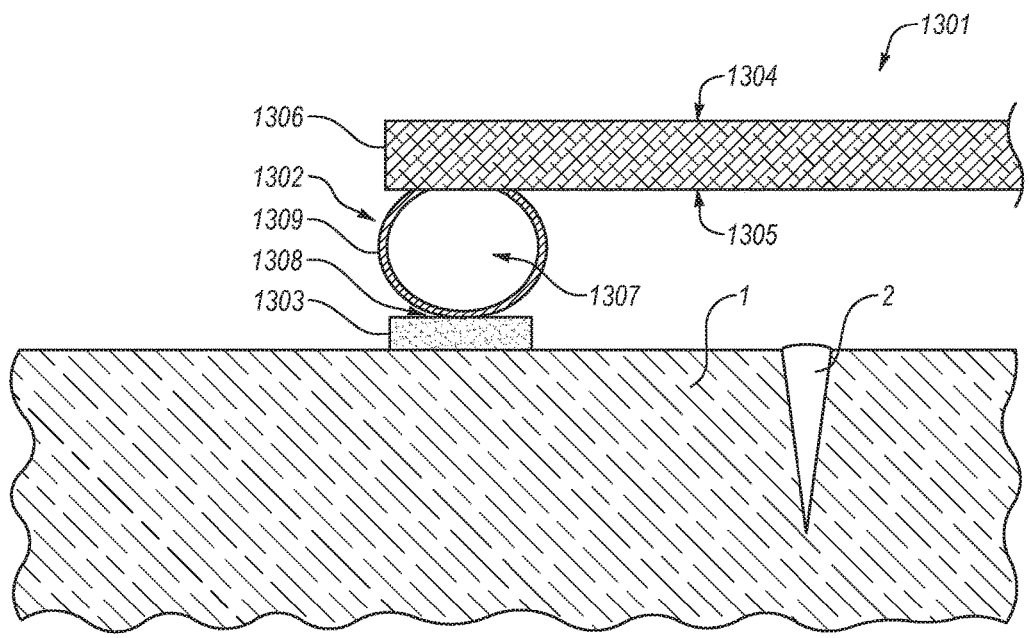
FIG. 13C illustrates a partial cross-sectional view of an embodiment of a barrier device where a bladder disposed on the bottom surface of the device is inflated.

Referring generally to FIG. 13A-C, FIG. 13A illustrates an embodiment of a barrier device 1301 that includes one or more expandable bladders 1302. In the illustrated embodiment, the bladder 1302 is shown to be disposed on a bottom surface 1305 of the barrier device 1301. As shown, the bladder 1302 may be positioned adjacent to and/or around a perimeter edge 1306 of the barrier device 1301. In other embodiments, the bladder 1302 may be disposed further away from the perimeter edge 1306 on the bottom surface 1305 of the barrier device 1301.

In one embodiment, the bladder 1302 may be disposed at the perimeter edge 1306, as shown in FIG. 13C. In various embodiments, the distance of the bladder 1302 from the perimeter edge 1306 on the bottom surface 1305 may vary. For example, a bladder 1302 may extend about the barrier device 1301 while the bladder 1302 may vary in location with respect to the perimeter edge 1306 about a perimeter of the barrier device 1301. In other words, a bladder 1302 may be disposed at the perimeter edge 1306 for at least a portion of the perimeter of the barrier device 1301, may be disposed on the bottom surface 1305 of the barrier device 1301 adjacent the perimeter edge 1306 for at least a portion of the perimeter of the barrier device 1301, may be disposed on the bottom surface 1305 of the barrier device 1301 offset from the perimeter edge 1306 for at least a portion of the perimeter of the barrier device 1301, may be otherwise located, or combinations thereof.

Also, multiple bladders 1302 may be disposed on the barrier device 1301. For example, a first bladder 1302 may be disposed at the perimeter edge 1306 of the barrier device 1301 and a second bladder 1302 may be disposed on the bottom surface 1305 adjacent to the perimeter edge 1306.

Also, for example, a first bladder 1302 may be disposed on the bottom surface 1305 adjacent to the perimeter edge 1306 and a second bladder 1302 may be disposed on the bottom surface 1305 further away from the perimeter edge 1306. In one embodiment, the first bladder 1302 may extend about the perimeter edge 1306 for only a portion of the perimeter of the barrier device 1301 and the second bladder 1302 may be disposed on the bottom surface 1305 and extend about the remaining portion of the perimeter of the barrier device 1301. Thus, a first bladder 1302 may extend around the entire perimeter of the barrier device 1301 at a first location, the first bladder 1302 may extend around a first portion of the perimeter of the barrier device 1301 at the first location, a second bladder 1302 may extend around the entire perimeter of the barrier device 1301 at a second location, the second bladder 1302 may extend around a second portion of the barrier device 1301 at the second location, or combinations thereof, where the first portion and the second portions may at least partially abut, at least partially overlap, or combinations thereof. In some embodiments of a barrier device 1301, one or more bladders 1302 may be disposed in such a way so that a barrier (e.g., completely enclosed) is created around an aperture 2 (e.g., a surgical cut, a wound, or other apertures).

In one embodiment, the bladder 1302 may vary along its length. For example, the bladder 1302 may vary in cross sectional shape, wall thickness, size, or combinations thereof. In some embodiments, the bladder 1302 may be manufactured separately from the barrier device 1301 and subsequently fixed to the barrier device 1301. In some embodiments, the bladder 1302 may be manufactured and/or molded in conjunction with the barrier device 1301 as a single piece.

An adhesive composition 1303 may adhere the barrier device to the skin 1 of a patient. For example, the adhesive composition 1303 may be applied to a surface of the bladder 1302 (e.g., a bottom-most surface) and the barrier device 1301 may be placed on the skin 1 of a patient to cover an aperture 2 (e.g., a surgical opening, a wound, or other aperture). In one embodiment, shown in FIG. 13A, the adhesive composition 1303 has been applied only to the bladder 1302 so that only the bladder 1302 binds to the skin 1. In one embodiment, the adhesive composition 1303 may be first applied to the bladder 1302 and subsequently adhered to the skin 1. In another embodiment of the barrier device 1301, the adhesive composition 1303 may first be applied directly to the skin 1 of a patient. For example, the adhesive composition 1303 may first be applied to the skin 1 of a patient around an aperture 2 and the barrier device 1301 may then be placed onto the skin 1 so that the bladder 1302 makes contact with the adhesive composition 1303 on the skin 1. In yet another embodiment, the bladder 1302 may be separate from the barrier device 1301. In this embodiment, the bladder 1302 may first be adhered to the skin 1, and the barrier device 1301 may subsequently be adhered to the bladder 1302. The adhesive composition 1303 may include one or more adhesive compositions described herein.

The bladder 1302 of the embodiment illustrated in FIG. 13A is shown as being deflated. The bladder 1302 may remain deflated until the barrier device 1301 is to be removed from the skin 1. A fluid (e.g., liquid or gas) may be injected into an inner chamber 1307 (shown in FIG. 13C) of the bladder 1302 through a port to at least partially inflate the bladder 1302. Examples of fluids may include saline, water, polyethylene glycol, atmospheric air, nitrogen, xenon, self-expanding foam, liquid-particulate mixtures, or other biocompatible, medically suitable fluids. Partially inflating the bladder 1302 may facilitate removal of the barrier device 1301, as described herein.

Figure 14:
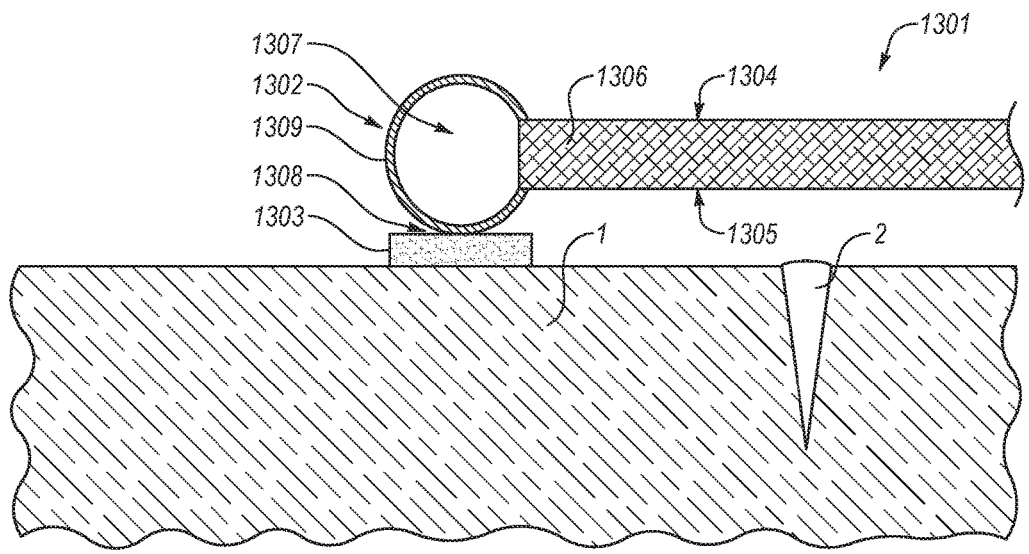
FIG. 14 illustrates a partial cross-sectional view of an embodiment of a barrier device where a bladder disposed at a perimeter edge of the barrier device is inflated.

A port is not shown in FIGS. 13A-14, but may include, for example, a puncture hole from a hypodermic needle or other fluid injector. In the embodiments of the barrier device 1301 illustrated in FIGS. 13A-14, the inner chambers 1307 of multiple bladders 1302 may each be accessed by a single port. In other embodiments, each inner chamber 1307 of one or more bladders 1302 may be accessed independently by multiple ports. Other embodiments of ports are illustrated in FIGS. 15A-16A and described in more detail below.

Inflation of the bladder 1302 increases the surface area of the bladder 1302. This expansion may create a stress at an interface 1308 between the bladder 1302 and the adhesive composition 1303 as the adhesive composition 1303 may not expand as much as the bladder 1302. The expansion of the bladder 1302 may weaken a bond between the bladder 1302 and the adhesive composition 1303.

Figure 22A:
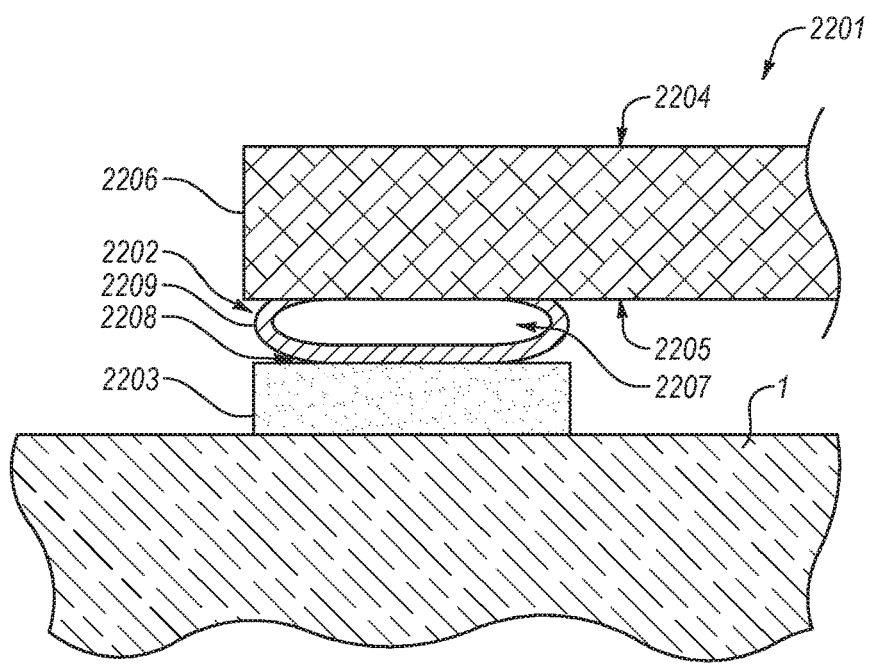
FIG. 22A illustrates a partial cross-sectional view of an embodiment of a tensioning anchor wherein an uninflated bladder is disposed on a bottom surface of the tensioning anchor.
Figure 22B:
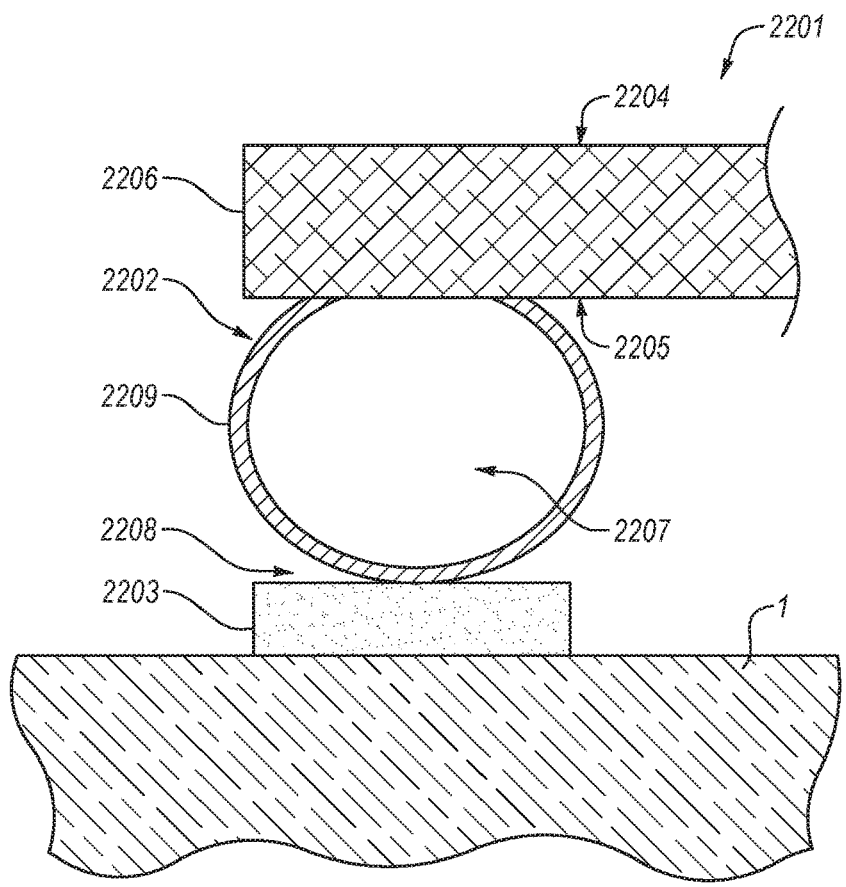
FIG. 22B illustrates a partial cross-sectional view of an embodiment of a tensioning anchor wherein an inflated bladder is disposed on a bottom surface of the tensioning anchor.

FIGS. 22A and 22B are illustrative of how inflating the bladder 2202 weakens the bond between the bladder 2202 and the adhesive composition 2203. FIG. 22A illustrates an embodiment of a bladder 2202 similar to the bladder 1302 illustrated in FIG. 13B, but where the bladder 2202 has been deflated. The interface 2208 (e.g., area where the bladder 2202 and the adhesive composition abut) between the bladder 2202 and the adhesive composition 2203 is greater than the interface 2208 between an inflated bladder 2202 and the adhesive composition 2203, such as the interface 2208 shown in FIG. 22B. In other words, the surface area of the bladder 2202 that is in contact with the adhesive composition 2203 is greater in FIG. 22A than it is in FIG. 22B. Also, the circumference of the bladder 2202 is greater when inflated, as illustrated in FIG. 22B. Therefore, an inflated bladder 1302 puts a stress at the bladder-adhesive interface 1308 by increasing the perimeter of the bladder 1302, while the adhesive composition 1303 may be more resistant to expansion. This stress at the bladder-adhesive interface 1308 results in portions of the bladder 1302 breaking free from portions of the adhesive composition 1303. As a result, the surface area of the bladder 1302, which is bonded to the adhesive composition 1303, may be reduced when inflated.

In one embodiment, the inflated bladder 1302 may completely detach from the adhesive composition 1303. In another embodiment, the inflated bladder 1302 may only partially detach from the adhesive composition 1303. In one embodiment, once the bond between the bladder 1302 and the adhesive composition 1303 has been weakened, the barrier device 1301 may be more easily removed, while reducing the incidences of injury to the skin 1. For example, with a reduced interface 1308, forces applied by the bladder 1302 to the adhesive composition 1303 may be smaller than forces applied by the skin 1 to the adhesive composition 1303. Thus, the adhesive composition 1303 may remain on the skin 1 rather than the bladder 1302. In one embodiment, portions of the bladder 1302 may tear off and remain attached to the adhesive composition 1303 upon removal of the barrier device 1301. A portion of the adhesive composition 1303 may remain on the skin 1 and slough off over time as the outer layer of skin 1 desquamates (i.e., the outer layer of dead skin flakes or peels off).

FIG. 13B illustrates the embodiment of a barrier device 1301 on the skin 1 of a patient surrounding an aperture 2. In the illustrated embodiment, the adhesive composition 1303 adheres the barrier device 1301 to the skin 1, enclosing the aperture 2 underneath the barrier device 1301. The barrier device 1301 may reduce incidences of infection at or in an aperture 2 (e.g. a wound or incision). In one embodiment, once the barrier device 1301 has been adhered to the skin 1 of a patient, bacteria 3, viruses, prions, or toxic chemicals cannot penetrate the barrier device 1301 and gain access to the aperture 2. In another embodiment, the barrier device 1301 may be gas impermeable. In yet another embodiment, the barrier device 1301 may be liquid impermeable. In yet another embodiment, the barrier device 1301 blocks access to the aperture 2 for any unwanted matter.

FIG. 13C is a zoomed in illustration of an embodiment where a bladder 1302 has been inflated. In the illustrated embodiment, the bladder 1302 is configured to remain attached to the bottom surface 1305 of the barrier device 1301 upon inflation. The bladder 1302 may also be disposed at the perimeter edge 1306 of the device, as shown in FIG. 14. The bladder 1302 may be made of any medically acceptable material capable of expansion, and which is impermeable to a fluid used to inflate it. For example, the bladder may be made of plastics, rubbers, nitrile, polyurethanes, polyethylenes, ethylene propylene diene monomer (EPDM), vinyl, silicone elastomers, neoprene, or combinations thereof.

Figure 15A:
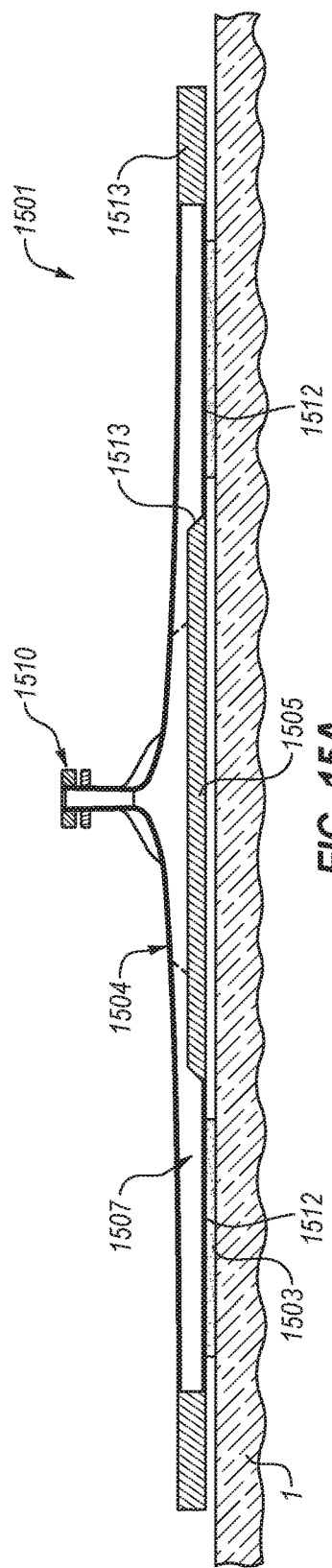
FIG. 15A illustrates a cross-sectional view of an embodiment of a barrier device.
Figure 15B:
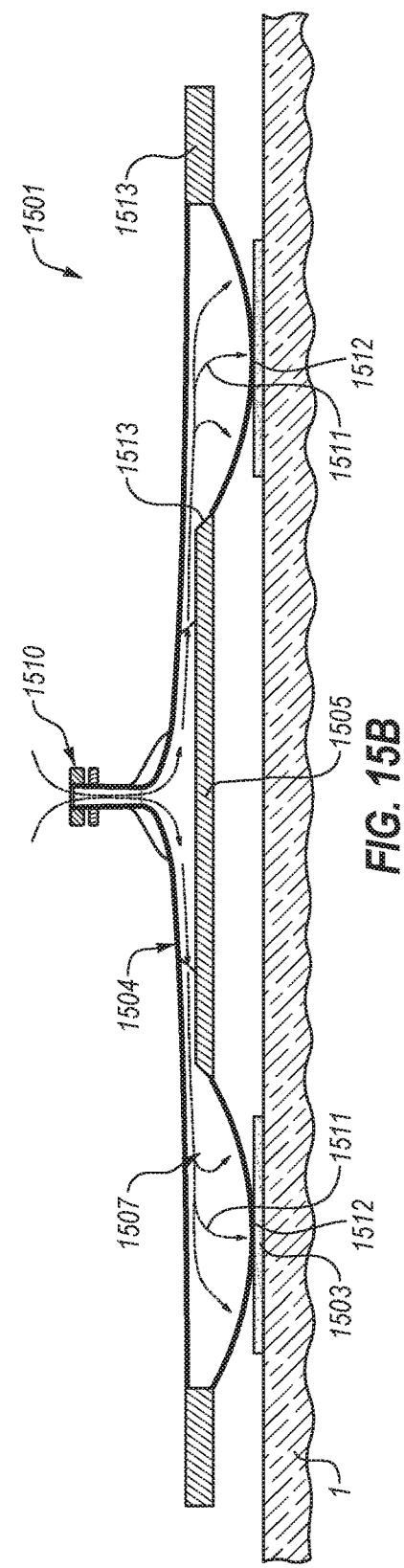
FIG. 15B illustrates a cross-sectional view of an embodiment of a barrier device where portions of a bottom layer of the device are expanded.

In the illustrated embodiments of FIGS. 13C and 14, a fluid may be injected into the inner chamber 1307, 1407 of the bladder 1302, 1402 to inflate the bladder 1302, 1402 either through the bladder wall 1309, 1409 or via the barrier device 1301, 1401. For example, a hypodermic needle may puncture the bladder wall 1309, 1409 and inject a fluid directly into the inner chamber 1307, 1407, the puncture hole acting as a port. Alternatively, the inner chamber 1307, 1407 of the bladder 1302, 1402 may be in fluid communication with an inner chamber (not shown) of the barrier device 1301, 1401. An inner chamber of a barrier device 1301, 1401 may be similar to the inner chamber 1507 of an embodiment illustrated on FIGS. 15A and 15B. In this way, a fluid may be injected through a port 1510, located on a top layer 1504 of the barrier device 1501, as shown in FIGS. 15A and 15B, and into the inner chamber 1307, 1407 of the bladder 1302, 1402 shown in FIGS. 13A-14. In yet another example, a port, such as the port 1510 illustrated in FIGS. 15A and 15B, may be attached directly to the bladder 1302, 1402. The ports described herein may include a one-way valve, such that, for example, fluid may be introduced into the port without being able to exit the port. For instance, a one-way valve may be placed just below the port. In at least one embodiment, this would allow the use of a smaller syringe to fill a bladder with a volume larger than that of the syringe or other fluid-delivery device.

Certain portions of the bladder 1302 may expand more or less than others depending on the thickness of the bladder wall 1309. For example, a bottom portion of the bladder wall 1309 in contact with the adhesive composition 1303 at the bladder-adhesive interface 1308 may be thinner than the rest of the bladder wall 1309. This may result in the portion of the bladder 1302 at the bladder-adhesive interface 1308 expanding more than the rest of the bladder 1302. These portions of the bladder 1302, which are in contact with the adhesive composition 1303, may be more prone to expand upon inflation. This may more efficiently weaken a bond between the bladder and the bladder 1032 and adhesive composition 1303.

Providing embodiments of the barrier device 1301, wherein the bladder wall 1309 has thin portions, is merely one method to enable certain areas of the bladder 1302 to expand more than others. Embodiments including bladders 1302 that have a constant wall thickness may still expand upon inflation and weaken a bond between the bladder and the adhesive. Expansion of the bladder 1302 may be done using a hypodermic needle to puncture the bladder 1302 and introduce a fluid into the inner chamber 1307. A port 1510, such as a Luer lock connection, may also be used to introduce a fluid 1511 into the inner chamber 1307, 1507, as shown in FIGS. 15A-16A and described in detail below. Any other connection through which a fluid 1511 may be introduced into an inner chamber 1307, 1507 of the barrier device may be used. Once a bond between the bladder 1302 and the adhesive composition 1303 is weakened, the barrier device 1301 may be more easily removed.

In other embodiments, such as those illustrated in FIGS. 15A-B, an inner chamber 1507 may be enclosed between, and/or at least partially defined by, top and bottom layers 1504, 1505 of the barrier device 1501. The top layer 1504 may be made of materials of other embodiments of barrier devices described herein. The bottom layer 1505 of the barrier device 1501 may have compliant portions 1512. The compliant portions 1512 and bottom layer 1505 may be made of any medically acceptable elastic or plastic material capable of expansion, and which is impermeable to a fluid used to inflate it. For example, the compliant portions 1512 and bottom layer 1505 may be made of plastics, rubbers, nitrile, polyurethanes, polyethylenes, ethylene propylene diene monomer (EPDM), vinyl, silicone elastomers, neoprene, or combinations thereof.

In the embodiment of the barrier device 1501 illustrated in FIGS. 15A-B, a single inner chamber 1507 is partially defined by the entire bottom layer 1505. In another embodiment, the barrier device 1501 may have multiple inner chambers 1507, which may each be partially defined by one or more distinct portions of the bottom layer 1505. In other embodiments, each inner chamber 1507 may be accessed independently by a port 1510. In other embodiments, a port 1510 may be a means for introducing a fluid into multiple inner chambers 1507 simultaneously.

It will be noted that other embodiments of the barrier device 1501 may include one or more components and/or features of other embodiments described herein. For example, one embodiment of a barrier device may include a combination of a bottom layer 1505 with compliant portions 1512 as well as one or more bladders 1302 disposed on a bottom surface of the bottom layer 1505. Other embodiments may include combinations of embodiments herein described where the number and configuration of ports, bladders 1302, compliant portions 1512, and top 1504 and bottom layers 1505 may vary.

The adhesive composition 1503 may be applied so that only the compliant portions 1512 of the bottom layer 1505 binds to the skin 1. In one embodiment, an adhesive composition 1503 may be first applied to the compliant portions 1512 and subsequently adhered to the skin 1. In another embodiment of the barrier device 1501, the adhesive composition 1503 may first be applied directly to the skin 1 of a patient. For example, the adhesive composition 1503 may first be applied to the skin 1 of a patient around an aperture. The barrier device 1501 may then be placed onto the skin 1 so that the compliant portions 1512 make contact with the adhesive composition 1503 on the skin 1. In yet another embodiment, the bottom layer 1505 may be separate from the top layer 1504. In this embodiment, the compliant portions 1512 of the bottom layer may first be adhered to the skin 1, and the top layer 1504 may subsequently be adhered to the bottom layer 1505. The adhesive composition 1503 may include one or more adhesive compositions described herein.

FIGS. 15A and 15B generally illustrate a barrier device having a top layer 1504 and a bottom layer 1505 joined at the perimeter edge of the barrier device 1501 to form an inner chamber 1507. In this embodiment, the port 1510 is a Luer lock connection, through which the inner chamber 1507 may be accessed. The port 1510 may be comprised of other connections that serve as means to introduce a fluid 1511 into the inner chamber 1507. A port may also include a puncture hole. For example, a hypodermic needle may puncture the barrier device 1501 or bladder 1302, wherein a fluid is introduced into the inner chamber 1507 through the needle.

The bottom layer 1505 of the barrier device 1501 shown in FIGS. 15A and 15B includes thick walled portions 1513 and thin walled portions 1512. The thickness of the thin walled portions 1512 may be from 0.01 mm to 2 mm. The thickness of the thick walled portions 1513 may be from 1 mm to 5 mm. An adhesive composition 1503 may be applied only to the thin walled portions 1512 of the bottom layer 1505. In this way, as illustrated in FIG. 15B, the thin walled portions 1512 may expand when a fluid 1511 is introduced into the inner chamber 1507 through a port 1510 before the thick walled portions 1313. The barrier device 1501 can be more easily removed upon expansion similar to the way that the expansion of the bladder 1302 shown in FIG. 13C facilitates removal of the barrier device 1301, as described above. The top layer 1504 of the embodiment illustrated in FIGS. 15A and 15B may be more rigid than the bottom layer 1505, or at least more rigid than the thin walled portions 1512 of the bottom layer 1505, so as to be more resistant to expansion upon the introduction of a fluid 1511 into the inner chamber 1507. In some embodiments, both the thin walled portions 1512 and the thick walled portions 1513 may expand.

Figure 16A:
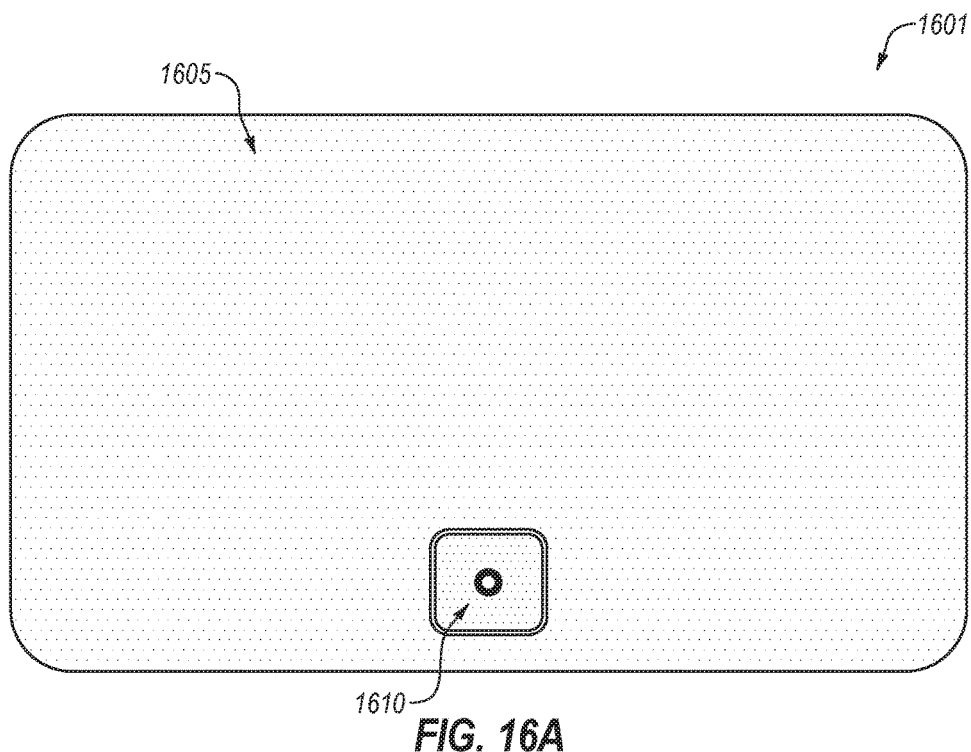
FIG. 16A illustrates a top view of an embodiment of a barrier device.
Figure 16B:
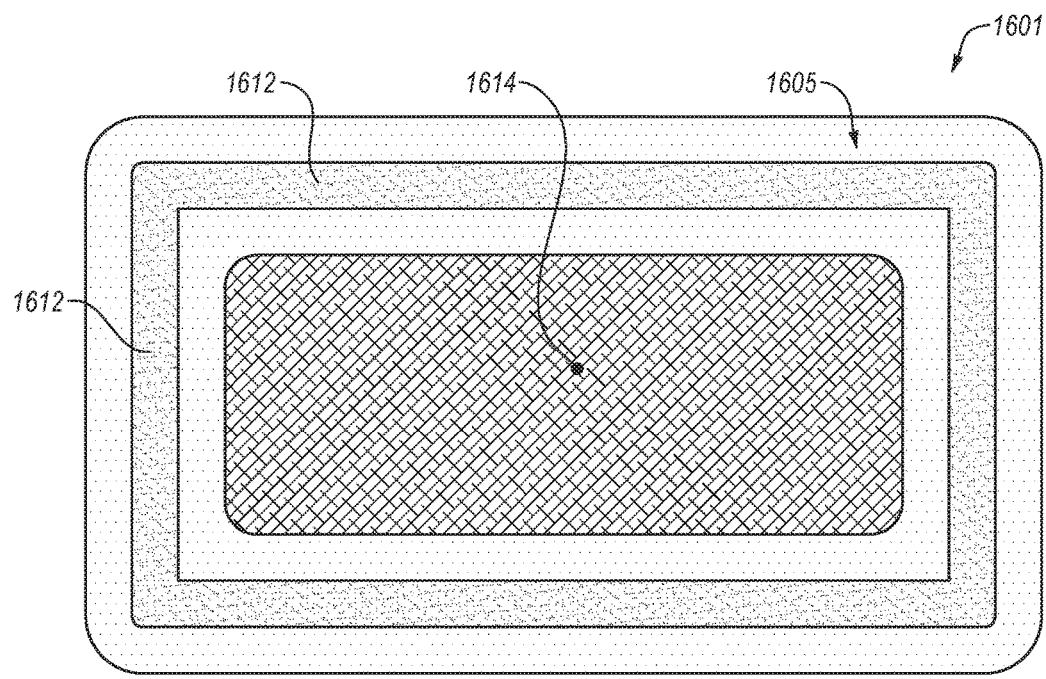
FIG. 16B illustrates a bottom view of an embodiment of a barrier device.

Referring generally to FIGS. 16A-B, FIG. 16A illustrates a top view of an embodiment of a barrier device 1601. In the illustrated embodiment, the barrier device 1601 is generally rectangular in shape. Other embodiments may be other shapes so as to cover a variety of apertures. For example, the barrier device 1601 may be circular, elliptical, polygonal, rectangular, otherwise shaped or a combinations thereof.

The barrier device 1601 may include a port 1610. The port 1610 may be accessed from a top layer 1604 of the barrier device. In the embodiment shown in FIG. 16A, the port 1610 is a Luer lock connection. In other embodiments, the port 1610 may be located directly on a bladder (not shown) or compliant portions 1612. In other embodiments, the port 1610 may be located on, or accessed from, different locations on the top and/or side of the barrier device 1601 other than the location of the port 1610 illustrated. Other embodiments, herein describing the location of one or more ports 1610 and/or compliant portions 1612 and/or bladders (not shown), may also be included.

Figure 17:
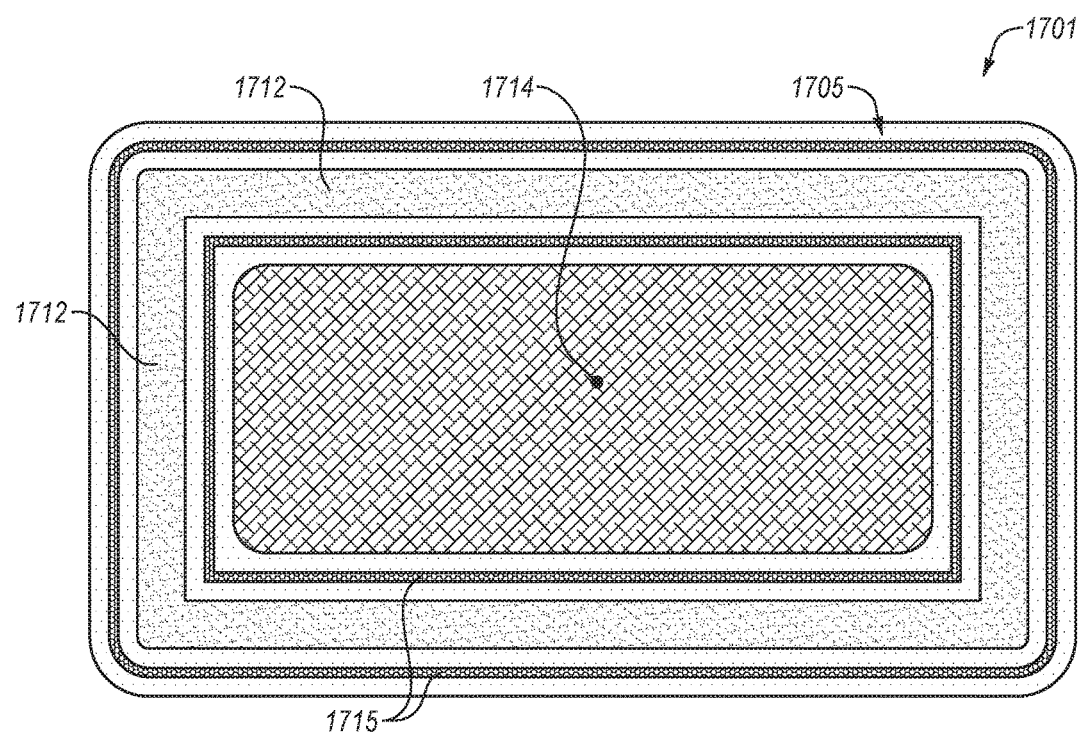
FIG. 17 illustrates a bottom view of an embodiment of a barrier device.

FIGS. 16B and 17 illustrate a bottom view of the bottom surface 1605, 1705 of various embodiments of a barrier device 1601, 1701. In the embodiment illustrated in FIG. 16B, an expandable portion 1612 may be disposed relative to the perimeter of the barrier device 1601. This expandable portion 1612 may be an inflatable bladder 1302, similar to the embodiments shown in FIGS. 13A-14. The expandable portion 1612 may also be a thin walled portion 1512 of the lower layer 1505 of the barrier device similar to the embodiment illustrated in FIGS. 15A and 15B and described herein.

As shown in FIG. 16B, the barrier device 1601 may include an absorptive material 1614. The absorptive material 1614 may be disposed within the perimeter of the expandable portion 1612. The absorptive material 1614 may be positioned so it overlies an aperture (e.g., a wound or surgical cut). The absorptive material 1614 is configured to absorb fluids that ooze from an aperture. Hydrogels and similar compounds may be utilized to absorb fluids. The absorptive material 1614 may contain antimicrobials or other wound healing co-factors. Antimicrobial compounds designed for elution may include, but are not limited to, chlorhexidine, silver ions, copper ions, rifampin, and minocycline.

FIG. 17 illustrates an embodiment of the barrier device similar to FIG. 16B, but where a pressure sensitive adhesive (PSA) 1715 is disposed on the bottom-most surface 1705 of the barrier device 1701. The PSA 1715 may assist in securing the barrier device 1701 onto the skin of a patient. In some embodiments, the use of PSA 1715 may facilitate the use of less adhesive composition (e.g., adhesive composition 1303) thus facilitating easier removal of the barrier device 1701 than embodiments where more adhesive composition is used. As shown in FIG. 17, the PSA 1715 may be disposed along the inside and outside perimeter of the expandable portion 1712 of the bottom surface 1705 of the device 1701. The PSA may be distributed anywhere on the bottom surface 1705 of the barrier device 1701. For example, the PSA 1715 may be disposed only within the expandable portion 1712 or only outside a perimeter of the expandable portion 1712. The PSA 1715 may also, for example, be disposed at the four corners of the bottom surface 1705 of the barrier device 1701. The configuration of the PSA 1715 on the bottom surface 1705 of the barrier device 1701 may depend on the shape and configuration of the barrier device 1701. One may appreciate, in light of the current specification, that the PSA 1715 may be disposed on any portion of the barrier device 1701. In some embodiments, the PSA 1715 may be disposed on a portion of the expandable portion 1712, but at least a portion of the expandable portion 1712 must include adhesive composition.

Adhesive composition may be applied to the expandable portions 1612, 1712 on the bottom surfaces 1605, 1705 of the barrier devices 1501, 1601, 1701 illustrated in FIGS. 15A-17 in order to adhere the barrier device 1501, 1601, 1701 to the skin 1 of a patient. The expandable portions 1512, 1612, 1712 may completely enclose an aperture beneath the barrier device 1501, 1601, 1701 within a closed perimeter of the expandable portion 1512, 1612, 1712. The adhesive composition 1503 may include one or more adhesive compositions described herein.

Figure 18A:
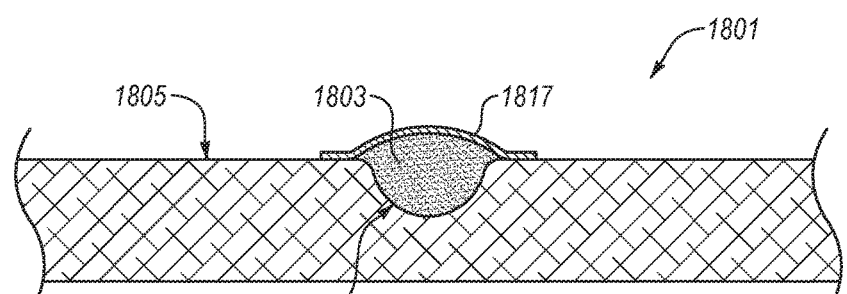
FIGS. 18A-18B illustrate various views of an embodiment of a barrier device wherein an adhesive composition is sealed within a groove with a seal.
Figure 18B:
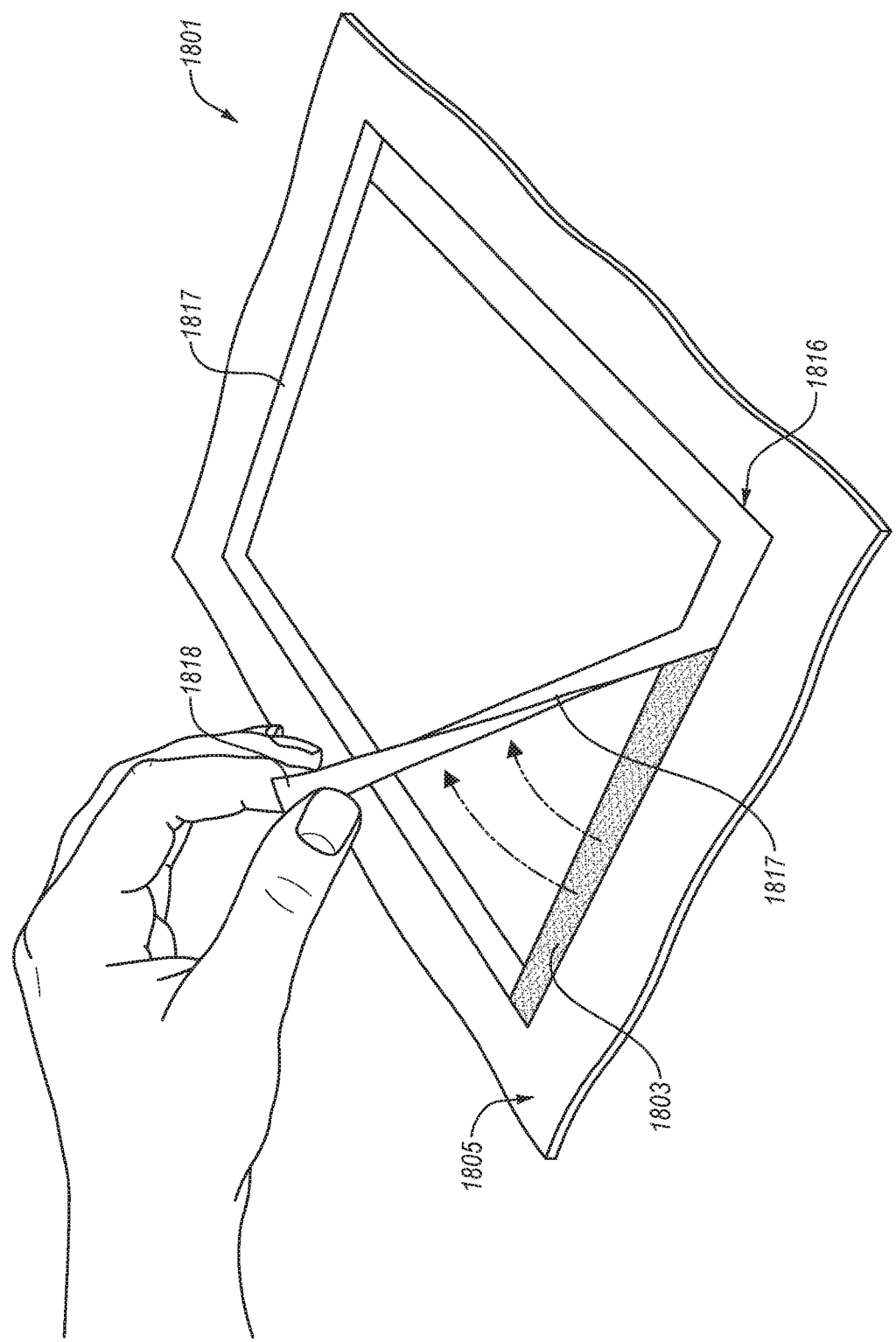

In some embodiments, an adhesive composition may be pre-applied to a barrier device and enclosed until use. As shown in FIGS. 18A and 18B illustrate, an embodiment of a barrier device 1801 may include an adhesive composition 1803 that resides in a groove 1816 in the bottom surface 1805 of the barrier device 1801. A seal 1817 may span the adhesive composition 1803 and/or the groove 1816 and may seal the adhesive composition 1803 (e.g., within the groove 1816). The adhesive composition 1803 and the seal 1817 may be placed on or in the barrier device 1801 during the manufacturing of the barrier device 1801. The seal 1817 may prevent the adhesive composition 1803 from exposure to air, thus preventing polymerization, until the seal is removed and/or the barrier device 1801 is adhered to a surface. The adhesive composition 1803 may be released to make contact with the skin 1 of a patient and adhere the barrier device 1801 to the skin 1 upon a removal of the seal 1817.

FIG. 18B illustrates an embodiment of an easy-release seal 1817. A seal 1817 may include a pull tab 1818 to make a removal of the seal easier. For example, a person removing the seal 1817 may grab the pull tab 1818 and remove the seal 1817 by pulling it away from the barrier device 1801. Once the seal 1817 is removed and the adhesive composition 1803 is exposed to air, the adhesive composition 1803 may have a window of time before it polymerizes. The barrier device 1801 may be positioned on the skin of a patient within this window of time. That is, after the removal of the seal 1817 but prior to polymerization of the adhesive composition 1803. It will be appreciated in light of the current disclosure that the embodiment shown in FIGS. 18A and 18B, including an adhesive composition 1803 residing in a groove 1816 and covered by a removable seal 1817, may be utilized in any other embodiment described herein. For example, the embodiments illustrated in FIGS. 13A-17 may all be comprised of an adhesive composition 1803 covered by a removable seal 1817. In some embodiments, a groove 1816 may be disposed on the bottom surface 1805 of the barrier device 1801 to correspond with the location of the compliant portions 1712 or bladders 1302 of other embodiments herein described.

Figure 19:
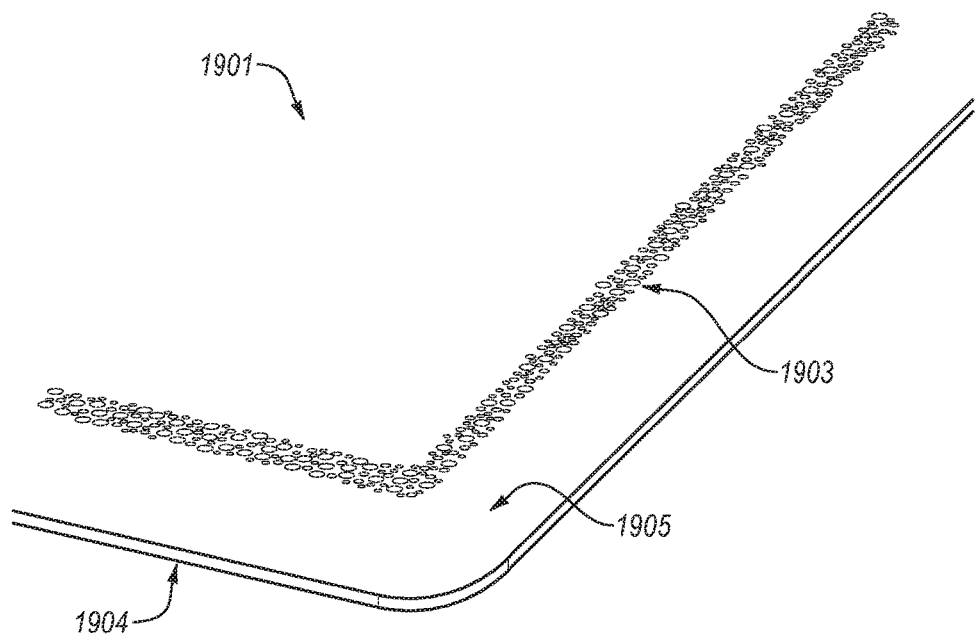
FIG. 19 illustrates a perspective view of an embodiment of a barrier device that includes an encapsulated adhesive composition disposed on a bottom surface of the device.

FIG. 19 illustrates an embodiment of a barrier device 1901 where the adhesive composition 1903 resides in a plurality of capsules on the bottom surface 1905 of the barrier device 1901. In the illustrated embodiment, the adhesive composition 1903 may, for example, be contained in microcapsules. The microencapsulated adhesive composition 1903 remains unexposed to air until the outer surface of the microcapsules is breached. A person applying the barrier device 1901 on the skin 1 of a patient may position the barrier device 1901 as desired then press down on the top surface 1904 of the barrier device above where the encapsulated adhesive composition 1903 is disposed underneath. Pressure applied to the capsules may cause a plurality of the capsules to open, thus releasing the adhesive composition 1903 and adhering the barrier device 1901 to a surface.

The capsules may be many different sizes and made of many different materials. Capsules may be made of starch, dextrins, sucrose, cellulose, chitosan, gums (arabic gum, alginate and carrageenan), lipids (wax, paraffin, monoglycerides and diglycerides, hydrogenated oils and fats), calcium sulfate, silicates and proteins (gluten, casein, gelatin and albumin), polyvinyl alcohol, or combinations thereof.

It will be appreciated in light of the current disclosure that the embodiment shown in FIG. 19, including an encapsulated adhesive composition 1903 may be utilized in any other embodiment described herein. For example, the embodiment illustrated in FIGS. 13A-17 may all be comprised of an encapsulated adhesive composition that releases the adhesive composition 1903 when a force or pressure is applied to the capsules. Furthermore, a combination of embodiments shown in FIGS. 18A-18B and FIG. 19 may also be provided. For example, the adhesive composition 1803 residing in the groove 1816 shown in the embodiment of the barrier device 1801 illustrated in FIGS. 18A-18B may be an encapsulated adhesive composition 1903 as illustrated in the embodiment of FIG. 19. Alternatively, the adhesive composition 1303 illustrated in FIGS. 13A-15B may comprise an encapsulated adhesive compound and/or reside in grooves 1816 and/or sealed by a seal 1817.

III. Wound Closure Tensioning Anchor

Figure 20A:
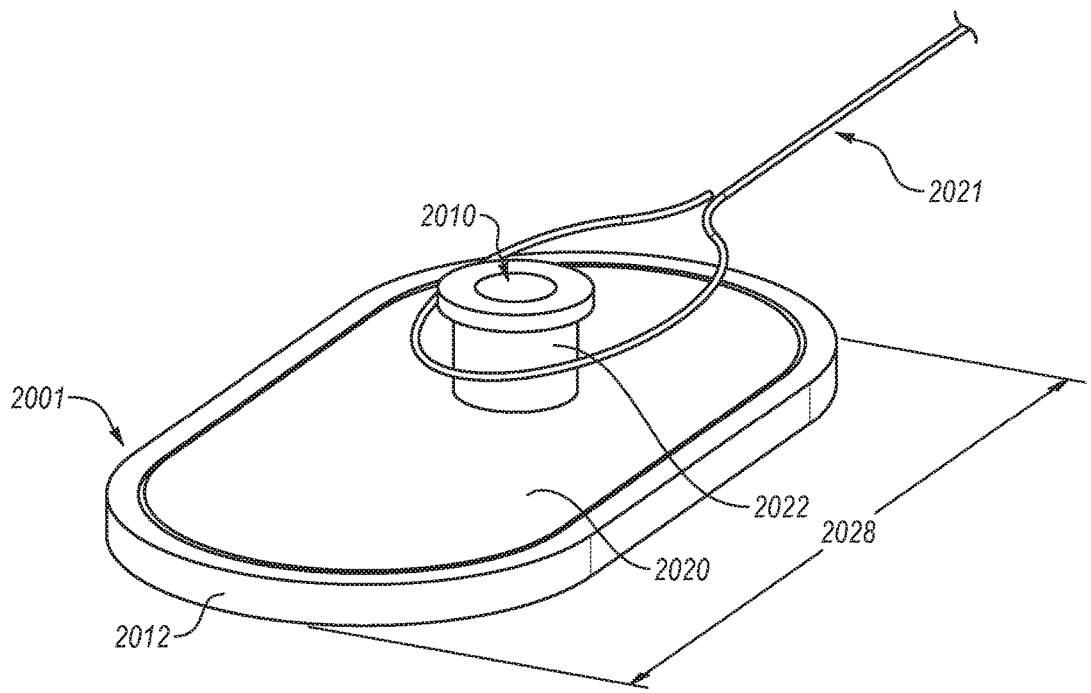
FIG. 20A illustrates a perspective view of an embodiment of a tensioning anchor.

An embodiment of a wound closure tensioning anchor 2001 is illustrated in FIG. 20A. The tensioning anchor 2001 includes a base member 2020, a receiving member 2022, and an expandable membrane 2012. In some embodiments the tensioning anchor 2001 may include a port 2010. As shown, the tensioning anchor 2001 may be used with a connecting member 2021. The base member 2020 and receiving member 2022 may be comprised any medically acceptable material. That is, any material that is used for a medical device may be used in preparing an anchor 2001 as described and shown herein. For example, the base member 2020 and/or receiving member 2022, may be prepared from rubbers, elastomers, bandage-like materials, cloths, fibrous materials, paper, porous materials, plastics, hard plastics, malleable plastics, polyethylenes, polystyrenes, foams, polyurethanes, latexes, and the like.

The base member 2020 illustrated in FIG. 20A is elliptical in shape. In other embodiments of the anchor 2001, the base member 2002 may be rectangular, polygonal, circular, otherwise shaped, or any combination of such shapes. Other embodiments of the base member 2020 may be irregularly shaped.

In FIG. 20A, the receiving member 2022 is shown as a cylindrical post extruded from the top of a base member 2020. In the illustrated embodiment, the connecting member 2021 may be secured to the receiving member 2022. The receiving member 2022 shown is one example of a receiving member, but the receiving member 2022 may be otherwise shaped. In at least one embodiment, the receiving member may be configured to receive a connecting member 2021 and limit movement of the connecting member 2021 relative to the connecting member 2021. In at least one embodiment, the receiving member 2022 may withstand a force exerted by the connecting member 2021 without failing. In some embodiments, the receiving member 2022 may be a pin or a hook. Alternatively, the receiving member 2022 may be formed in the base member 2020 such that the connecting member 2021 may be inserted and/or retained by the base member 2020.

The receiving member 2022 may be rigidly connected to a base member 2020 so as to transfer a force applied by a connecting member 2021 to the base member 2020 or anchor 2001 in general. As shown, the receiving member 2022 may include a retaining feature (not labeled) that may limit movement of a connecting member 2021 in at least one direction. For example, as shown, the retaining feature may limit vertical movement (e.g., away from a top surface of the anchor 2001) of the connecting member 2021.

In some embodiments, it may be desirable for receiving member 2022 to receive the connecting member 2021 as close to a bottom surface of the anchor 2001 as possible. Receiving a connecting member 2021 close to the bottom surface may minimize the moment of a force exerted by the connecting member 2021 on the receiving member 2022. For example, the further the distance from the bottom surface that the connecting member 2021 is connected, the larger the moment applied to the anchor 2001. Receiving the connecting member 2021 near the bottom surface may minimize these perpendicular forces (e.g., moments) and/or may transfer the force from the connecting member 2021 into a shear force spread out over the bottom surface of the anchor 2001. In one or more embodiments, the receiving member 2022 may receive the connecting member 2021 within a thickness of the base member 2020 or below the base member 2020.

For example, a ratio of a major dimension 2028 of the base member 2020 of the anchor 2001 to a distance above the skin where the connecting member 2021 is received may be less than three. In other words, the major dimension 2028 may be at least three times greater than a distance above the skin where the receiving member 2022 receives the connecting member 2021. In embodiments where the ratio of major dimension 2028 to height of the connecting member 2021 is less than 3, the base member 2020 may be large enough and/or stable enough to minimize the perpendicular forces applied to the skin by a lever arm of the receiving member 2022.

The receiving member 2022 is shown as not being centrally located in the base member 2020. The receiving member 2022 may be located closer to a front edge relative to the major dimension 2028. For example, the receiving member 2022 may be spaced one third of the major dimension 2028 from the front edge. Spacing the receiving member 2022 closer to the front edge may increase the ability of the base member 2020 to resist forces applied by the connecting member 2021.

As illustrated in FIG. 20A, the connecting member 2021 may be a wire. The wire may be made of any material suitable to sustain a desired force on the anchor 2001 without breaking, stretching, elongating, or otherwise failing. Such materials may include plastic, metal, fabric, yarn, thread, or the like. Although a more elastic material may be used, forces applied by the anchor 2001 may be more directly applied to the skin in embodiments with a connecting member 2021 that is more rigid than elastic.

Figure 20B:
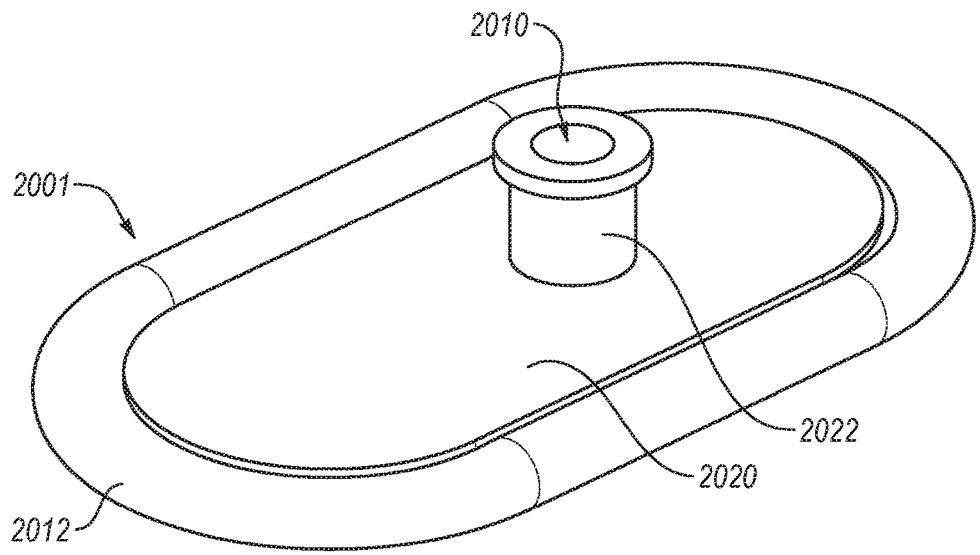
FIGS. 20B-20C illustrate various views of an embodiment of a tensioning anchor wherein an inflated bladder is disposed at a perimeter edge of the tensioning anchor.

FIGS. 20A and 20B illustrate an embodiment of an anchor 2001 where the expandable membrane 2012 is an inflatable bladder disposed around a perimeter edge of the base member 2020. The anchor 2001 may be adhered to the skin of a patient while the expandable membrane 2012 is deflated. An adhesive composition may be applied to a bottom surface of the expandable membrane 2012 configured to make contact with the skin. A fluid may enter an inner chamber (not shown) through the port 2010 in order to expand the expandable membrane 2012. When the expandable membrane 2012 expands, the surface area of the expandable membrane 2012 increases and a bond between the expandable membrane 2012 and the adhesive composition is weakened. The anchor 2001 can then be removed, in at least one embodiment, without tearing and/or injuring the skin. A more detailed description of the weakening of the bond between the expandable membrane 2012 and the adhesive composition is given below when referring to FIGS. 22A-B.

In FIGS. 20A and 20B, a port 2010 is located on the base member 2020. Fluid received into the port 2010 may travel to an inner chamber (not shown) of the expandable membrane 2012 through an inner chamber (not shown) within the base member 2020. In some embodiments, the port 2010 may be provided directly on the expandable membrane 2012 and/or it may be a puncture hole from a needle.

Figure 20C:
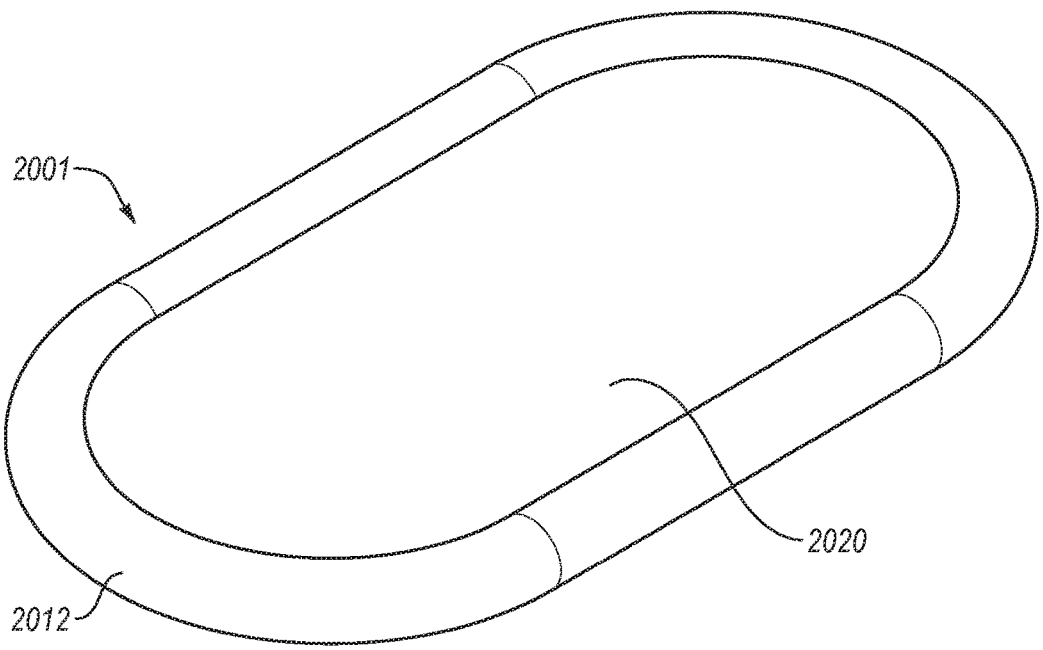

FIG. 20C illustrates an embodiment of an anchor 2001, similar to the anchor 2001 illustrated in FIG. 20A, but without a predefined port. For example, a hypodermic needle may directly pierce the expandable membrane 2012 to inject a fluid. Introducing a fluid into an inner chamber enclosed in the expandable membrane 2012 causes the expandable membrane 2012 to expand. The surface area of the expandable membrane 2012 increases upon expansion, weakening the bond between the adhesive composition and the expandable membrane 2012. The weakening of the bond between the adhesive composition and the expandable membrane 2012 is described in more detail below when referring to FIGS. 22A-B. Once this bond has been weakened, pulling the anchor 2001 away from the skin will remove it from the patient. Portions of the adhesive composition may remain on the skin and eventually slough off over time as the outer layer of skin desquamates.

A wall thickness of the expandable membrane 2012 illustrated in FIGS. 20A-20C (and in other embodiments described herein) may or may not be a constant. The expandable membrane 2012 may expand more where the wall is thinner. It may be advantageous to have thin walled portions of the expandable membrane 2012 where expansion is desired most. For example, the portion of the expandable membrane 2012 that makes contact with the skin, and where the adhesive composition is applied, may have a thinner wall thickness than the rest of the bladder. This may result in the greatest expansion occurring at areas of the expandable membrane 2012 where separation from the adhesive composition is most desired. That it, at an interface between the expandable membrane 2012 and the adhesive composition.

Figure 24:
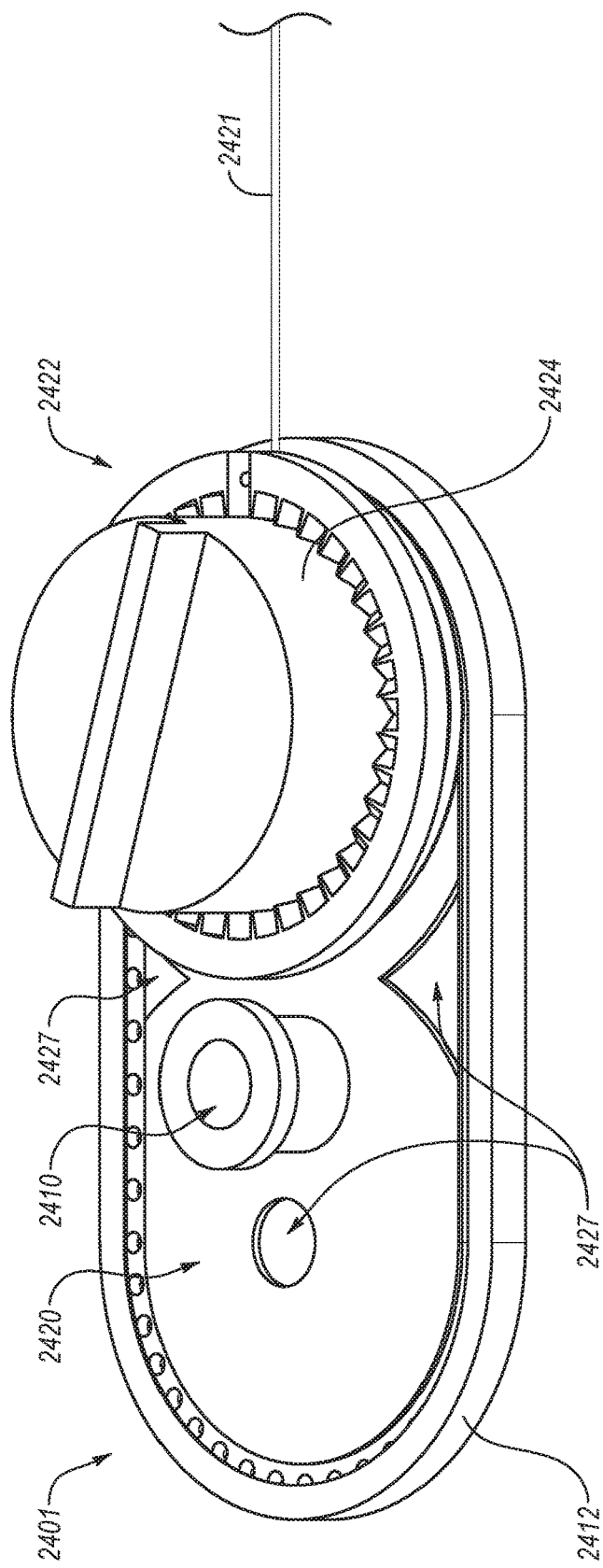
FIG. 24 illustrates a perspective view of an embodiment of a tensioning anchor that includes an adjustment mechanism.

FIGS. 20A and 20B illustrate an embodiment of an anchor 2001 with a port 2010. The port 2010 is configured to receive a fluid into an inner chamber (not shown). In the illustrated embodiment, the port 2010 is configured to receive a fluid through the receiving member 2022. The expandable membrane 2012 is a bladder disposed at the perimeter edge of the anchor 2001. The port 2010 may also be separate from the receiving member 2022 and located elsewhere on the base member 2020. For example, in some embodiments, the port 2010 may be separate from the receiving member 2022, as illustrated in FIG. 24 and described in more detail below. The port 2010 may also be located directly on the expandable membrane 2012 itself. For example, the port 2010 may also be a hypodermic needle puncture hole in the expandable membrane 2012. In the embodiment illustrated in FIG. 20A, the port 2010 is a Luer lock connection, enabling a syringe with a complimentary Luer connection to be attached. Other connections may be utilized that enable injection of a fluid through the port 2010. For example, the port 2010 may be a Luer connection located on the expandable membrane 2012. Also, for example, an inner chamber (not shown) of the expandable membrane may be in fluid communication with an inner chamber (not shown) of the base member 2020. In this way, fluid may be injected through the port 2010, located on the base member 2020, as illustrated in FIG. 20A, and into an inner chamber of the expandable membrane.

Figure 21:
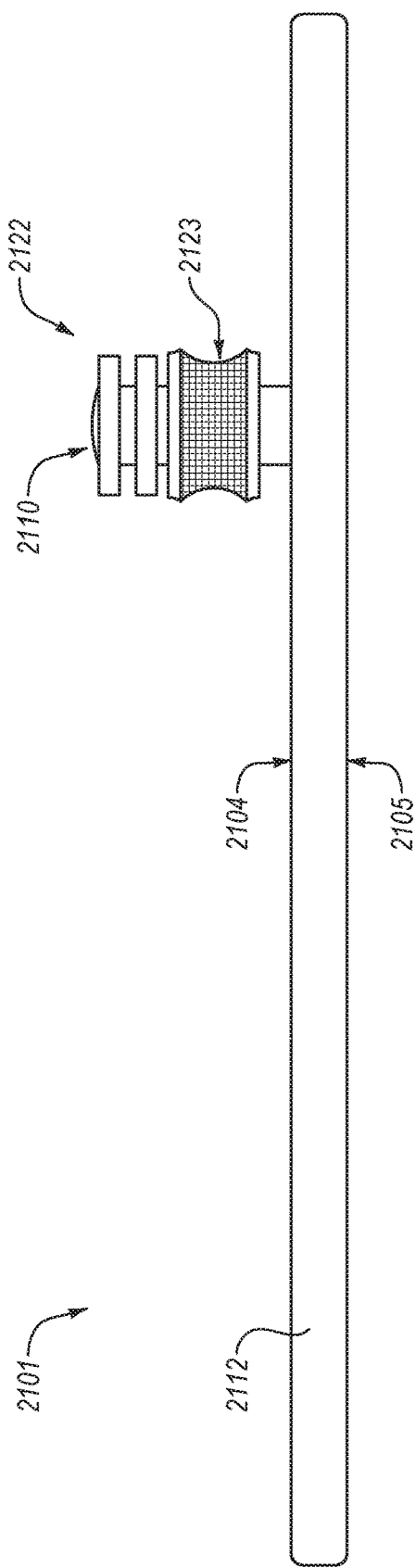
FIG. 21 illustrates a side view of an embodiment of a tensioning anchor.

A side view of an embodiment of a tensioning anchor 2101 is shown in FIG. 21. In the illustrated embodiment, a port 2110 is configured to receive a fluid through the receiving member 2122 located on the top surface 2104 of the base member 2120. A syringe or other inflation device may be connected to the port 2110 via, for example, a Luer lock connection.

The receiving member 2122 may include a pulley mechanism 2123 around which a connecting member 2121 may be wrapped and routed to another anchor 2101. For example, as shown FIG. 27, a single connecting member 2721 may be used to connect three or more anchors. In other words, an anchor may use a pulley mechanism 2123 to receive a connecting member that may be retained vertically and positionally, but which may still move along its length. In some embodiments, a pulley mechanism 2123 may reduce friction between the receiving member 2122 and the connecting member 2121.

An adhesive composition may be applied to the bottom surface 2105 of the anchor 2101 and the anchor 2101 may be adhered to the skin of a patient. The adhesive composition may be similar to the adhesive compositions described herein.

FIG. 22A is a zoomed in illustration of an embodiment of an anchor 2201 where the expandable membrane is a bladder 2202 disposed on the bottom surface 2205 of the anchor 2201 near or at the perimeter edge 2206 of the anchor 2201. The bladder 2202 may also be disposed at the perimeter edge 2206 of the device, similar to the configuration of a bladder on a barrier device illustrated in FIG. 14. The bladder 2202 is deflated in FIG. 22A and inflated in FIG. 22B. In the illustrated embodiment, the bladder 2202 is configured to remain attached to the bottom surface 2205 of the anchor 2201 upon inflation. In the illustrated embodiments of FIGS. 22A and 22B, fluid may be injected into the inner chamber 2207 of the bladder 2202 to inflate the bladder 2202 either through the bladder wall 2209 or via the anchor 2201. For example, a hypodermic needle may puncture the bladder wall 2209 and inject a fluid directly into the inner chamber 2207, the puncture hole acting as a port. Also, for example, the inner chamber 2207 of the bladder 2202 may be in fluid communication with an inner chamber (not shown) of the anchor 2201. In this way, a fluid may be injected through a port into the inner chamber 2207 of the bladder 2202. In yet another example, a port, such as the port 2010 illustrated in FIG. 20, may be attached directly to the bladder 2202.

In one embodiment, the bladder 2202 may be disposed at the perimeter edge 2206, as shown in FIGS. 22A-B. In one embodiment, the distance of the bladder 2202 from the perimeter edge 2206 on the bottom surface 2205 of the anchor 2201 may vary. Also, multiple bladders 2202 may be disposed on the anchor 2201. For example, a first bladder 2202 may be disposed at the perimeter edge 2206 of the anchor 2201 and a second bladder 2202 may be disposed on the bottom surface 2205 adjacent to the perimeter edge 2206. Also, for example, a first bladder 2202 may be disposed on the bottom surface 2205 adjacent to the perimeter edge 2206 and a second bladder 2202 may be disposed on the bottom surface 2205 further away from the perimeter edge 2206. In one embodiment, the cross-sectional dimensions of the bladder 2202 may vary. Other embodiments of an anchor 2201 and bladder 2202 configurations may include any combination of other embodiments herein described. The bladder 2202 may be manufactured separately from the anchor 2201 and subsequently fixed to the anchor 2201. Alternatively, the bladder 2202 may be manufactured and/or molded in conjunction with the anchor 2201 as a single piece.

Different portions of the bladder 2202 may expand more or less than others depending on the thickness of the bladder wall 2209. For example, a bottom portion of the bladder wall 2209 in contact with the adhesive composition 2203 at the bladder-adhesive interface 2208 may be thinner than the rest of the bladder wall 2209. This may cause the portion of the bladder 2202 at the bladder-adhesive interface 2208 to expand more than the rest of the bladder 2202. These portions of the bladder 2202, which are in contact with the adhesive composition 2203, may be more prone to expand upon inflation. This may more efficiently weaken a bond between the bladder and the adhesive.

The preceding examples of the anchor 2201, where the bladder wall 2209 has thin portions, is merely one method to enable certain areas of the bladder 2202 to expand more than others. Embodiments including bladders 2202 that have a constant wall thickness will still expand upon inflation and weaken a bond between the bladder 2202 and the adhesive composition 2203. Expansion of the bladder 2202 may be done using a hypodermic needle to puncture the bladder 2202 and introduce a fluid into the inner chamber 2207. A port 2110, such as a Luer lock connection illustrated in FIG. 21, may also be used to introduce a fluid into the inner chamber 2207. Any other connection through which a fluid may be introduced into the inner chamber 2207 of the bladder 2202 may be used. Once a bond between the bladder 2202 and the adhesive composition 2203 is weakened, the anchor 2201 may be more easily removed.

In the embodiment illustrated in FIG. 22A, an adhesive composition 2203 has been applied to only a bladder 2202 so that only the bladder 2202 adheres to the skin. This allows for removal of the anchor 2201 upon inflation of the bladder 2202. Inflation of the bladder 2202 increases the surface area of the bladder 2202, which puts a stress on the bladder-adhesive interface 2208, thus weakening a bond between the bladder 2202 and the adhesive composition 2203. The illustrated embodiment shows a bladder 2202 that is deflated, which may be appropriate during the application and/or use of the anchor 2201. A port is not shown in FIGS. 22A and 22B, but may include, for example, a puncture hole from a hypodermic needle or other fluid injector.

Inflation of the bladder 2202 increases the surface area of the bladder 2202. This expansion creates a stress at an interface 2208 between the bladder 2202 and the adhesive composition 2203 because the adhesive composition 2203 may not expand as much as the bladder 2202. The expansion of the bladder 2202 weakens a bond between the bladder 2202 and the adhesive composition 2203.

FIGS. 22A and 22B are illustrative of how inflating the bladder 2202 may weaken the bond between the bladder 2202 and the adhesive composition 2203. FIG. 22A illustrates an embodiment of a bladder 2202 similar to the bladder 1302 illustrated in FIG. 13B, but where the bladder 2202 has been deflated. The interface 2208 between the bladder 2202 and the adhesive composition 2203 is greater than the interface 2208 between an inflated bladder 2202 and the adhesive composition 2203, such as the interface 2208 shown in FIG. 22B. That is, the surface area of the bladder 2202 that is in contact with the adhesive composition 2203 is greater in FIG. 22A than it is in FIG. 22B. Also, the circumference of the bladder 2202 is greater when inflated, as illustrated in FIG. 22B. Therefore, an inflated bladder 2202 puts a stress at the bladder-adhesive interface 2208 by increasing the circumference of the bladder 2202, while the adhesive composition 1303 may be more resistant to expansion. This stress at the bladder-adhesive interface 2208 results in portions of the bladder 2202 breaking free from portions of the adhesive composition 2203. As a result, the surface area of the bladder 1302, which is bonded to the adhesive composition 2203, is reduced when inflated.

In one embodiment, the inflated bladder 2202 may completely detach from the adhesive composition 2203. In another embodiment, the inflated bladder 2202 may only partially detach from the adhesive composition 2203. In one embodiment, once the bond between the bladder 2202 and the adhesive composition 2203 has been weakened, the anchor 2201 may be more easily removed, while reducing the incidences of injury to the skin. In one embodiment, portions of the bladder 2202 may tear off and remain attached to the adhesive composition 2203 upon removal of the anchor 2201. A portion of the adhesive composition 2203 may remain on the skin and slough off over time as the outer layer of skin desquamates (i.e., the outer layer of dead skin flakes or peels off).

Figure 23A:
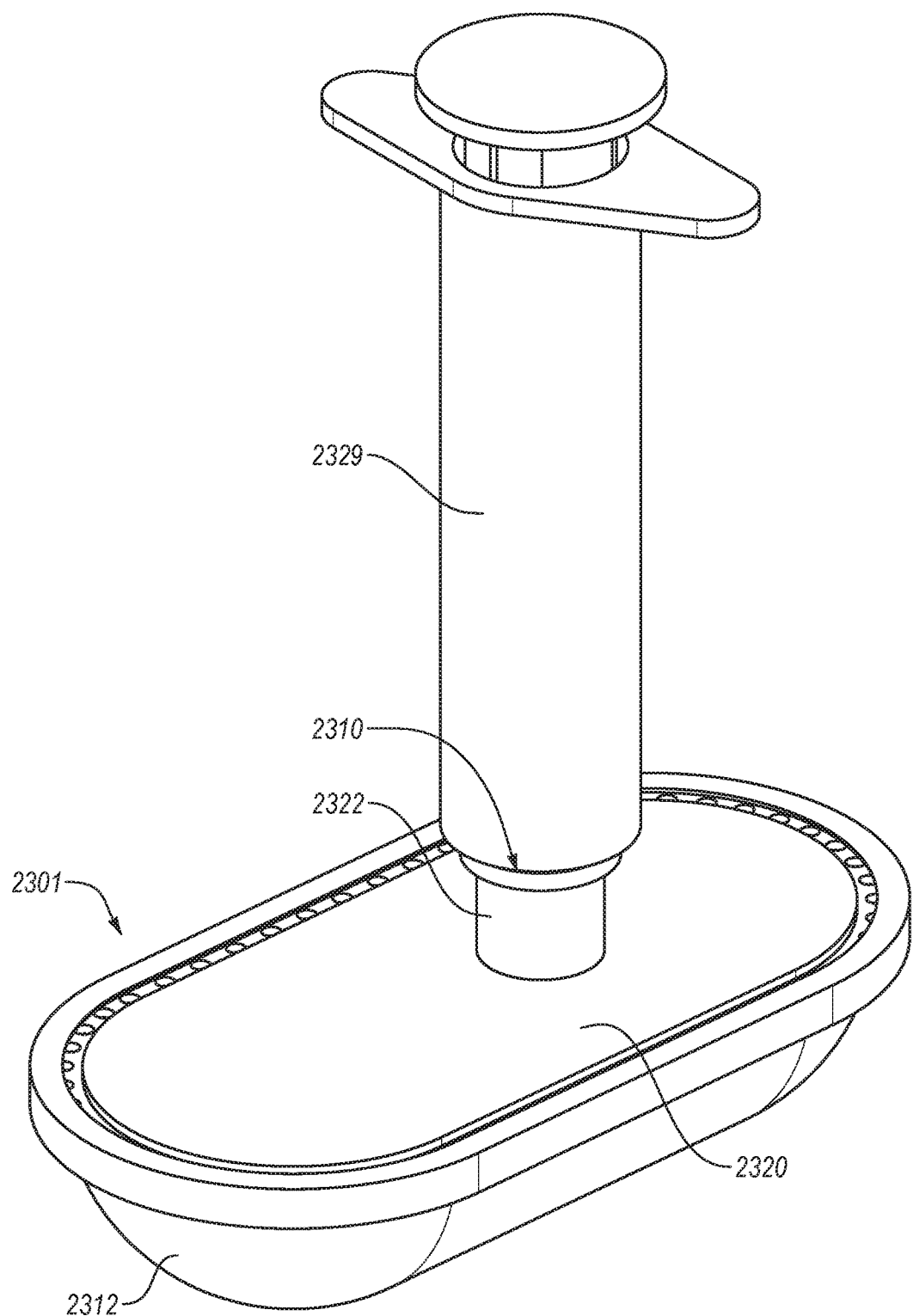
FIGS. 23A-23B illustrate various views of an embodiment of a tensioning anchor wherein a bottom compliant membrane has been inflated.
Figure 23B:
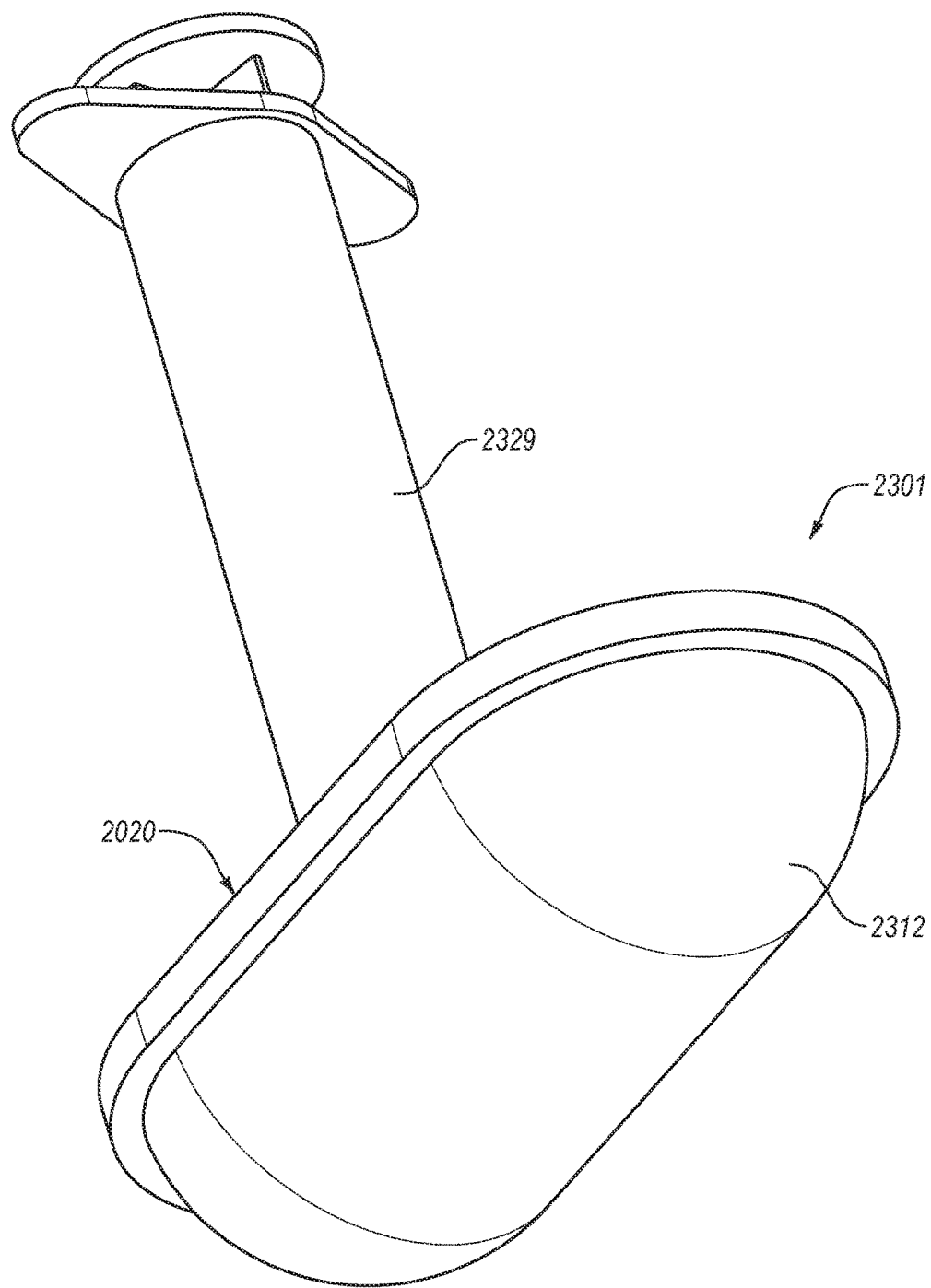

FIGS. 23A and 23B illustrate an embodiment of an anchor where the expandable membrane is a bottom layer 2312 of a base member 2320. The illustrated embodiment of the anchor 2301 may include a base member 2320 having a bottom layer 2312 enclosing an inner chamber (not shown). The bottom layer 2312 may be compliant and expandable. As illustrated in FIGS. 23A and 23B, the introduction of a fluid into the internal chamber (not shown) by a syringe 2329 via the port 2310 causes the expandable bottom layer 2312 to expand. This expansion increases the surface area of the bottom layer 2312, which stresses a bond between the adhesive composition and the bottom layer 2312. This stress weakens the bond and allows the anchor 2301 to be removed from the adhesive composition and therefore the patient.

The bottom layer 2312 of the anchor 2301 illustrated in FIGS. 23A and 23B may have thick walled portions and thin walled portions. An adhesive composition may be applied only to the thin walled portions of the bottom expandable layer 2312. In this way, the thin walled portions expand more than the thick walled portions when a fluid is introduced into the inner chamber (not shown) through the port 2310. The base member 2320 may be more rigid than the bottom layer 2312, or at least more rigid than the thin walled portions of the bottom layer 2312, so as to be more resistant to expansion upon the introduction of a fluid into the inner chamber (not shown). The thin walled portions of the bottom layer 2312 may be made of any medically acceptable elastic or plastic material capable of expansion, and which is impermeable to a fluid used to inflate it. For example, the bladder may be made of plastics, rubbers, nitrile, polyurethanes, polyethylenes, ethylene propylene diene monomer (EPDM), vinyl, silicone elastomers, neoprene, or combinations thereof.

In the embodiment of the anchor 2301 illustrated in FIGS. 23A-B, a single inner chamber (not shown) is partially defined by the entire bottom layer 2312. In another embodiment, the anchor 2301 may have multiple inner chambers, which may each be partially defined by one or more distinct portions of the bottom layer 2312. In other embodiments, each inner chamber may be accessed independently by a port 2310. In other embodiments, a port 2310 may be a means for introducing a fluid into multiple inner chambers simultaneously.

Other embodiments of the anchor 2301 may include combinations of components or features of other embodiments herein described. For example, one embodiment of an anchor may include a combination of a bottom layer 2312 with compliant portions as well as one or more bladders 2202 disposed on a bottom surface of the bottom layer 2212. Other embodiments may include combinations of embodiments herein described where the number and configuration of ports, bladders 2202, compliant portions 2212, base members 2020, and bottom layers 2005 may vary.

Referring back to FIG. 22A-B, the adhesive composition 2203 may be applied so that only the bladder 2202 (or expandable bottom layer 2312 illustrated in FIGS. 23A-B) binds to the skin. In one embodiment, an adhesive composition 2203 may be first applied to the bladder 2202 and subsequently adhered to the skin. In another embodiment of the anchor 2201, the adhesive composition 2203 may first be applied directly to the skin of a patient. For example, the adhesive composition 2203 may first be applied to the skin of a patient around an aperture. The anchor 2201 may then be placed onto the skin so that the one or more bladders 2202 make contact with the adhesive composition 2203 on the skin. In yet another embodiment, the bottom layer 2212 of the anchor illustrated in FIG. 23A-B may be separate from the base member 2320. In this embodiment, the expandable bottom layer 2312 may first be adhered to the skin, and the base member 2320 may subsequently be adhered to the bottom layer 2312. The adhesive composition 2203 may include one or more adhesive compositions described herein.

At least a portion of one or more of the bottom surfaces (e.g., bottom surface 1305, 1505, 1605, 1705, 1805, 1905, 2005, 2105, 2205) described herein may include surface characteristics. For example, the surface characteristics may include ridges, dimpling, scales, surface roughening, other surface characteristics, or combinations thereof. In some embodiments, the surface characteristics may be directionally oriented. For example, one or more of the surface characteristics (e.g., angled ridges and/or wave-like ridges may be at an acute angle) may have increased friction in at least one direction (e.g., similar to shark scales). The direction of the surface characteristics may be indicated on the surface of the device to allow the device to be placed such that the surface characteristics may be aligned with in a predetermined orientation.

In the embodiment illustrated in FIG. 24, an adjustment mechanism 2424 may be coupled to the receiving member 2422. The port 2410 may be separate from the adjustment mechanism 2424 and/or receiving member 2422, but they may also be integrated together. In the illustrated embodiment, the adjustment mechanism 2424 is a dial. The dial 2424 may be rotated in one direction to draw in the connecting member 2421 in towards the anchor 2401 or rotated in the other direction to release the connecting member 2421 out away from the anchor 2401. Other adjustment mechanisms 2424 may be used that release out and or draw in the connecting member 2421 upon activation.

The dial 2424 shown in an embodiment of the anchor 2401 illustrated in FIG. 24 may include a ratchet mechanism, wherein a rotation of the dial 2424 in only one direction is possible. In this way, a connecting member 2421 may be drawn in toward the anchor 2401 and locked in place. This may prevent the connecting member 2421 from being released out away from the anchor 2401 unintentionally due to a tension in the connecting member 2421. Other locking mechanisms may be employed that prevent the connecting member 2421 from being drawn out away from the anchor 2401. For example, a clamp or a set screw may be used to lock the connecting member 2421 in place. A release mechanism may also be provided in order to unlock the adjustment mechanism 2424 and allow the connecting member 2421 to be released out away from the anchor 2401, thus decreasing a tension in the connecting member 2421.

In another embodiment, a tensioning anchor 2421 may include ventilation features 2427. The ventilation features may be configured to promote airflow to the skin of a patient when an anchor has been adhered to the skin. For example, in an embodiment shown in FIG. 24, where expandable membrane 2412 is disposed at a perimeter edge of the anchor 2401, slits, holes, or cuts may be present in the base member 2420 to allow air to flow through the anchor 2401. Other ventilation features that allow air to flow through the anchor 2401 to access the skin may also be utilized. These may include holes, screens, vents, mesh material, fabric sections, or other breathable materials sections of the base member 2420.

Figure 25:
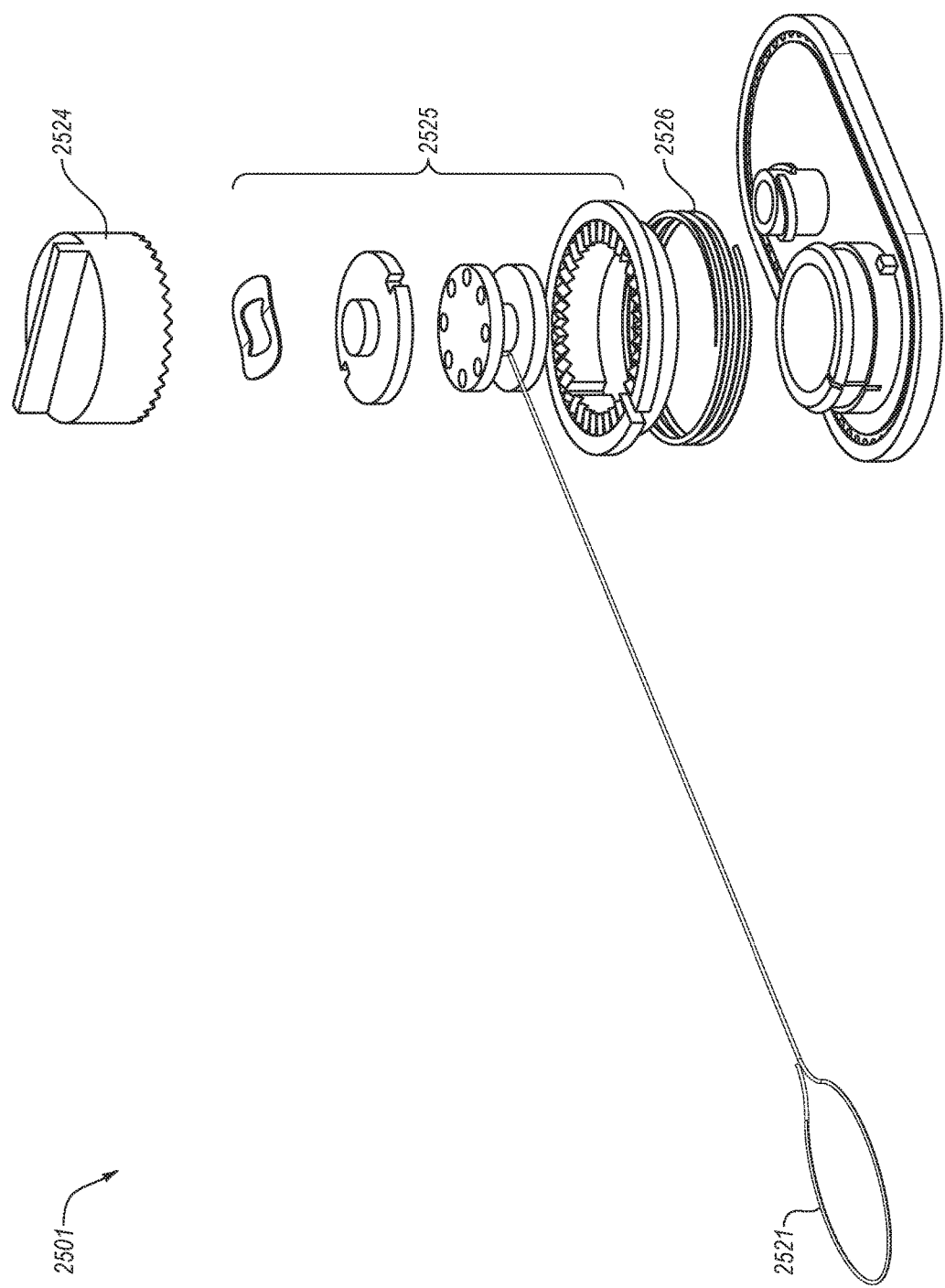
FIG. 25 illustrates an exploded view of an embodiment of a tensioning anchor that includes an adjustment mechanism and a torque limiting slip clutch.

In the embodiment illustrated in FIG. 25, an anchor 2501 includes a spring 2526 coupled to an adjustment mechanism 2524. The spring 2526 may bias the adjustment mechanism 2524 in either direction. For example, the spring 2526 may exert a force on the adjustment mechanism 2524 in opposition to a tension force exerted by the connecting member 2521. This configuration may encourage a release of the connecting member 2521 when the adjustment mechanism 2524 is unlocked. Alternatively, the spring 2526 may also be configured to exert a force on the adjustment mechanism 2524 in the other direction, thus discouraging a release of the connecting member 2521 when the adjustment mechanism 2524 is unlocked.

Another embodiment of a tensioning anchor may include a force gauge (not shown). A force gauge may measure the force exerted by the anchor 2501 on the skin of a patient and relay the information to the user. The force gauge may be located anywhere on the anchor 2501 so as to effectively measure and communicate the exerted force. The force gauge may be digital or analog. The force gauge may provide visual or audio feedback to a person installing the anchor on a patient, alerting them of the force exerted by the anchor 2501 on the skin of a patient.

FIG. 25 illustrates an embodiment of an anchor 2501 that may include an adjustment mechanism 2524 with a torque limiting slip clutch 2525. Such a slip clutch 2525 may limit the amount of tension the adjustment mechanism 2524 creates in the connecting member 2521. As a connecting member 2521 is drawn into the anchor 2501 by activation of the adjustment mechanism 2524, a tension in the connecting member 2521 may increase. The tension in the connecting member 2521 may be transferred to the skin through the anchor 2501 that has been adhered to the skin. It may be desirable to limit the amount of force applied to the skin, for example, to limit damage to the skin. The slip clutch 2525 may be set to a desired force limit setting. When the force limit is reached by an activation of the adjustment mechanism 2524, the slip clutch 2525 may be activated. The slip clutch 2525 may prevent a tension in the connecting member 2521 from exceeding the desired force limit.

Figure 26:
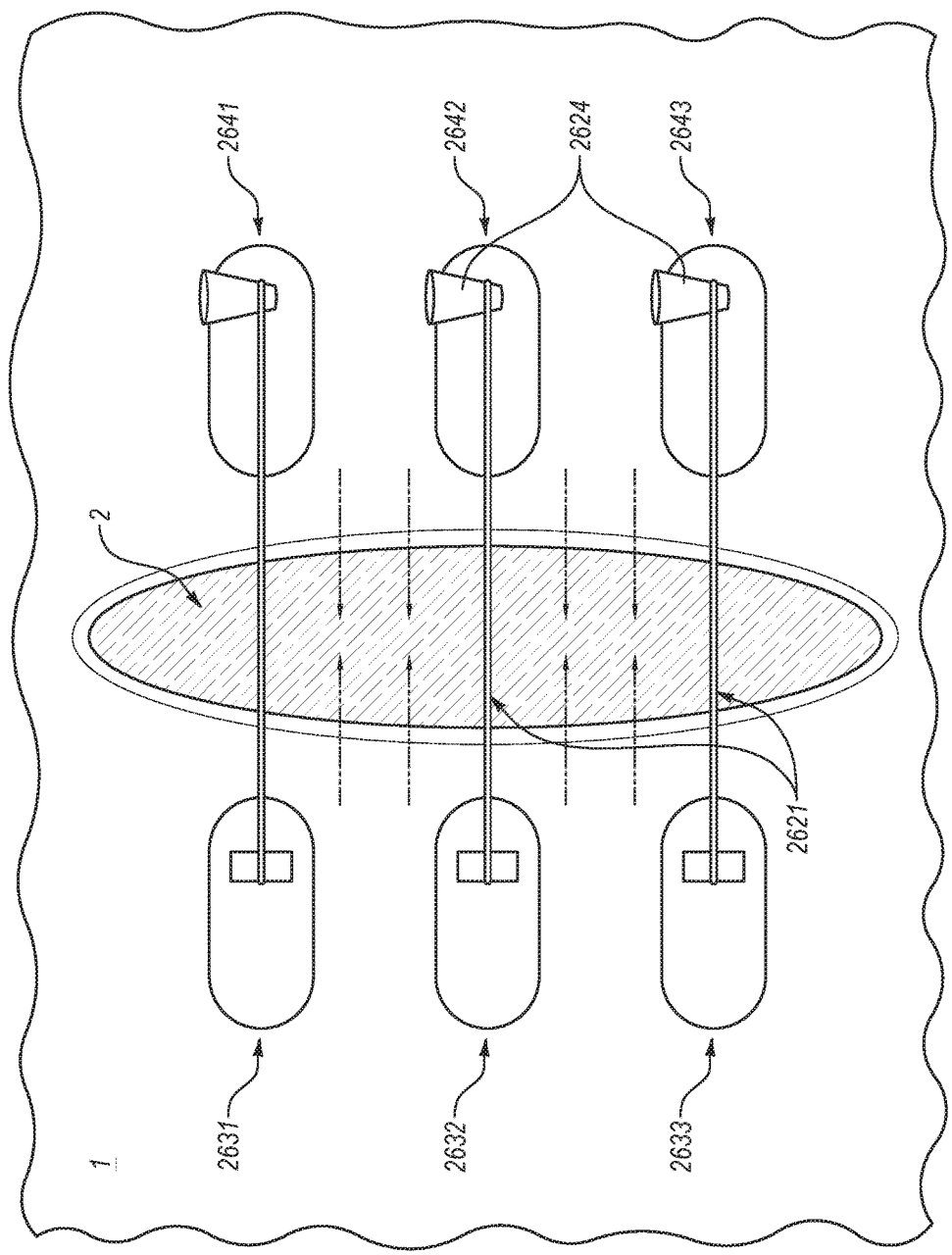
FIG. 26 illustrates a top view of an embodiment of a wound closure system.

An embodiment of a system including two or more anchors is illustrated in FIGS. 26 and 27. In an embodiment of a system shown in FIG. 26, anchors 2631, 2632, 2633, 2641, 2642, 2643 are placed on opposing sides of an aperture 2 (e.g. a wound, surgical incision, or other aperture). The anchors 2631, 2632, 2633, 2641, 2642, 2643 may be connected by one or more connecting members 2621. Each anchor 2631, 2632, 2633 may be paired with an opposing anchor 2641, 2642, 2643 on an opposite side of the aperture 2. The pairs of opposing anchors may include one or more anchors 2641, 2642, 2643 that may include adjustment mechanisms 2624 (hereinafter referred to as adjustable anchors 2641, 2642, 2643) and one or more anchors 2631, 2632, 2633 that do not include adjustment mechanisms (hereinafter referred to as static anchors 2631, 2632, 2633). Opposing anchors may be connected via a single connecting member 2621, as shown, or may be connected via multiple connecting members 2621. The connecting members 2621 may span the aperture 2 FIG. 26 illustrates six anchors 2631, 2632, 2633, 2641, 2642, 2643 arranged in three pairs. Each adjustable anchor 2641, 2642, 2643 may be adjusted to draw in the connecting member 2621 toward the anchor 2641, 2642, 2643, thus decreasing the distance between a pair of anchors and drawing the aperture 2 toward a closed state. Each adjustable anchor 2641, 2642, 2643 may be adjusted independently.

Another embodiment of a system of anchors is illustrated in FIG. 27. In this embodiment, two adjustable anchors 2741, 2742 and one static anchor 2731 are adhered to the skin 1 of a patient on various sides of an asymmetrical aperture 2. A single connecting member 2721 may connect all three anchors 2741, 2742, 2731. The connecting member 2721 may span the aperture 2. Each adjustable anchor 2741, 2742 may be adjusted independently. Decreasing the distance between the anchors by activating the adjustment mechanism 2724 of the adjustable anchors 2741, 2742 may draw the aperture 2 toward a closed state.

In another embodiment not shown, a single adjustable anchor and one or more static anchors may be adhered to the skin of a patient. For example, the embodiment of the system illustrated in FIG. 26 may include only one adjustable anchor 2741 and a single connecting member 2721. An adjustment of the adjustable anchor 2741 would cause every other anchor 2731, 2742 to be drawn towards one another, thus relieving a stress in the aperture 2 and drawing it closed. In other embodiments of anchor systems, only two anchors may be adhered to the skin. Any number of anchors may be adhered and connected in any number of configurations. One may appreciate from the embodiments described herein that numerous configurations of multiple anchor systems may be employed. The number of anchors and their position on the skin of a patient may depend on the shape of the aperture 2 and the force required to close the aperture 2. Indeed, one of the advantages of one or more embodiments of the systems herein described is the adaptability of the system in order to meet the various needs of different patients and apertures. For example, small wounds may only require two opposing anchors, while larger wounds may require many more. Anchors may be placed on opposing sides of irregularly shaped wounds. A system of anchors may also be configured to close multiple wounds simultaneously. One may appreciate from the above description that nearly an infinite number of system configurations may be employed.

Stitches, sutures, and staples may not be necessary to close an aperture using the described tensioning anchors and systems. At least one embodiment of the anchors described herein may leave no scars and/or may not otherwise damage the skin of the patient. Once a wound has healed and the anchors are removed, the remaining portions of adhesive composition may slough off over time as the outer layer of skin desquamates.

The total force applied on the skin of a patient by a tensioning anchor system is divided by the total surface area of the multiple anchors in contact with the skin. Therefore, a large force may be applied to close an aperture with relatively small forces applied to the skin by each individual tensioning anchor.

IV. Adhesive Composition

As described, the barrier device can be utilized with an adhesive in order to provide the static or stable retention of the medical device with respect to the incision as well as the inhibition or prevention of infections from entering the incision. A variety of adhesive compositions can be used, such as those that are compatible with the skin that do not cause serious skin irritation. Also, the adhesive composition can be compatible with the barrier device and medical device so as to promote adhesion with limited damage or degradation of the structural integrity thereof.

In one embodiment, the adhesive composition is any biocompatible adhesive. As such, reference to an adhesive composition herein is a natural or synthetic substance that adheres to skin without substantial side effects or complications. Examples of such biocompatible adhesive composition (bioadhesives) are substantially non-toxic, non-inflammatory, and configured to adhere to the body of a medical device and to skin. These types of adhesive compositions, contact adhesives, are commonly used in transdermal drug delivery devices. Also, these types of adhesive compositions are well known to those of ordinary skill in the relevant arts.

In one embodiment, the bioadhesive is a polymer or monomer that polymerizes into a polymer that is configured to adhere to skin and to the body of a medical device. For example, the polymer is biocompatible and flexible. This allows for being directly applied to the skin at a site of insertion of a medical device, and allows the medical device the ability to move with respect to the insertion site without breaking the adhesive bond.

In one embodiment, the bioadhesive is comprised of silicones, vinyls, polyethylenes, polyvinylchlorides, polyacrylates, polymethacrylates, polyisobutylenes, monomers thereof that form adhesive, and the like which are biocompatible.

In one embodiment, the bioadhesive is comprised of serum albumin and glutaraldehyde, such as BioGlue™.

In one embodiment, the bioadhesive is a composition that includes a cyanoacrylate. Cyanoacrylates are compounds commonly used in the adhesive industry. For example, the cyanoacrylate can include a methyl-2-cyanoacrylate ethyl-2-cyanoacrylate (i.e., Superglue™ and Krazy Glue™), and 2-octyl cyanoacrylate or n-butyl-cyanoacrylate, which are used in medical glues (i.e., Dermabond™ and Traumaseal™), a polyacrylate, polycyanoacrylate, other cyanoacrylates, and combinations thereof. Cyanoacrylate is a tenacious adhesive, particularly when used to bond skin with a medical device, where the skin usually has minute traces of water. In its liquid form, cyanoacrylate consists of monomers of cyanoacrylate molecules. Methyl-2-cyanoacrylate ($CH_2$=$C(CN)COOCH_3$ or $C_5H_5NO_2$) has a molecular weight equal to 111.1, a flashpoint of 79° C., and 1.1 times the density of water. Ethyl-2-cyanoacrylate ($C_6H_7NO_2$) has a molecular weight equal to 125 and a flashpoint of >75° C. Also, the cyanoacrylates are susceptible to fracture and loss of adhesiveness when chilled to an appropriate temperature, which allows for the use of chilling in order to remove the barrier device from the skin of a subject.

Generally, a cyanoacrylate is an acrylic resin which rapidly polymerizes in the presence of water, forming long, strong chains, joining the bonded surfaces together. Because the presence of moisture causes the glue to set, exposure to moisture in the air can cause a tube or bottle of glue to become unusable over time. To prevent an opened container of glue from setting before use, it should be stored in an airtight jar or bottle, and optionally with a package of silica gel.

Cyanoacrylate sets quickly, often in less than a minute. A normal bond reaches full strength in two hours and is waterproof. Accelerators such as toluidine trigger setting in two or three seconds, with some loss of strength.

The adhesive composition can be configured so as to produce and maintain strong glue-skin, glue-barrier device, and glue-catheter adhesive interfaces. Such strong adhesive composition interfaces have been shown by adhering materials (e.g., polyurethanes, polyethylenes, polypropylenes, PVC, Teflon, and the like) that can be used in the barrier device and medical device to skin with an adhesive in accordance with the present disclosure. Thus, the adhesive and/or device of the present disclosure could be used as an antimicrobial barrier for most central venous catheter sites of insertion, as well as other sites of insertions for other medical devices.

Alternatively, the cyanoacrylate can be substituted by another bioadhesive that is configured to adhere to skin and to the body of a medical device, such as a catheter. This is because certain polymers, which are bioadhesive, can create an occlusive barrier between the skin and a medical device, wherein the occlusive barrier is resistant to penetration by bacteria or other microbes. Applying these polymers at the site of catheter entry or entry of other medical device through the skin prevent catheter-related infections by inhibiting microbes from entering into the site of entry and colonizing at the percutaneous site and/or on the catheter portion that is disposed within the skin.

Experiments can be utilized to determine whether a bioadhesive is suitable for the present disclosure. Suitable bioadhesives can be applied to the skin and medical device at the site of insertion to form a barrier. The barrier can be visually inspected to insure the barrier is sufficient. For example, a histologic cross-section can be studied to ensure the bioadhesive is sufficient. Additionally, the barrier can be examined for barrier function by examining the movement of bacteria after being placed over the intact barrier, and evaluating for penetrance of those bacteria beyond that barrier.

In one embodiment, one or more different types of adhesive compositions can be used at various locations of the barrier device, skin, and/or medical device. This can include one type of adhesive composition for the base surface and a different adhesive composition for the perimeter. For example, a weaker adhesive composition can be used on the base while a stronger adhesive composition can be used at the perimeter.

In one embodiment, the base surface can include a peelable liner that protects an adhesive composition disposed on the base surface such that the base surface can be adhered to the skin after the peelable liner is removed. The adhesive composition on the base surface under the peelable liner can be any type of adhesive, such as pressure adhesives and those adhesive compositions used in transdermal devices. Thus, the base of the barrier device can be applied to the skin similarly to a transdermal device. Moreover, a drug can be included in the adhesive on the base surface so that the barrier device can be used as a transdermal drug delivery device. This can include the use of anesthetics, antimicrobials, or the like being delivered to the skin under the barrier device.

V. Kit

One or more components of the embodiments described herein may be provided in a kit. For example, in one embodiment, the present disclosure includes a catheter kit that has a barrier device and adhesive, such as a cyanoacrylate, as described herein. The barrier device and/or adhesive can be configured to be placed at the catheter insertion site as described so as to form a barrier with the skin and catheter so that microbes are inhibited from entering the insertion site. For example, the anti-microbial barrier formed from the barrier device and adhesive can be maintained when used on a percutaneously placed central venous catheter.

In one embodiment, the present disclosure includes an adhesive (e.g., cyanoacrylate) and barrier device that can be used together to form an anti-microbial barrier for an opening in skin where a medical device extends through. For example, the cyanoacrylate composition and/or device can be used as a mechanical and/or therapeutic barrier that has antimicrobial properties. That is, the cyanoacrylate composition and/or device can physically prevent microbes from entering a medical device insertion site and can effect antimicrobial properties.

In one embodiment, the present disclosure includes a wound closure kit that has one or more anchors, one or more connecting members, and an adhesive composition, such as a cyanoacrylate, as described herein. Tensioning anchors, connecting members, and adhesive compositions may be configured around an aperture, such as a wound, surgical incision, or other aperture, in order to close it, thus aiding in the healing process. Alcohol pads, iodine swabs, surgical gloves, and other sanitary equipment may also be included in the kit and utilized to minimize infection or wound exposure to bacteria before, during, and after the use of a wound closure system. A syringe or other fluid injector may also be included in the kit. The syringe may be used to introduce a fluid into an inner chamber of a bladder or anchor. This fluid introduction may inflate the bladder or expandable membrane of two or more anchors that have been adhered to skin.

VI. Application

In one embodiment, the present disclosure includes a method of using a barrier device in combination with an adhesive, such as those that contain a cyanoacrylate, in order to form an impermeable barrier against bacteria at a percutaneous incision site for passing a medical device into or through skin. As such, the device and adhesive are placed at the incision so as to contact the skin and barrier device so as to form a barrier. Also, the adhesive can be used to form barriers between the barrier device and medical device as well as between the skin and medical device in order to provide one or more barriers as described. The one or more barriers can retain the medical device in a static position relative to the skin and incision such that a barrier inhibits bacteria from entering the incision. Bacteria tend to infect catheters by contaminating the catheter at the site of the percutaneous incision and subsequently traveling down the external surface of the catheter and into the bloodstream. Thus, the one or more barriers formed with the barrier device and adhesive can both provide a static medical device position as well as provide a barrier that inhibits microbial infections in the incision.

In one embodiment, the barrier is formed from a flowable adhesive composition that hardens at a skin-barrier device interface, skin-medical device interface, and/or barrier device-medical device interface. Such flowable adhesive compositions can be liquids, gels, pastes, and the like. The flowable composition can be placed onto the skin, barrier device, and medical device at an interface therebetween, which is usually at, adjacent, or proximal with the percutaneous incision. For example, an adhesive composition can be administered onto the skin adjacent to a percutaneously inserted intravascular catheter and the barrier device can be applied to the adhesive so as to receive the catheter therein so as to reduce the risk of developing a catheter-related infection. In another example, a fluid (e.g., liquid or paste) adhesive is applied to the intersection between the skin and the perimeter of the barrier device so as to create a perimeter barrier therearound. In yet another example, the adhesive is applied to a medical device disposed in an incision, and the barrier device is slid or applied over the medical device so as to come into contact with the skin so that a barrier forms between the medical device and barrier device (and optionally to the skin) in the barrier device conduit. In still yet another example, adhesive is applied to the barrier device at the top opening from with the medical device protrudes to form a barrier with the medical device. In another example, adhesive is applied to a clam-type barrier device that is then closed around the medical device and adhered to the skin. In yet another example, adhesive is applied to a groove and base surface of a barrier device and then the barrier device is applied to the medical device and skin such that the medical device is adhered to the groove and the base surface is adhered to the skin.

In an embodiment of a barrier device, an adhesive composition may reside in capsules disposed on the bottom surface of a barrier device. The capsules act as a barrier to the adhesive composition until the device is applied to a surface. When the barrier device is placed on a surface, a pressure may be applied to the top surface of the barrier device over the capsules residing underneath. The capsules may rupture, become leaky, or otherwise fail under pressure, thus releasing the adhesive composition, adhering the barrier device to a surface, such as the skin of a patient.

In another embodiment, illustrated in FIGS. 18A and 18B, an adhesive composition may reside in a groove in a bottom surface of a barrier device. A seal may span the groove and seal the adhesive composition within the groove. The adhesive composition and the seal may be placed on or in the bottom surface of the barrier device during the manufacturing of the barrier device. The seal may prevent the adhesive composition from being exposed to air, thus preventing polymerization, until the barrier device is adhered to a surface. The adhesive composition is free to make contact with the skin of a patient and adhere the barrier device to the skin upon removal of the seal. FIG. 18B illustrates an embodiment of a barrier device that includes an easy-release seal. An easy-release seal may include a pull tab. A person removing the seal may grab hold of the pull tab and pull the seal away from and off of the barrier device. Once the seal is removed and the adhesive composition is exposed, there will be a window of time before the adhesive composition polymerizes. The barrier device may be adhered on the skin of a patient within this window of time. That is, after the removal of the seal but prior to polymerization of the adhesive composition. Other methods of use are also contemplated.

In one embodiment, the barrier device and adhesive can be used to inhibit or prevent pistoning of the catheter within the incision. Pistoning can include slight movements, in and out, of the catheter that can introduce bacteria into the incision and catheter tract. Sutures have been found to be insufficient to prevent pistoning; however, the use of the barrier device and adhesive can effectively inhibit pistoning. Additionally, sutures form additional holes in the skin which themselves can lead to infection. The barrier device of the present disclosure can be used to inhibit slight pistoning. This can include inhibiting pistoning that moves the medical device from about 0.5 mm to about 10 mm into or out of the incision, from about 1 mm to about 5 mm, or about 2 mm to about 3 mm movements can be prevented. This can prevent infectious material from being introduced into the catheter line or other incision having a percutaneous medical device.

While some pistoning may occur during use of the device, the sterile environment around the incision and proximal portions of the medical device provided by the barrier device can be maintained so that infections are not introduced into the incision. As such, the barrier device maintains sterility of the incision as proximal areas by virtue of the barriers that are formed by the barrier device and adhesive combination. Accordingly, minor pistoning may occur, but substantially no microbes will be able to enter into and infect the incision.

In one embodiment, the present disclosure includes a method for removing the adhesive-formed barrier and barrier device from the skin around or adjacent to the incision site between the skin and medical device. Such a method can include applying a solvent to the adhesive so as to degrade the adhesive so that the barrier device can be removed from the skin. Solvents such as acetone or tetrahydrofuran, and the like can be used to soften the cyanoacrylate adhesive. Solvents that soften through dissolve the adhesives of the present disclosure are well known in the art.

Additionally, the adhesive can be cooled so as to cause the bond between the skin, barrier device, and/or medical device to become brittle. This can be accomplished by locally decreasing the temperature with a coolant, such as liquid nitrogen or other cooling fluid. For example, the cooling fluid can be applied to the external surfaces of the adhesive or through conduits to internal surfaces of the adhesive. When the adhesive cools sufficiently, it can be easily cracked or broken in order to remove the barrier device.

Also, an inflatable bladder can be disposed between the barrier device and adhesive such that inflation of the bladder causes the adhesive barrier to break. This inflatable bladder can then be used to separate the bond between the skin and the medical device and/or barrier device so that the medical device and/or barrier device can be removed from the skin. The bladder therefore uses hydraulic pressure to expand and mechanically break the bond of the barrier. A fluid may be introduced into the inner chamber of the bladder through a port, such as a Luer lock connection. A syringe or other injection device may be used to inject the fluid through the port.

The barrier device may be configured such that an inner chamber is enclosed between top and bottom layers of the barrier device. The bottom layer of the device may have thin walled expandable portions. Introduction of a fluid into the inner chamber of the device expands the thin walled portions of the bottom layer, causing the bond between the device and the adhesive composition to weaken. The thin walled portions of the bottom layer of the device use hydraulic pressure to expand so as to mechanically break the bond of the barrier. A fluid may be introduced into the inner chamber through a port, such as a Luer lock connection. A syringe or other injection device can be used to inject the fluid through the port. Other methods of injecting fluid into the inner chamber may also be used. For example, a hypodermic needle may be used to puncture the top or bottom layer of the barrier device and inject a fluid into the inner chamber. The puncture hole, in this method, would be the port through which the fluid is introduced.

Additionally, a release cord could be used in order to break the barrier between the barrier device and skin. For example, a release cord attached to the barrier device can be pulled so that it cuts the adhesive barrier and separates the barrier device from the skin. Such a release cord can also separate the barrier device from the medical device.

Of course, the skin, barrier device, and medical device can be sterile during the use described herein. Also, the procedures described can be performed in a manner that does not introduce or propagate infections. Additionally, sterilization techniques can be conducted to sterilize the skin, barrier device, and medical device before, during, and/or after placement of the catheter into an incision as well as placement of the barrier device with respect to the medical device and skin.

In one embodiment, the present disclosure includes a method for applying a system of anchors to a surface, such as the skin of a patient. The anchors may be arranged adjacent to an aperture (e.g. surgical incision, wound, or other aperture). A flowable adhesive composition may be applied to the anchors and/or to the skin where the anchors are to be placed. Such flowable adhesive compositions can be liquids, gels, pastes, and the like. The flowable adhesive composition may be placed onto the skin, anchor, at an interface therebetween, or combinations thereof. The anchor may be placed adjacent to an aperture. In one example, adhesive is applied to a base surface of an anchor and then the anchor is applied to the skin such that the anchor is adhered to the skin. In yet another example, the adhesive composition resides in capsules disposed on the bottom surface of the anchor or bladder. The capsules act as a barrier to the adhesive composition until the anchor is used. When the anchor is placed on a patient, a pressure may be applied to the top surface of the anchor over the capsules residing underneath. The capsules fail under pressure and release the adhesive composition, adhering the anchor to the patient.

In one embodiment, an adhesive composition resides in a groove in the bottom surface of the anchor. A seal may span the groove and seal the adhesive composition within the groove. The adhesive composition and the seal may be placed on or in the anchor during the manufacturing of the anchor. The seal prevents the adhesive composition from exposure to air, thus preventing polymerization, until the anchor is used. The adhesive composition is free to make contact with the skin of a patient and adhere the anchor to the skin upon removal of the seal. A pull tab may be utilized to grab hold of the seal, which may then be removed by pulling it away from the anchor. Once the seal is removed and the adhesive composition is exposed, the adhesive composition will have a window of time before it polymerizes. The anchor may be positioned on the skin of a patient within this window of time. That is, after the removal of the seal but prior to polymerization.

Once the adhesive composition has polymerized and adhered the anchors to the skin, one or more connecting members may be secured to the anchors via the receiving members on the anchors. A connecting member may be configured to connect two or more anchors together. One may appreciate, from the description of multiple embodiments and configurations of wound closure systems described herein, that any configuration of anchor positions on the skin of a patient may be achieved.

In some embodiments, once the anchors and receiving members are in place, an adjustment mechanism on one or more of the anchors may be activated. An activation of the adjustment mechanism draws the connecting member in toward the anchor, thus decreasing the distance between connected anchors. This may draw the skin on opposing sides of a wound or incision closer together, thus relieving stress in the wound and potentially closing it. Once a desired closure has been achieved by adjusting the anchor or anchors, the adjustment mechanism on one or more of the anchors may be locked so as to prevent the connecting member from being released out away from the anchor or anchors. The distance between connected anchors will remain constant until the locking mechanism is unlocked and the connecting member may be drawn out away from one or more of the anchors.

After a period of time, the connecting member may be readjusted to continue closing a wound. For example, the skin may stretch allowing for increased tension to be applied to one or more connecting members (e.g., via one or more adjustment mechanisms).

In one embodiment, the present disclosure includes a method for removing the tensioning anchors from a surface, such as the skin of a patient around or adjacent to an aperture. Such a method may include disposing an inflatable bladder between the anchor and adhesive composition such that inflation of the bladder results in a weakening of the bond between the adhesive composition and the barrier device. The tensioning anchors may then be removed from the adhesive composition. Portions of the adhesive composition may remain on the skin of the patient and slough off over time as the outer layer of skin desquamates. A fluid may be introduced into an inner chamber of the bladder through a port, such as a Luer lock connection. A syringe or other injection device may be used to inject the fluid through the port. Other methods of injecting fluid into the inner chamber may also be used. For example, a hypodermic needle may be used to puncture the bladder wall and inject a fluid into the inner chamber. The puncture hole, in this method, would be the port through which the fluid is introduced.

One or more anchors may be configured such that an inner chamber is enclosed by top and bottom layers of the base members of the anchors. The bottom layer of the anchors may have thin walled expandable regions. Introduction of a fluid into the inner chamber of the anchor may cause an expansion of the thin walled portions of the bottom layer, weakening a bond between the adhesive composition and the anchor. The thin walled portion of the bottom layer of the anchors uses hydraulic pressure to expand and mechanically weaken the adhesive bond. Fluid may be introduced into the inner chamber through a port, such as a Luer lock connection. A syringe or other injection device may be used to inject the fluid through the port.

Anchor systems and/or surfaces to which they may be applied may be sterile during the use described herein. The procedures described may be performed in a manner that does not introduce or propagate infections. Sterilization techniques may be conducted to sterilize the skin, barrier device, and anchors, during, and/or after placement of the barrier device and anchors on the skin of a patient.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references (e.g., journal articles, published patent applications, patents, websites, and the like) that are recited herein are incorporated herein by specific reference in their entirety.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

It should be understood that any directions or reference frames in the preceding description are merely relative directions or movements. For example, any references to "front" and "back" or "top" and "bottom" or "left" and "right" are merely descriptive of the relative position or movement of the related elements.

The invention claimed is:

1. A surface barrier device for creating a barrier around an aperture in a patient's skin, comprising:
    a top surface and a bottom surface, wherein the bottom surface is configured to make contact with said skin;
    a compliant portion;
    an enclosed inner chamber, wherein the inner chamber is at least partially enclosed by the complaint portion;
    an adhesive composition, wherein the adhesive composition is applied to the compliant portion so as to adhere the compliant portion to said skin; and
    a port configured to receive a fluid into the inner chamber, the compliant portion configured to expand upon receiving a fluid into the inner chamber, the expansion weakening a bond between the adhesive composition and the compliant portion.

2. The surface barrier device of claim 1, further comprising a top layer and a bottom layer, wherein the inner chamber is enclosed between the top and bottom layers, a bottom surface of the bottom layer making contact with said skin, the bottom layer comprising one or more compliant portions.

3. The surface barrier device of claim 2, wherein the bottom layer is comprised of a material with a thickness, the compliant portions of the bottom layer having a reduced thickness.

4. A method for removing the surface barrier device of claim 1 that has been adhered to a patient having skin using an adhesive composition, the method comprising:
    injecting a fluid into the inner chamber; and
    expanding the compliant portion, the expansion weakening a bond between the compliant portion and the adhesive composition.

5. The method of claim 4 further comprising exerting a force on the barrier device to detach the barrier device from the adhesive composition, wherein a portion of the adhesive composition remains on the skin of the patient.

6. The surface barrier device of claim 1, wherein the compliant portion is a bladder disposed on the bottom surface of the surface barrier device, the enclosed inner chamber residing within the bladder.

7. The surface barrier device of claim 1, wherein the compliant portion is a bladder disposed around the perimeter edges of the surface barrier device, the enclosed inner chamber residing within the bladder.

8. The surface barrier device of claim 1, wherein the adhesive composition is a cyanoacrylate.

9. The surface barrier device of claim 1, wherein the port comprises a Luer lock connection.

10. The surface barrier device of claim 1, wherein a pressure sensitive adhesive composition is disposed on the bottom surface of the barrier device medial to the compliant portion.

11. The surface barrier device of claim 1, wherein a pressure sensitive adhesive composition is disposed on the bottom surface of the barrier device lateral to the compliant portion.

12. The surface barrier device of claim 1, wherein the port includes a one-way valve.

13. The surface barrier device of claim 1, wherein the adhesive composition is enclosed in a plurality of capsules disposed on the bottom surface of the device, wherein the adhesive composition is released from the capsules and polymerizes, adhering the surface barrier device to the surface, when a pressure is applied to the capsules.

14. The surface barrier device of claim 1, further comprising:
a seal, the seal covering and sealing the adhesive composition, wherein a rupture or removal of the seal exposes the adhesive composition, the adhesive composition polymerizing upon exposure.

15. The surface barrier device of claim 1, further comprising an absorbent material disposed on the bottom surface of the device, the absorbent material located generally medial to the adhesive composition, wherein the absorbent material is configured to absorb excess fluids located on the surface and underneath the barrier device.

16. A method for providing a barrier on a skin surface, comprising:
providing a surface barrier device, the surface barrier device comprising:
a top surface and a bottom surface, wherein the bottom surface is configured to make contact with said skin surface;
a compliant portion;
an enclosed inner chamber, wherein the inner chamber is at least partially enclosed by the complaint portion; and
a port configured to receive a fluid into the inner chamber;
applying an adhesive composition to a surface contacting region of the compliant portion to adhere the compliant portion to said skin surface; and
securing the surface barrier device onto said skin surface, wherein the adhesive composition polymerizes, adhering the surface barrier device to said skin surface, the compliant portion configured to expand upon receiving a fluid into the inner chamber, the expansion weakening a bond between the adhesive composition and the compliant portion.

17. The method of claim 16, further comprising providing a pressure sensitive adhesive on the bottom surface of the surface barrier device.

18. A kit for providing a wound barrier comprising:
a surface barrier device, the surface barrier device comprising:
a top surface and a bottom surface, wherein the bottom surface is configured to make contact with a surface;
a compliant portion;
an enclosed inner chamber, wherein the inner chamber is at least partially enclosed by the complaint portion;
an adhesive composition, wherein the adhesive composition is applied to the compliant portion so as to adhere the compliant portion to a surface; and
a port configured to receive a fluid into the inner chamber, the compliant portion configured to expand upon receiving a fluid into the inner chamber, the expansion weakening a bond between the adhesive composition and the compliant portion;
an adhesive composition; and
a syringe and or other injector for injecting a fluid.

19. The kit for of claim 18, further comprising a surface disinfecting fluid and/or tool.

* * * * *